US012784267B2

(12) United States Patent
Das et al.

(10) Patent No.: US 12,784,267 B2
(45) Date of Patent: Nov. 3, 2026

(54) EXPLAINABLE CONFIDENCE ESTIMATION FOR LANDMARK LOCALIZATION

(71) Applicant: GE Precision Healthcare LLC, Waukesha, WI (US)

(72) Inventors: Bipul Das, Chennai (IN); Deepa Anand, Bangalore (IN); Vanika Singhal, Bangalore (IN); Rakesh Mullick, Bangalore (IN)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 560 days.

(21) Appl. No.: 18/362,224

(22) Filed: Jul. 31, 2023

(65) Prior Publication Data

US 2025/0045951 A1 Feb. 6, 2025

(51) Int. Cl.

| | |
|---|---|
| ***G06T 7/73*** | (2017.01) |
| ***G06T 7/00*** | (2017.01) |
| ***G06V 10/774*** | (2022.01) |
| ***G06V 10/82*** | (2022.01) |
| ***G06V 20/50*** | (2022.01) |

(Continued)

(52) U.S. Cl.

CPC .............. *G06T 7/74* (2017.01); *G06T 7/0012* (2013.01); *G06V 10/774* (2022.01); *G06V 10/82* (2022.01); *G06V 20/50* (2022.01); *G06V 20/70* (2022.01); *G16H 30/40* (2018.01); *G06T 2200/04* (2013.01); *G06T 2207/20081* (2013.01);

(Continued)

(58) Field of Classification Search

CPC ......... G06T 7/74; G06T 7/0012; G16H 30/40; G06V 20/70; G06V 10/82; G06V 20/50; G06V 10/774

See application file for complete search history.

(56) References Cited

U.S. PATENT DOCUMENTS 9,113,781 B2 * 8/2015 Wels .................... A61B 5/0036
9,355,359 B2 * 5/2016 Welinder ............... G06N 20/00

(Continued)

OTHER PUBLICATIONS

Xu et al, Semi-supervised Medical Image Segmentation with Confidence Calibration, International Joint Conference on Neural Networks, 8 pages (Year: 2021).*

(Continued)

*Primary Examiner* — Mohammed H Zuberi
(74) *Attorney, Agent, or Firm* — Amin, Turocy & Watson, LLP

(57) ABSTRACT

Systems/techniques that facilitate explainable confidence estimation for landmark localization are provided. In various embodiments, a system can access a three-dimensional voxel array captured by a medical imaging scanner and can localize, via execution of a first deep learning neural network, a set of anatomical landmarks depicted in the three-dimensional voxel array. In various aspects, the system can generate a multi-tiered confidence score collection based on the set of anatomical landmarks and based on a training dataset on which the first deep learning neural network was trained. In various instances, the system can, in response to one or more confidence scores from the multi-tiered confidence score collection failing to satisfy a threshold, generate, via execution of a second deep learning neural network, a classification label that indicates an explanatory factor for why the one or more confidence scores failed to satisfy the threshold.

20 Claims, 22 Drawing Sheets

(51) Int. Cl.
*G06V 20/70* (2022.01)
*G16H 30/40* (2018.01)

(52) U.S. Cl.
CPC ............... *G06T 2207/20084* (2013.01); *G06T 2207/30004* (2013.01); *G06V 2201/03* (2022.01)

(56) References Cited

U.S. PATENT DOCUMENTS

| | | | | |
|---|---|---|---|---|
| 10,354,555 | B2 * | 7/2019 | Thaler | G09B 23/28 |
| 10,430,946 | B1 * | 10/2019 | Zhou | G06N 3/094 |
| 11,995,820 | B2 * | 5/2024 | Kim | A61B 6/501 |
| 12,056,771 | B1 * | 8/2024 | Contryman | G06Q 40/08 |
| 2018/0060652 | A1 * | 3/2018 | Zhang | G06F 18/25 |
| 2018/0247107 | A1 * | 8/2018 | Murthy | G06V 20/698 |
| 2021/0057067 | A1 * | 2/2021 | Lyman | G06Q 20/14 |
| 2021/0361249 | A1 * | 11/2021 | Kanakatte Gurumurthy | A61B 6/5211 |
| 2023/0298136 | A1 * | 9/2023 | Das | G06V 10/82 382/128 |
| 2024/0249409 | A1 * | 7/2024 | Mayer | G06N 3/0464 |
| 2025/0006372 | A1 * | 1/2025 | Perreault | G06V 20/41 |

OTHER PUBLICATIONS

Charachon et al, Combining Similarity and Adversarial Learning to Generate Visual Explanation: Application to Medical Image Classification, 25th International Conference on Pattern Recognition, 8 pages (Year: 2020).*

Wang et al, A Generalized Explanation Framework for Visualization of Deep Learning Model Predictions, IEEE Transactions on Pattern Analysis and Machine Intelligence, vol. 45, No. 8, Aug. 2023, 19 pages (Year: 2023).*

* cited by examiner

COMPUTE THE SURFACE-WISE CONFIDENCE SCORE 608(l), BASED ON HOW WELL OR HOW POORLY AN INTENSITY GRADIENT OF THE PHYSIOLOGICAL SURFACE 1404 FITS WITHIN A DISTRIBUTION FORMED BY THE INTENSITY GRADIENTS OF THE SET OF PHYSIOLOGICAL SURFACES 1410

EXPLAINABLE CONFIDENCE ESTIMATION FOR LANDMARK LOCALIZATION

TECHNICAL FIELD

The subject disclosure relates generally to landmark localization, and more specifically to explainable confidence estimation for landmark localization.

BACKGROUND

A medical imaging scanner can capture a three-dimensional voxel array that depicts some anatomy of a medical patient. A deep learning neural network can be trained to localize anatomical landmarks in the three-dimensional voxel array. After being trained, the deep learning neural network can be deployed in the field, so as to localize anatomical landmarks for inputted three-dimensional voxel arrays that lack ground-truth annotations. When the deep learning neural network localizes anatomical landmarks in the field, it can often be desirable to determine respective levels of confidence associated with such anatomical landmark localizations. Unfortunately, existing techniques for estimating confidence levels of anatomical landmark localizations require rigid architectural restrictions of the deep learning neural network, specialized training protocols for the deep learning neural network, or excessive computational complexity. Moreover, such existing techniques provide no insight, interpretability, or explainability with respect to the confidence levels they compute.

Accordingly, systems or techniques that can facilitate improved uncertainty estimation for anatomical landmark localization can be desirable.

SUMMARY

The following presents a summary to provide a basic understanding of one or more embodiments. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus or computer program products that facilitate explainable confidence estimation for landmark localization are described.

According to one or more embodiments, a system is provided. The system can comprise a non-transitory computer-readable memory that can store computer-executable components. The system can further comprise a processor that can be operably coupled to the non-transitory computer-readable memory and that can execute the computer-executable components stored in the non-transitory computer-readable memory. In various embodiments, the computer-executable components can comprise an access component that can access a three-dimensional voxel array captured by a medical imaging scanner. In various aspects, the computer-executable components can comprise an execution component that can localize, via execution of a first deep learning neural network, a set of anatomical landmarks depicted in the three-dimensional voxel array. In various instances, the computer-executable components can comprise a confidence component that can generate a multi-tiered confidence score collection based on the set of anatomical landmarks and based on a training dataset on which the first deep learning neural network was trained. In various cases, the computer-executable components can comprise a classifier component that, in response to one or more confidence scores from the multi-tiered confidence score collection failing to satisfy a threshold, can generate, via execution of a second deep learning neural network, a classification label for the one or more confidence scores, wherein the classification label can indicate an explanatory factor for why the one or more confidence scores failed to satisfy the threshold.

According to one or more embodiments, a computer-implemented method is provided. In various embodiments, the computer-implemented method can comprise accessing, by a device operatively coupled to a processor, a three-dimensional voxel array captured by a medical imaging scanner. In various aspects, the computer-implemented method can comprise localizing, by the device and via execution of a first deep learning neural network, a set of anatomical landmarks depicted in the three-dimensional voxel array. In various instances, the computer-implemented method can comprise generating, by the device, a multi-tiered confidence score collection based on the set of anatomical landmarks and based on a localization training dataset on which the first deep learning neural network was trained. In various cases, the computer-implemented method can comprise generating, by the device, in response to one or more confidence scores from the multi-tiered confidence score collection failing to satisfy a threshold, and via execution of a second deep learning neural network, a classification label for the one or more confidence scores, wherein the classification label can indicate an explanatory factor for why the one or more confidence scores failed to satisfy the threshold.

According to one or more embodiments, a computer program product for facilitating explainable confidence estimation for landmark localization is provided. In various embodiments, the computer program product can comprise a non-transitory computer-readable memory having program instructions embodied therewith. In various aspects, the program instructions can be executable by a processor to cause the processor to access a three-dimensional voxel array. In various instances, the program instructions can be executable by a processor to cause the processor to localize, via execution of a first deep learning neural network, a set of landmarks depicted in the three-dimensional voxel array. In various cases, the program instructions can be executable by a processor to cause the processor to generate a multi-tiered confidence score collection based on the set of landmarks and based on a localization training dataset on which the first deep learning neural network was trained. In various aspects, the program instructions can be executable by a processor to cause the processor to generate in response to one or more confidence scores from the multi-tiered confidence score collection failing to satisfy a threshold, and via execution of a second deep learning neural network, a classification label for the one or more confidence scores, wherein the classification label can indicate an explanatory factor for why the one or more confidence scores failed to satisfy the threshold.

DETAILED DESCRIPTION

Figure 1:
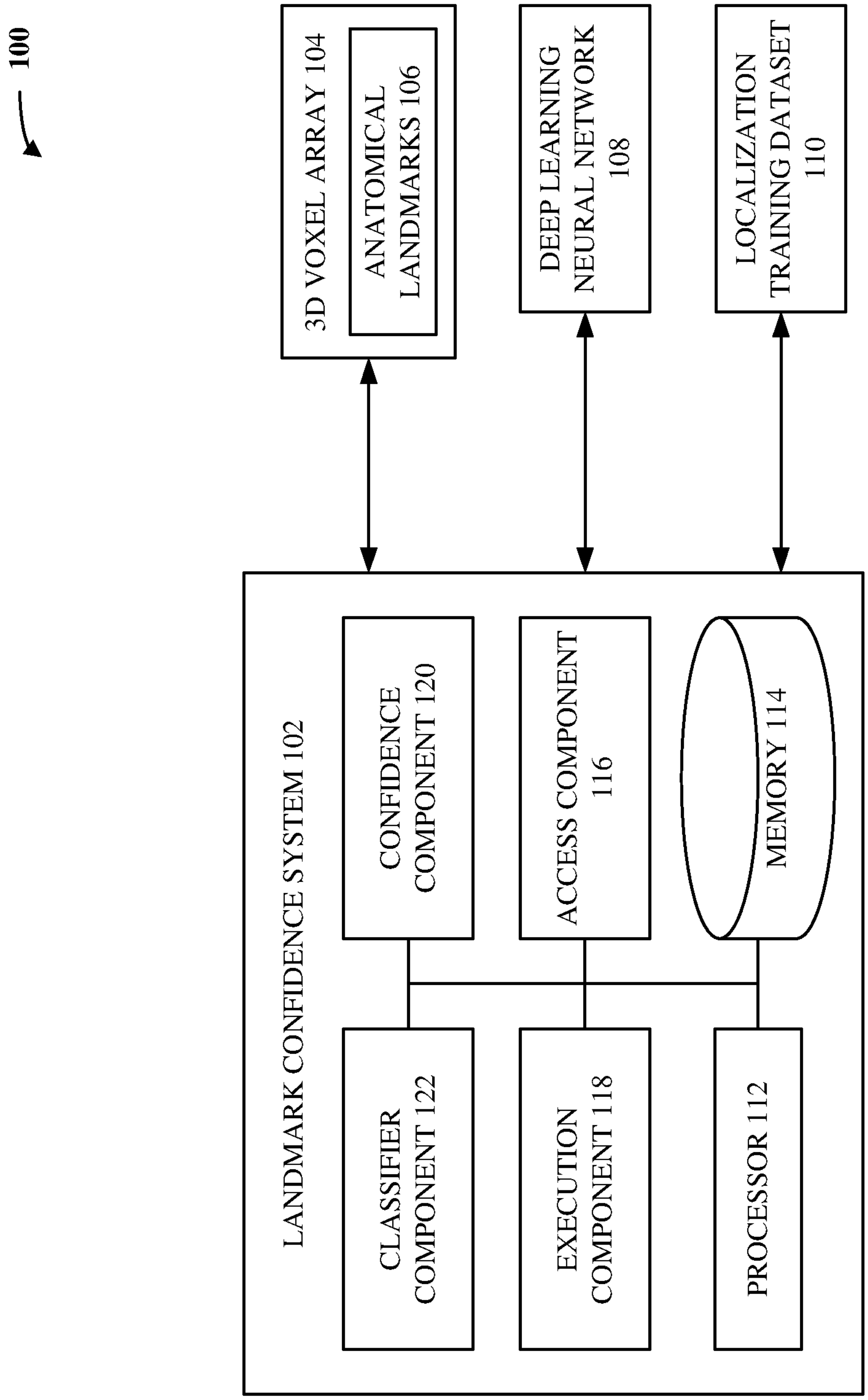
FIG. 1 illustrates a block diagram of an example, non-limiting system that facilitates explainable confidence estimation for landmark localization in accordance with one or more embodiments described herein.

The following detailed description is merely illustrative and is not intended to limit embodiments or application/uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

A medical imaging scanner (e.g., a computed tomography (CT) scanner, a magnetic resonance imaging (MRI) scanner, an X-ray scanner, an ultrasound scanner, a positron emission tomography (PET) scanner) can capture a three-dimensional voxel array that depicts any suitable anatomy (e.g., tissue, organ, or any other suitable body part or portion thereof) of a medical patient. A deep learning neural network can be trained (e.g., in supervised fashion) to localize, via bounding box generation, anatomical landmarks (e.g., any suitable biologically-meaningful loci) that are depicted in the three-dimensional voxel array. After being trained, the deep learning neural network can be deployed in the field, so as to localize anatomical landmarks depicted in inputted three-dimensional voxel arrays that lack ground-truth annotations.

When the deep learning neural network predicts bounding boxes for anatomical landmarks in the field, it can often be desirable to compute respective confidence scores for those bounding boxes. Indeed, in some cases, such confidence scores can be required by regulatory entities, in view of the fact that localization accuracy can be expected to decrease when the voxel arrays on which the deep learning neural network is being inferenced are different in some respect from the voxel arrays on which the deep learning neural network was trained (e.g., different demographics or feature distributions represented in the voxel arrays, different acquisition protocols used to generate or capture the voxel arrays). Furthermore, the bounding boxes predicted for those anatomical landmarks can be used in downstream inferencing tasks (e.g., orientation correction, surgical planning), and such downstream inferencing tasks can be negatively affected by bounding boxes with insufficiently high confidence.

Unfortunately, existing techniques for estimating confidence scores for bounding boxes that localize anatomical landmarks require rigid architectural restrictions of the deep learning neural network, specialized training protocols for the deep learning neural network, or excessive computational complexity.

For instance, Markov Chain Monte Carlo (MCMC) dropout techniques generate confidence maps for a deep learning neural network by dropping out, during inference, different layers or different neurons of the deep learning neural network. Although MCMC dropout can accurately or precisely measure confidence, it is applicable only to specially structured deep learning neural networks. Specifically, in order for MCMC dropout to be applied to a given deep learning neural network, the given deep learning neural network must first be configured to have dropout layers or dropout neurons in the absence of which the given deep learning neural network can still function or operate. Indeed, if a non-dropout layer or a non-dropout neuron of the given deep learning neural network were dropped out, the given deep learning neural network would simply cease to function or operate. Accordingly, MCMC dropout can be implemented only on specialized network architectures (e.g., only on deep learning neural network that are built or designed with dropout layers or dropout neurons) and thus is not a universal or generalizable technique (e.g., most deep learning neural networks are not built or designed with dropout layers or dropout neurons).

In other cases, Stochastic Weight Averaging (SWAG) techniques quantify confidence by iteratively calculating means and covariance matrices of internal parameters during training. Although SWAG techniques can accurately measure confidence of a particular deep learning neural network, such techniques require specialized computations to be performed during training of the particular deep learning neural network (e.g., require the means and covariance matrices of the internal parameters of the particular deep learning neural network to be iteratively tracked through each training epoch). In other words, if a deep learning neural network is trained without such specialized computations, then SWAG cannot be applied to that deep learning neural network. Thus, SWAG techniques are not universal or generalizable (e.g., during training of most deep learning neural networks, means and covariance matrices of internal parameter distributions are not tracked or recorded).

In even other cases, Deep Ensemble techniques quantify confidence by separately training multiple versions of a particular deep learning neural network, each of which beginning with a different random initialization. That is, multiple copies of a deep learning neural network can be created, the internal parameters of such multiple copies can each be differently randomly initialized, each of such multiple copies can be separately or independently trained, each of such separately or independently trained networks can be executed on a same inputted voxel array, and the degree of agreement or disagreement among such separately or independently trained networks can indicate how confidently the networks can analyze the inputted voxel array. Although Deep Ensemble techniques do not rely upon specific network architectures or specific training protocols, they are extremely computationally expensive. Indeed, fully training one deep learning neural network can be considered as time-consuming or resource-intensive. Thus, fully training, in separate or independent fashion, tens, dozens, or even hundreds of deep learning neural networks can be considered as extremely or excessively time-consuming and resource-intensive.

Moreover, such existing techniques (e.g., MCMC dropout, SWAG techniques, Deep Ensemble techniques) provide no insight, interpretability, or explainability with respect to the confidence scores that they compute. For instance, suppose that such existing techniques estimate a particular confidence score for a particular bounding box predicted by a deep learning neural network, and suppose that such particular confidence score fails to satisfy a threshold. That particular confidence score can thus be considered as indicating that the deep learning neural network predicted the particular bounding box with insufficient certainty. However, nothing in such existing techniques offers any interpretable indication regarding why the deep learning neural network predicted the particular bounding box with insufficient certainty. In other words, such existing techniques can be considered as black-box confidence calculators that compute confidence scores but that do not offer any transparency or explanation regarding why some of such computed confidence scores might be lower than others.

Accordingly, systems or techniques that can address one or more of these technical problems can be desirable.

Various embodiments described herein can address one or more of these technical problems. One or more embodiments described herein can include systems, computer-implemented methods, apparatus, or computer program products that can facilitate explainable confidence estimation for landmark localization. In other words, the inventors of various embodiments described herein devised a technique for calculating confidence scores of bounding boxes predicted by a deep learning neural network for respective anatomical landmarks, where such technique does not suffer from the same disadvantages as existing techniques. In still other words, the present inventors devised a way of computing confidence scores for anatomical landmark bounding boxes that does not involve the rigid architectural restrictions, the specialized training protocols, the excessive computational complexity, or the absence of explainability that plague existing techniques.

In particular, when given a set of anatomical landmarks depicted in a voxel array and for which a deep learning neural network has predicted respective bounding boxes, various embodiments described herein can involve computing a multi-tiered collection of confidence scores, where the multi-tiered collection can be computed based on those bounding boxes and based on whatever training dataset on which the deep learning neural network was trained. In various aspects, a first tier of the multi-tiered collection can include landmark-wise confidence scores (e.g., the deep learning neural network can have predicted a distinct bounding box per distinct anatomical landmark, and the multi-tiered collection can include a distinct confidence score per distinct bounding box). In various instances, a second tier of the multi-tiered collection can include pair-wise confidence scores (e.g., the deep learning neural network can have predicted a distinct bounding box per distinct anatomical landmark, but some of those anatomical landmarks can be considered as being members of anatomically symmetric landmark pairs; thus, the multi-tiered collection can include a distinct confidence score per distinct anatomically symmetric landmark pair). In various cases, a third tier of the multi-tiered collection can include group-wise confidence scores (e.g., the deep learning neural network can have predicted a distinct bounding box per distinct anatomical landmark, but some of those anatomical landmarks can be considered as being members of anthropometrically-meaningful landmark groups; thus, the multi-tiered collection can include a distinct confidence score per distinct anthropometrically-meaningful landmark group). In various aspects, a fourth tier of the multi-tiered collection can include surface-wise confidence scores (e.g., the deep learning neural network can have predicted a distinct bounding box per distinct anatomical landmark, but some of those anatomical landmarks can be considered as being members of physiological-surface-defining landmark groups; thus, the multi-tiered collection can include a distinct confidence score per distinct physiological-surface-defining landmark group).

In any case, as described herein, the multi-tiered collection of confidence scores can be computed regardless of the internal architecture of the deep learning neural network (e.g., unlike MCMC dropout techniques), regardless of which training procedures were used to train the deep learning neural network (e.g., unlike SWAG techniques), and without independently training multiple copies of the deep learning neural network (e.g., unlike Deep Ensemble techniques). Furthermore, various embodiments described herein can also include implementing a deep learning classifier that can increase explainability of the multi-tiered collection of confidence scores. Indeed, as described herein, whenever one or more confidence scores of the multi-tiered collection fail to satisfy any suitable threshold, the deep learning classifier can be executed on the voxel array and on those one or more confidence scores, so as to explicitly determine a substantive factor or reason explaining why such one or more confidence scores fail to satisfy the threshold.

Various embodiments described herein can be considered as a computerized tool (e.g., any suitable combination of computer-executable hardware or computer-executable software) that can facilitate explainable confidence estimation for landmark localization. In various aspects, such computerized tool can comprise an access component, an execution component, a confidence component, or a classifier component.

In various embodiments, there can be a given voxel array. In various aspects, the given voxel array can have any suitable number or arrangement of voxels. In various instances, the given voxel array can visually depict any suitable anatomy of a medical patient, and such anatomy can comprise any suitable number of anatomical landmarks. In various cases, the given voxel array can be captured or generated by any suitable medical imaging equipment (e.g., CT scanner, MRI scanner, X-ray scanner, ultrasound scanner, PET scanner).

In various embodiments, there can be a first deep learning neural network. In various aspects, the first deep learning neural network can exhibit any suitable deep learning internal architecture. For example, the first deep learning neural network can include any suitable numbers of any suitable types of layers (e.g., input layer, one or more hidden layers, output layer, any of which can be convolutional layers, dense layers, non-linearity layers, pooling layers, batch normalization layers, or padding layers). As another example, the first deep learning neural network can include any suitable numbers of neurons in various layers (e.g., different layers can have the same or different numbers of neurons as each other). As yet another example, the first deep learning neural network can include any suitable activation functions (e.g., softmax, sigmoid, hyperbolic tangent, rectified linear unit) in various neurons (e.g., different neurons can have the same or different activation functions as each other). As still another example, the first deep learning neural network can include any suitable interneuron connections or interlayer connections (e.g., forward connections, skip connections, recurrent connections).

Regardless of its internal architecture, the first deep learning neural network can be configured to localize, within any inputted voxel array, the anatomical landmarks. In particular, the first deep learning neural network can be configured to receive as input some voxel array and to produce as output bounding boxes, where each bounding box can indicate where within that inputted voxel array a respective anatomical landmark is located.

In various embodiments, the first deep learning neural network can have been trained in supervised fashion on a first training dataset to perform such landmark localization. In various aspects, the first training dataset can comprise any suitable number of training voxel arrays, each of which can depict the anatomical landmarks in an anatomy of a respective medical patient. In various instances, for each training voxel array, the first training dataset can comprise a respective set of ground-truth bounding boxes, which can indicate where the anatomical landmarks are known or deemed to be located within that training voxel array.

In various aspects, it can be desired to execute the first deep learning neural network on the given voxel array, so as to determine where the anatomical landmarks are located within the given voxel array. Furthermore, it can be desired to estimate confidence scores for such localization. As described herein, the computerized tool can facilitate such confidence score estimation, based on the first training dataset.

In various embodiments, the access component of the computerized tool can electronically receive or otherwise electronically access the given voxel array, the first deep learning neural network, or the first training dataset. In some aspects, the access component can electronically retrieve the given voxel array, the first deep learning neural network, or the first training dataset from any suitable centralized or decentralized data structures (e.g., graph data structures, relational data structures, hybrid data structures), whether remote from or local to the access component. In any case, the access component can electronically obtain or access the given voxel array, the first deep learning neural network, or the first training dataset, such that other components of the computerized tool can electronically interact with (e.g., read, write, edit, copy, manipulate) the given voxel array, with the first deep learning neural network, or with the first training dataset.

In various embodiments, the execution component of the computerized tool can electronically localize the anatomical landmarks within the given voxel array, by executing the first deep learning neural network on the given voxel array. More specifically, the execution component can feed the given voxel array to an input layer of the first deep learning neural network, the given voxel array can complete a forward pass through one or more hidden layers of the first deep learning neural network, and an output layer of the first deep learning neural network can compute a respective bounding box for each of the anatomical landmarks, based on activations from the one or more hidden layers of the first deep learning neural network.

For any particular anatomical landmark, the bounding box produced by the first deep learning neural network for that particular anatomical landmark can be considered as indicating the three-space location within the given voxel array at which the first deep learning neural network has inferred the particular anatomical landmark to be located. In other words, the bounding box can be considered as indicating which voxels in the given voxel array make up or otherwise belong to the particular anatomical landmark.

In various embodiments, the confidence component of the computerized tool can electronically compute a multi-tiered collection of confidence scores, based on the bounding boxes predicted by the first deep learning neural network, and based on the ground-truth bounding boxes in the first training dataset. In various aspects, the multi-tiered collection can include various different tiers of confidence scores (hence the term "multi-tiered"), where each tier can be considered as a unique type or class of confidence score that can capture a respective aspect or feature of the bounding boxes predicted by the first deep learning neural network. Indeed, in various instances, a first tier of the multi-tiered collection can be landmark-wise confidence scores, a second tier of the multi-tiered collection can be pair-wise confidence scores, a third tier of the multi-tiered collection can be group-wise confidence scores, and a fourth tier of the multi-tiered collection can be surface-wise confidence scores.

In various aspects, as mentioned above, the first deep learning neural network can localize, via bounding box prediction, each anatomical landmark in the given voxel array. In various instances, a landmark-wise confidence score can be any suitable scalar whose magnitude indicates or represents a level of localization confidence with respect to any single one of the anatomical landmarks (hence the term "landmark-wise"). In various cases, the confidence component can compute a landmark-wise confidence score for an anatomical landmark by comparing the bounding box predicted by the first deep learning neural network for that anatomical landmark to whatever ground-truth bounding boxes in the first training dataset also correspond to that anatomical landmark.

For instance, suppose that the first deep learning neural network has predicted a specific bounding box for an anatomical landmark A. That is, the specific bounding box can indicate an approximate three-dimensional location within the given voxel array at which the anatomical landmark A is inferred to be located. Now, other instantiations of the anatomical landmark A (e.g., such instantiations can belong to different medical patients) can be depicted in the training voxel arrays of the first training dataset. So, the first training dataset can contain ground-truth bounding boxes that respectively indicate where those other instantiations of the anatomical landmark A are known or deemed to be located within the training voxel arrays. Thus, the anatomical landmark A can be considered as corresponding not just to the specific bounding box predicted by the first deep learning neural network, but also to multiple ground-truth bounding boxes in the first training dataset. In various cases, the confidence component can compute a landmark-wise confidence score for the anatomical landmark A, by comparing any suitable attribute (e.g., volume, length, width, height, intensity gradient, intensity average, any other suitable intensity attribute) exhibited by that specific bounding box to a corresponding attribute distribution (e.g., distribution of volumes, distribution of lengths, distribution of widths, distributions of heights, distribution of intensity gradients, distribution of intensity averages, distribution of intensity attributes) collectively exhibited by those multiple ground-truth bounding boxes. For instance, the landmark-wise confidence score for the anatomical landmark A can be equal to or otherwise based on a probability or measure of fit between the attribute of that specific bounding box and the attribute distribution of those multiple ground-truth bounding boxes. Accordingly, if the attribute of the specific bounding box fits nicely (e.g., with high probability) into the attribute distribution of those multiple ground-truth bounding boxes, then the magnitude of the landmark-wise confidence score for the anatomical landmark A can be higher, indicating that the first deep learning neural network confidently localized the anatomical landmark A in the given voxel array. On the other hand, if the attribute of the specific bounding box fits poorly (e.g., with low probability) into the attribute distribution of those multiple ground-truth bounding boxes, then the magnitude of the landmark-wise confidence score for the anatomical landmark A can be lower, indicating that the first deep learning neural network unconfidently localized the anatomical landmark A in the given voxel array.

In various aspects, as mentioned above, the first deep learning neural network can localize, via bounding box prediction, each anatomical landmark in the given voxel array. However, various pairs of those anatomical landmarks can be considered or expected to be anatomically symmetrical to each other. In various instances, a pair-wise confidence score can be any suitable scalar whose magnitude indicates or represents a level of localization confidence with respect to any anatomically symmetric pair of anatomical landmarks (hence the term "pair-wise"). In various cases, the confidence component can compute a pair-wise confidence score for an anatomically symmetric pair of anatomical landmarks based on the landmark-wise confidence scores for that anatomically symmetric pair of anatomical landmarks.

For instance, suppose that an anatomical landmark B and an anatomical landmark C respectively represent biological loci that are expected to be anatomically or physiologically symmetric with respect to each other. For example, the anatomical landmark B can be a left eye of a medical patient, and the anatomical landmark C can be a right eye of the medical patient (e.g., left and right eyes can be expected to be physically symmetric to each other). As another example, the anatomical landmark B can be a proximal end of a long bone (e.g., a shafted bone that is longer than it is wide) of a medical patient, and the anatomical landmark C can be a distal end of the long bone of the medical patient (e.g., proximal and distal ends of certain long bones, such as tarsals, can be expected to be physically symmetric to each other). In any case, the confidence component can have computed a landmark-wise confidence score for the anatomical landmark B and a landmark-wise confidence score for the anatomical landmark C, as described above, and the confidence component can compute a pair-wise confidence score for the anatomically symmetric pair formed by the anatomical landmark B and the anatomical landmark C, based on those two landmark-wise confidence scores. In particular, the pair-wise confidence score can be equal to or otherwise based on a multiplicative product or an absolute difference between those two landmark-wise confidence scores. Accordingly, if the anatomical landmark B and the anatomical landmark C have similar or matching landmark-wise confidence scores, then the magnitude of the pair-wise confidence score can be higher, indicating that the first deep learning neural network similarly or symmetrically localized the anatomically symmetric pair formed by the anatomical landmark B and the anatomical landmark C. On the other hand, if the anatomical landmark B and the anatomical landmark C have dissimilar or disparate landmark-wise confidence scores, then the magnitude of the pair-wise confidence score can be lower, indicating that the first deep learning neural network dissimilarly or asymmetrically localized the anatomically symmetric pair formed by the anatomical landmark B and the anatomical landmark C.

In various aspects, as mentioned above, the first deep learning neural network can localize, via bounding box prediction, each anatomical landmark in the given voxel array. However, various groups of those anatomical landmarks can be considered or expected to be anthropometrically related to each other. In various instances, a group-wise confidence score can be any suitable scalar whose magnitude indicates or represents a level of localization confidence with respect to any anthropometric group of anatomical landmarks (hence the term "group-wise"). In various cases, the confidence component can compute a group-wise confidence score for an anthropometric group of anatomical landmarks by comparing the bounding boxes predicted by the first deep learning neural network for that anthropometric group of anatomical landmarks to whatever ground-truth bounding boxes in the first training dataset also correspond to that anthropometric group of anatomical landmarks.

For instance, suppose that the anatomical landmark A, the anatomical landmark B, and the anatomical landmark C respectively represent biological loci that are considered as anthropometrically related (e.g., in terms of biologically-relevant geometric measurements) to each other. For example, the anatomical landmark A can be a nasion of a medical patient, the anatomical landmark B can be a left ear canal of the medical patient, and the anatomical landmark C can be a right ear canal of the medical patient (e.g., the nasion and two ear canals can be used for anthropometric benchmarking of the human body). In various aspects, the first deep learning neural network can have predicted a respective bounding box for each of the anatomical landmark A, the anatomical landmark B, and the anatomical landmark C, where those bounding boxes can respectively indicate approximate three-dimensional locations within the given voxel array at which the anatomical landmark A, the anatomical landmark B, and the anatomical landmark C are inferred to be located. Now, other instantiations of the anatomical landmark A, of the anatomical landmark B, and of the anatomical landmark C (e.g., such instantiations can belong to different medical patients) can be depicted in the training voxel arrays of the first training dataset. So, the first training dataset can contain ground-truth bounding boxes that respectively indicate where those other instantiations of the anatomical landmark A, of the anatomical landmark B, and of the anatomical landmark C are known or deemed to be located within the training voxel arrays. Thus, the anatomical landmark A, the anatomical landmark B, and the anatomical landmark C can be considered as corresponding not just to the bounding boxes predicted by the first deep learning neural network, but also to multiple ground-truth bounding boxes in the first training dataset.

In various cases, the confidence component can compute a group-wise confidence score for the anthropometric group formed by the anatomical landmark A, the anatomical landmark B, and the anatomical landmark C by comparing any suitable geometric interrelation exhibited by the predicted bounding boxes (e.g., any ratios of distances between A and B, between B and C, or between A and C; any ratios of angles subtended by A-B-C, by A-C-B, or by C-A-B) to a corresponding geometric interrelation distribution (e.g., distribution of separation distance ratios, distribution of subtended angle ratios) collectively exhibited by those multiple ground-truth bounding boxes. For instance, the group-wise confidence score can be equal to or otherwise based on a probability or measure of fit between the geometric interrelation exhibited by those predicted bounding boxes and the geometric interrelation distribution exhibited by those multiple ground-truth bounding boxes. Accordingly, if the geometric interrelation of those predicted bounding boxes fits nicely (e.g., with high probability) into the geometric interrelation distribution of those multiple ground-truth bounding boxes, then the magnitude of the group-wise confidence score can be higher, indicating that the first deep learning neural network confidently localized the anthropometric group containing the anatomical landmark A, the anatomical landmark B, and the anatomical landmark C in the given voxel array. On the other hand, if the geometric interrelation of those predicted bounding boxes fits poorly (e.g., with low probability) into the geometric interrelation distribution of those multiple ground-truth bounding boxes, then the magnitude of the group-wise confidence score can be lower, indicating that the first deep learning neural network unconfidently localized the anthropometric group containing the anatomical landmark A, the anatomical landmark B, and the anatomical landmark C in the given voxel array.

Note that the group-wise confidence score can be low, notwithstanding that the landmark-wise confidence scores of the anatomical landmark A, of the anatomical landmark B, and of the anatomical landmark C can be high (e.g., each of A, B, and C can have been individually confidently localized, but the ratios of distances separating such localizations or of the angles subtended by such localizations can be outside of whatever distributions are exhibited by the first training dataset, which can cut against individually confident localization).

In various aspects, as mentioned above, the first deep learning neural network can localize, via bounding box prediction, each anatomical landmark in the given voxel array. However, various groups of those anatomical landmarks can be considered as collectively defining, delineating, or demarcating physiological surfaces. In various instances, a surface-wise confidence score can be any suitable scalar whose magnitude indicates or represents a level of localization confidence with respect to any surface-defining group of anatomical landmarks (hence the term "surface-wise"). In various cases, the confidence component can compute a surface-wise confidence score for a surface-defining group of anatomical landmarks by comparing the bounding boxes predicted by the first deep learning neural network for that surface-defining group of anatomical landmarks to whatever ground-truth bounding boxes in the first training dataset also correspond to that surface-defining group of anatomical landmarks.

For instance, suppose that the anatomical landmark A, the anatomical landmark B, and the anatomical landmark C respectively represent biological loci that are expected, known, or supposed to collectively define some physiological surface. For example, the anatomical landmark A, the anatomical landmark B, and the anatomical landmark C can be distinct points residing on a skull of a medical patient. In such case, the anatomical landmark A, the anatomical landmark B, and the anatomical landmark C can be considered as defining, delineating, or demarcating a cranial surface of the medical patient. As another example, the anatomical landmark A, the anatomical landmark B, and the anatomical landmark C can be distinct points residing on a femur shaft of the medical patient. In such case, the anatomical landmark A, the anatomical landmark B, and the anatomical landmark C can be considered as defining, delineating, or demarcating a femur shaft surface of the medical patient. As even another example, the anatomical landmark A, the anatomical landmark B, and the anatomical landmark C can be distinct points residing at a given axial level of the medical patient. In such case, the anatomical landmark A, the anatomical landmark B, and the anatomical landmark C can be considered as defining, delineating, or demarcating an axial plane of the medical patient. In any case, as mentioned above, the anatomical landmark A, the anatomical landmark B, and the anatomical landmark C can be considered as corresponding not just to the bounding boxes predicted by the first deep learning neural network, but also to multiple ground-truth bounding boxes in the first training dataset.

In various cases, the confidence component can compute a surface-wise confidence score for the surface-defining group formed by the anatomical landmark A, the anatomical landmark B, and the anatomical landmark C, by comparing any suitable feature (e.g., intensity gradient) exhibited by whatever physiological surface is actually demarcated by the predicted bounding boxes to a corresponding feature distribution (e.g., distribution of intensity gradients) collectively exhibited whatever physiological surfaces are actually demarcated by those multiple ground-truth bounding boxes. For instance, the surface-wise confidence score can be equal to or otherwise based on a probability or measure of fit between the feature exhibited by the physiological surface demarcated by the predicted bounding boxes and the feature distribution exhibited by the physiological surfaces demarcated by those multiple ground-truth bounding boxes. Accordingly, if the feature exhibited by the physiological surface demarcated by those predicted bounding boxes fits nicely (e.g., with high probability) into the feature distribution of the physiological surfaces demarcated by those multiple ground-truth bounding boxes, then the magnitude of the surface-wise confidence score can be higher, indicating that the first deep learning neural network confidently localized the surface-defining group containing the anatomical landmark A, the anatomical landmark B, and the anatomical landmark C in the given voxel array. On the other hand, if the feature exhibited by the physiological surface demarcated by those predicted bounding boxes fits poorly (e.g., with low probability) into the feature distribution of the physiological surfaces demarcated by those multiple ground-truth bounding boxes, then the magnitude of the surface-wise confidence score can be lower, indicating that the first deep learning neural network unconfidently localized the surface-defining group containing the anatomical landmark A, the anatomical landmark B, and the anatomical landmark C in the given voxel array.

Note that the surface-wise confidence score can be low, notwithstanding that the landmark-wise confidence scores of the anatomical landmark A, of the anatomical landmark B, and of the anatomical landmark C can be high (e.g., each of A, B, and C can have been individually confidently localized, but the intensity gradient of the surface delineated by such localizations can be outside of whatever intensity gradient distribution is exhibited by the first training dataset, which can cut against individually confident localization).

In any case, the confidence component can electronically generate the multi-tiered collection of confidence scores, based on the bounding boxes predicted by the first deep learning neural network, and based on the first training dataset. As described herein, the different tiers of confidence scores (e.g., landmark-wise tier, pair-wise tier, group-wise tier, surface-wise tier) can be considered as capturing different aspects of localization confidence of the first deep learning neural network. Indeed, the landmark-wise tier can capture individual confidence of each predicted bounding box. Moreover, the pair-wise tier can capture confidence for pairs of predicted bounding boxes that are expected or supposed to be physically symmetric to each other (e.g., a pair-wise confidence score for an anatomical landmark can be low, notwithstanding that the landmark-wise confidence score for that anatomical landmark might be high). Furthermore, the group-wise tier can capture confidence for groups of predicted bounding boxes that are expected or supposed to traverse or subtend anthropometric distances or angles that form stable (e.g., not highly varying) ratios (e.g., a group-wise confidence score for an anatomical landmark can be low, notwithstanding that the landmark-wise confidence score for that anatomical landmark or a pair-wise confidence score (if any) for that anatomical landmark might be high). Further still, the surface-wise tier can capture confidence for groups of predicted bounding boxes that are expected to define or demarcate biologically-relevant surfaces (e.g., a surface-wise confidence score for an anatomical landmark can be low, notwithstanding that the landmark-wise confidence score for that anatomical landmark or a pair-wise or group-wise confidence score (if any) for that anatomical landmark might be high).

Note that the multi-tiered collection of confidence scores can be computed, no matter the internal architecture of the first deep learning neural network, no matter how the first deep learning neural network was trained, and without implementing an ensemble for the first deep learning neural network.

In various embodiments, the classifier component of the computerized tool can electronically determine whether one or more confidence scores from the multi-tiered collection of confidence scores fail to satisfy any suitable threshold value. If no confidence scores from the multi-tiered collection fail to satisfy the threshold value, the classification component can permit or recommend that the bounding boxes predicted by the first deep learning neural network be utilized for any suitable downstream inferencing tasks (e.g., orientation correction, surgical planning). However, if one or more confidence scores from the multi-tiered collection fail to satisfy the threshold value, then the classifier component can prevent or recommend against the bounding boxes (or a portion thereof) predicted by the first deep learning neural network being utilized for those downstream inferencing tasks. Furthermore, if one or more confidence scores from the multi-tiered collection fail to satisfy the threshold value, the classifier component can, in various cases, electronically determine a substantive reason or explanation for why the one or more confidence scores failed to satisfy the threshold value. In various instances, the classifier component can facilitate such determination via a second deep learning neural network.

In particular, the classifier component can electronically store, maintain, control, or otherwise access the second deep learning neural network. In various aspects, the second deep learning neural network can exhibit any suitable deep learning internal architecture. For example, the second deep learning neural network can include any suitable numbers of any suitable types of layers (e.g., input layer, one or more hidden layers, output layer, any of which can be convolutional layers, dense layers, non-linearity layers, pooling layers, batch normalization layers, or padding layers). As another example, the second deep learning neural network can include any suitable numbers of neurons in various layers (e.g., different layers can have the same or different numbers of neurons as each other). As yet another example, the second deep learning neural network can include any suitable activation functions (e.g., softmax, sigmoid, hyperbolic tangent, rectified linear unit) in various neurons (e.g., different neurons can have the same or different activation functions as each other). As still another example, the second deep learning neural network can include any suitable interneuron connections or interlayer connections (e.g., forward connections, skip connections, recurrent connections).

Regardless of its internal architecture, the second deep learning neural network can be configured as a classifier that operates on inputted voxel arrays and corresponding confidence scores. Accordingly, the classifier component can, in various aspects, electronically generate an explanatory classification label, by executing the second deep learning neural network on the given voxel array and on the multi-tiered collection of confidence scores (or a portion thereof). More specifically, the classifier component can feed the given voxel array and the multi-tiered collection of confidences scores (or a portion thereof) to an input layer of the second deep learning neural network, the given voxel array and the multi-tiered collection of confidences scores (or the portion thereof) can complete a forward pass through one or more hidden layers of the second deep learning neural network, and an output layer of the second deep learning neural network can compute the explanatory classification label based on activations from the one or more hidden layers of the second deep learning neural network.

In any case, the explanatory classification label can indicate, convey, or otherwise identify one or more factors that can explain why some of the multi-tiered collection failed to satisfy the threshold value. Non-limiting examples of such factors can be the presence of imaging artifacts or acquisition artifacts (e.g., depictions or distortions caused by surgical hardware, lens scratches, lens glares, or intra-scan patient motion such as fidgeting or breathing) in the given voxel array, the presence of anatomical pathologies (e.g., depictions of disease symptoms or injury symptoms) in the given voxel array, an improper or unexpected field of view (e.g., too zoomed in, too zoomed out) of the given voxel array, an improper or unexpected radiation dosage (e.g., captured via too little radiation, captured via too much radiation) of the given voxel array, an improper or unexpected anatomy of the given voxel array (e.g., trying to localize cranial landmarks based on an a foot X-ray image), or any other unusual or non-standard characteristic or attribute exhibited by the given voxel array.

In various aspects, the computerized tool can electronically render on any suitable electronic display, or can electronically transmit to any suitable computing device, the predicted bounding boxes or any of the multi-tiered collection of confidence scores. Accordingly, a user, operator, or technician associated with the computerized tool can become apprised of how confidently or unconfidently the first deep learning neural network localized the anatomical landmarks within the given voxel array. Moreover, in various instances, the computerized tool can electronically render on any suitable electronic display or can electronically transmit to any suitable computing device the explanatory classification label. Thus, the user, operator, or technician can become apprised of whatever reason or explanation potentially caused the first deep learning neural network to unconfidently localize some of the anatomical landmarks within the given voxel array.

In order to help ensure that the explanatory classification label is accurate or reliable, the second deep learning neural network can undergo any suitable type or paradigm of training. Accordingly, the computerized tool can comprise a training component that can train the second deep learning neural network in any suitable fashion on a second training dataset. As a non-limiting example, the second training dataset can be annotated, and the training component can thus facilitate supervised training of the second deep learning neural network.

In any case, the computerized tool described herein can estimate confidence for anatomical landmark localizations predicted by the first deep learning neural network, without requiring the first deep learning neural network to have a specialized internal architecture (e.g., unlike MCMC dropout techniques), without requiring the first deep learning neural network to undergo specialized training protocols (e.g., unlike SWAG techniques), and without excessively consuming resources by ensembling the first deep learning neural network (e.g., unlike Deep Ensemble techniques). Furthermore, not only can the computerized tool described herein estimate confidence for such anatomical landmark localizations without being plagued by the shortcomings of existing techniques, but the computerized tool can also identify, via the second deep learning neural network, a factor or reason that explains why the confidence of any of such anatomical landmark localizations is insufficient.

Various embodiments described herein can be employed to use hardware or software to solve problems that are highly technical in nature (e.g., to facilitate explainable confidence estimation for landmark localization), that are not abstract and that cannot be performed as a set of mental acts by a human. Further, some of the processes performed can be performed by a specialized computer (e.g., deep learning neural networks having internal parameters such as convolutional kernels) for carrying out defined acts related to landmark localization.

For example, such defined acts can include: accessing, by a device operatively coupled to a processor, a three-dimensional voxel array captured by a medical imaging scanner; localizing, by the device and via execution of a first deep learning neural network, a set of anatomical landmarks depicted in the three-dimensional voxel array; generating, by the device, a multi-tiered confidence score collection based on the set of anatomical landmarks and based on a localization training dataset on which the first deep learning neural network was trained; and generating, by the device, in response to one or more confidence scores from the multi-tiered confidence score collection failing to satisfy a threshold, and via execution of a second deep learning neural network, a classification label that indicates an explanatory factor for why the one or more confidence scores failed to satisfy the threshold. In various cases, a first tier of the multi-tiered confidence score collection can comprise landmark-wise confidence scores respectively corresponding to individual ones of the set of anatomical landmarks, a second tier of the multi-tiered confidence score collection can comprise pair-wise confidence scores respectively corresponding to anatomically symmetric pairs of the set of anatomical landmarks, a third tier of the multi-tiered confidence score collection can comprise group-wise confidence scores respectively corresponding to anthropometric groups of the set of anatomical landmarks, and a fourth tier of the multi-tiered confidence score collection can comprise surface-wise confidence scores respectively corresponding to surface-defining groups of the set of anatomical landmarks.

Such defined acts are not performed manually by humans. Indeed, neither the human mind nor a human with pen and paper can electronically access a voxel array, electronically localize anatomical landmarks depicted in the voxel array by executing a deep learning neural network, electronically compute confidence scores according to multi-different tiers (e.g., landmark-wise tier, pair-wise tier, group-wise tier, surface-wise tier), and, in response to various confidence scores falling below a threshold, electronically generate, by executing another deep learning neural network, an explanatory classification label that indicates or explains a substantive reason why those various confidence scores fell below the threshold. Indeed, a deep learning neural network is an inherently-computerized construct that simply cannot be meaningfully executed or trained in any way by the human mind without computers. Furthermore, anatomical landmark localization is a computerized inferencing task in which computers automatically locate where anatomical landmarks are visually illustrated within inputted images. Thus, anatomical landmark localization is an inherently-computerized inferencing task that cannot be meaningfully implemented in any way by the human mind without computers. Further still, confidence estimation is an inherently-computerized accessory task in which computers automatically assign numeric confidence scores to the results predicted or inferred by deep learning neural networks. For at least these reasons, a computerized tool that can estimate confidence scores in multi-tiered fashion for anatomical landmark localization results and that can identify substantive factors or reasons that explain why some anatomical landmarks are localized unconfidently is likewise inherently-computerized and cannot be implemented in any sensible, practical, or reasonable way without computers.

Moreover, various embodiments described herein can integrate into a practical application various teachings relating to explainable confidence estimation for landmark localization. As explained above, existing techniques for facilitating confidence scoring suffer from various significant disadvantages. Specifically, some techniques (e.g., MCMC dropout) can be applied only to deep learning neural networks with very specific structures (e.g., only neural networks that have built-in dropout layers) and are thus not generalizable. Moreover, other techniques (e.g., SWAG techniques) can be applied only to deep learning neural networks that have been trained in a very specific fashion (e.g., where means or covariance matrices of internal parameters had been computed at each training epoch) and are thus also not generalizable. Furthermore, still other techniques (e.g., Deep Ensemble techniques) consume extremely many computational resources (e.g., require duplicative training, from scratch, of several randomly-initialized deep learning neural networks).

In stark contrast, various embodiments described herein can address these technical problems. Specifically, for bounding boxes predicted by a first deep learning neural network, various embodiments described herein can involve computing a multi-tiered collection of confidence scores, based on those bounding boxes and based on whatever training data on which the first deep learning neural network was trained. In particular, a first tier of such multi-tiered collection can include confidence scores that are computed on a landmark-wise basis, by comparing an attribute (e.g., volume, length, width, height, intensity gradient, intensity average, other intensity attribute) of each predicted bounding box to a respective attribute distribution exhibited by the ground-truth bounding boxes in the training data. Moreover, a second tier of such multi-tiered collection can include confidence scores that are computed on a pair-wise basis, by comparing the landmark-wise confidence scores for any anatomically symmetric pair of landmarks. Furthermore, a third tier of such multi-tiered collection can include confidence scores that are computed on a group-wise basis, by comparing a geometric interrelation (e.g., ratio of separation distances, ratio of subtended angles) between the predicted bounding boxes of any anthropometric group of landmarks with a respective geometric interrelation distribution exhibited by ground-truth bounding boxes in the training data. Further still, a fourth tier of such multi-tiered collection can include confidence scores that are computed on a surface-wise basis, by comparing a feature (e.g., intensity gradient) of a physiological surface demarcated by the predicted bounding boxes of any surface-defining group of landmarks with a respective feature distribution of physiological surfaces demarcated by ground-truth bounding boxes in the training data.

Note that, unlike MCMC dropout techniques, the multi-tiered collection of confidence scores can be computed no matter the internal architecture of the first deep learning neural network. Additionally, note that, unlike SWAG techniques, the multi-tiered collection of confidence scores can be computed no matter what specific training protocols the first deep learning neural network underwent. Also, note that, unlike Deep Ensemble techniques, the multi-tiered collection of confidence scores can be computed notwithstanding that the first deep learning neural network has not been ensembled.

Not only can various embodiments described herein involve computing the multi-tiered collection of confidence scores, but various embodiments can also involve determining, via execution of a second deep learning neural network, a factor, reason, or justification that explains why the first deep learning neural network might have unconfidently localized one or more anatomical landmarks. Accordingly, such embodiments can be considered as demonstrating heightened explainability as compared to existing techniques. Indeed, each of MCMC dropout techniques, SWAG techniques, and Deep Ensemble techniques can be considered as black-boxes that offer no interpretability or transparency to help explain why some confidence scores might be lower than others. In stark contrast, various embodiments described herein can explicitly provide explanatory classification labels that identify explanations or reasons for low confidence scores (e.g., due to depicted imaging artifacts, due to depicted pathologies, due to improper field of view, due to improper anatomy). Such heightened explainability or interpretability constitutes another advantage of various embodiments described herein over existing techniques. Indeed, explainable artificial intelligence is a burgeoning area of research and development which seeks to reduce the black-box opaqueness that normally accompanies deep learning.

Moreover, note that the implementation of multi-tiered confidence scores as described herein can be considered as boosting, buttressing, or otherwise improving the explainability of various embodiments described herein. Indeed, each different tier of confidence score described herein can be considered as capturing or monitoring for a unique or distinct type of localization failure, and so the combination of such different tiers can be considered as more fully able to reflect localization confidence than any one of those different tiers could accomplish alone.

As a non-limiting example, consider a particular landmark. Suppose that a landmark-wise confidence score for that particular landmark fails to satisfy a threshold. In such case, it can be concluded that the predicted bounding box for that particular landmark would be likely to cause inaccuracies in downstream inferencing tasks. However, suppose instead that the landmark-wise confidence score for that particular landmark satisfies the threshold. In such case, it can nevertheless be possible that the predicted bounding box of that particular landmark might still cause inaccuracies in the downstream inferencing tasks. Although such possibilities are not reflected by the landmark-wise confidence score, they can be reflected by other tiers of confidence scores.

For instance, the particular landmark can have a high landmark-wise confidence score but a low pair-wise confidence score. In such case, although the predicted bounding box of the particular landmark can be considered as individually confident, that predicted bounding box can be unexpectedly or uncharacteristically unsymmetrical to that of some other landmark to which the particular landmark is paired. Thus, it can be concluded that the predicted bounding box of that particular landmark might still cause inaccuracies in the downstream inferencing tasks, notwithstanding the high landmark-wise confidence score.

As another instance, the particular landmark can have a high landmark-wise confidence score but a low group-wise confidence score. In such case, although the predicted bounding box of the particular landmark can be considered as individually confident, that predicted bounding box can be unexpectedly or uncharacteristically far away from, close to, or otherwise at strange angles to those of one or more other landmarks with which the particular landmark is grouped. Thus, it can be concluded that the predicted bounding box of that particular landmark might still cause inaccuracies in the downstream inferencing tasks, notwithstanding the high landmark-wise confidence score.

As even another instance, the particular landmark can have a high landmark-wise confidence score but a low surface-wise confidence score. In such case, although the predicted bounding box of the particular landmark can be considered as individually confident, that predicted bounding box can, when aggregated with those of one or more other landmarks with which the particular landmark is grouped, define or demarcate an unexpected, uncharacteristic, or strange physiological surface. Thus, it can be concluded that the predicted bounding box of that particular landmark might still cause inaccuracies in the downstream inferencing tasks, notwithstanding the high landmark-wise confidence score.

Accordingly, implementation of multi-tiered confidence scores can be considered as boosting or buttressing the accuracy or precision of the explanatory classification labels described herein. More generally, any given landmark can score highly in some confidence score tiers and lowly in other confidence score tiers, and such confidence scoring pattern can be considered as rich information that can help to identify which particular substantive reason most or best explains what, if anything, went wrong with the localization of that given landmark (e.g., a pathology failure can manifest as low pair-wise or group-wise confidence scores among otherwise high confidence scores; a too-zoomed-out field of view failure can manifest as low surface-wise confidence scores among otherwise high confidence scores; a too-zoomed-in field of view failure can manifest as some high and some low confidence scores across all tiers; a wrong anatomy failure can manifest as primarily low confidence scores at all tiers). Techniques which do not utilize multi-tiered confidence scores miss out on such improved explainability.

For at least these reasons, various embodiments described herein certainly constitute a tangible and concrete technical improvement in the field of anatomical landmark localization. Accordingly, such embodiments clearly qualify as useful and practical applications of computers.

Furthermore, various embodiments described herein can control real-world tangible devices based on the disclosed teachings. For example, various embodiments described herein can electronically train or execute real-world deep learning neural networks on real-world images (e.g., X-ray scanned images, CT scanned images), and can electronically render real-world landmark localization results (e.g., bounding boxes) on real-world computer screens.

It should be appreciated that the herein figures and description provide non-limiting examples of various embodiments and are not necessarily drawn to scale.

FIG. 1 illustrates a block diagram of an example, non-limiting system 100 that can facilitate explainable confidence estimation for landmark localization in accordance with one or more embodiments described herein. As shown, a landmark confidence system 102 can be electronically integrated, via any suitable wired or wireless electronic connections, with a 3D voxel array 104, with a deep learning neural network 108, or with a localization training dataset 110.

In various embodiments, the 3D voxel array 104 can be any suitable array of voxels (e.g., with each voxel having a respective Hounsfield unit value) that can exhibit any suitable format, size, or dimensionality. As a non-limiting example, the 3D voxel array 104 be an x-by-y-by-z array of voxels, for any suitable positive integers x, y, and z. In various aspects, the 3D voxel array 104 can be captured or otherwise generated by any suitable imaging device (not shown). As a non-limiting example, the 3D voxel array 104 can be captured or generated by a CT scanner, in which case the 3D voxel array 104 can be considered as a three-dimensional CT scanned image. As another non-limiting example, the 3D voxel array 104 can be captured or generated by an MRI scanner, in which case the 3D voxel array 104 can be considered as a three-dimensional MRI scanned image. As still another non-limiting example, the 3D voxel array 104 can be captured or generated by an X-ray scanner, in which case the 3D voxel array 104 can be considered as a three-dimensional X-ray scanned image. As yet another non-limiting example, the 3D voxel array 104 can be captured or generated by an ultrasound scanner, in which case the 3D voxel array 104 can be considered as a three-dimensional ultrasound scanned image. As even another non-limiting example, the 3D voxel array 104 can be captured or generated by a PET scanner, in which case the 3D voxel array 104 can be considered as a three-dimensional PET scanned image. In various instances, the 3D voxel array 104 can have undergone any suitable image reconstruction or other processing techniques (e.g., filtered back projection, resolution or quality enhancement).

Figure 2:
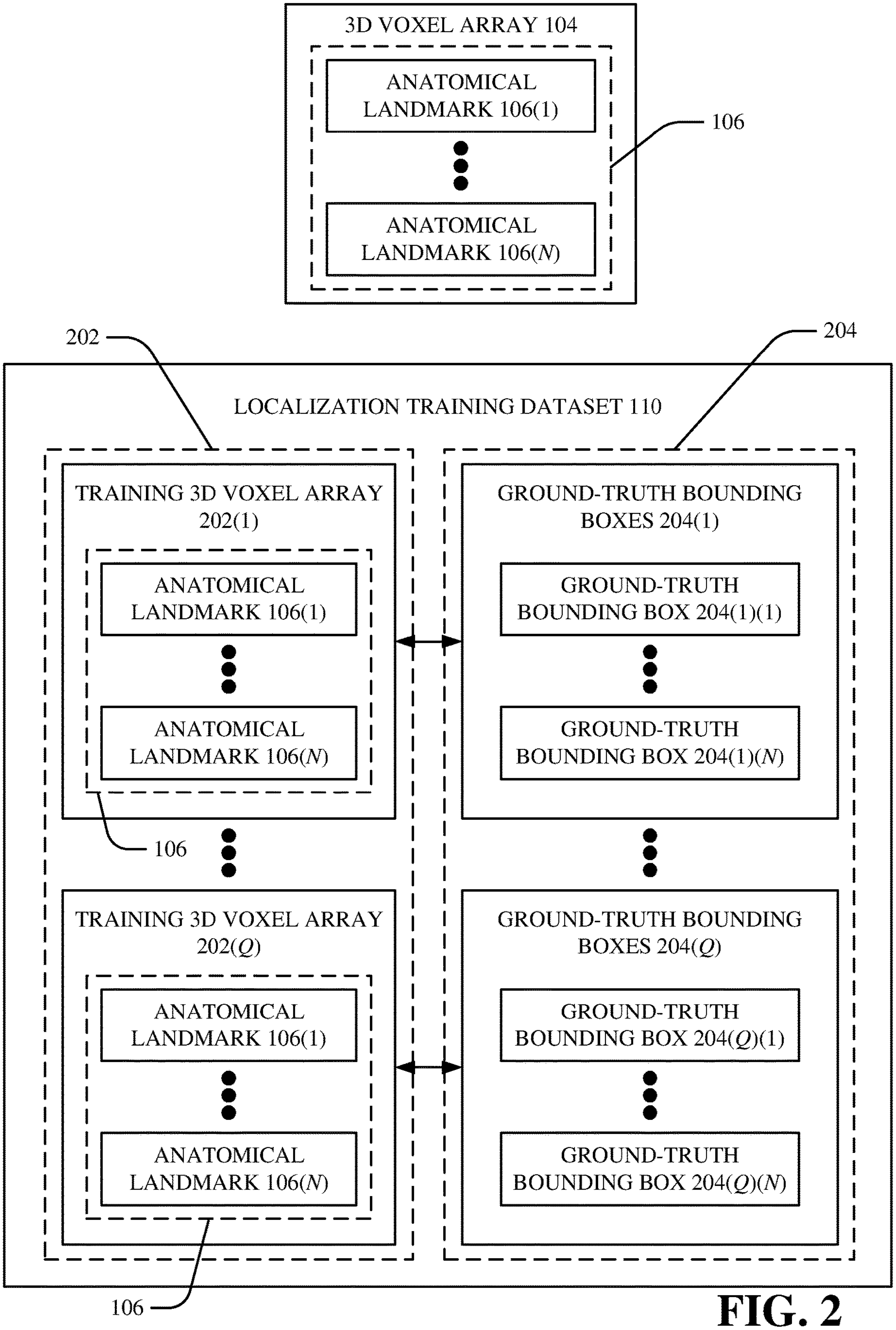
FIG. 2 illustrates an example, non-limiting block diagram showing a three-dimensional voxel array and a localization training dataset in accordance with one or more embodiments described herein.

In various cases, the 3D voxel array 104 can visually depict or illustrate any suitable anatomy (e.g., body part, organ, tissue, or portion thereof) of any suitable medical patient (e.g., human, animal, or otherwise). In various aspects, that anatomy can be considered, expected, or otherwise supposed to have a set of anatomical landmarks 106. In various instances, as shown in FIG. 2, the set of anatomical landmarks 106 can comprise n landmarks, for any suitable positive integer n: an anatomical landmark 106(1) to an anatomical landmark 106(*n*). In various cases, each of the set of anatomical landmarks 106 can be a distinct or unique locus that is biologically, clinically, or diagnostically meaningful with respect to the anatomy of the medical patient. As a non-limiting example, the anatomy can be a head of the medical patient. In such case, each of the set of anatomical landmarks 106 can be a respective locus that carries biological, clinical, or diagnostic relevance with respect to heads (e.g., can a nasion landmark, an ear canal landmark, or an optic chiasm landmark). As another non-limiting example, the anatomy can be a foot of the medical patient. In such case, each of the set of anatomical landmarks 106 can be a respective locus that carries biological, clinical, or diagnostic relevance with respect to feet (e.g., can be a cuboid landmark or a calcaneus landmark).

Referring back to FIG. 1, in various embodiments, the deep learning neural network 108 can be any suitable artificial neural network that can have or otherwise exhibit any suitable internal architecture. For instance, the deep learning neural network 108 can have an input layer, one or more hidden layers, and an output layer. In various instances, any of such layers can be coupled together by any suitable interneuron connections or interlayer connections, such as forward connections, skip connections, or recurrent connections. Furthermore, in various cases, any of such layers can be any suitable types of neural network layers having any suitable learnable or trainable internal parameters. For example, any of such input layer, one or more hidden layers, or output layer can be convolutional layers, whose learnable or trainable parameters can be convolutional kernels. As another example, any of such input layer, one or more hidden layers, or output layer can be dense layers, whose learnable or trainable parameters can be weight matrices or bias values. As still another example, any of such input layer, one or more hidden layers, or output layer can be batch normalization layers, whose learnable or trainable parameters can be shift factors or scale factors. Further still, in various cases, any of such layers can be any suitable types of neural network layers having any suitable fixed or non-trainable internal parameters. For example, any of such input layer, one or more hidden layers, or output layer can be non-linearity layers, padding layers, pooling layers, or concatenation layers.

In various aspects, the deep learning neural network 108 can be configured to localize the set of anatomical landmarks 106 in inputted voxel arrays. That is, the deep learning neural network 108 can be configured to receive as input any given voxel array, and the deep learning neural network 108 can be configured to produce as output a set of bounding boxes that respectively indicate where within that given voxel array the set of anatomical landmarks 106 are located.

In various instances, the deep learning neural network 108 can have been previously trained to perform such landmark localization based on the localization training dataset 110. In particular, the localization training dataset 110 can comprise various training voxel arrays that are annotated with ground-truth bounding boxes, and the deep learning neural network 108 can have been previously trained in supervised fashion on the localization training dataset 110.

Indeed, as shown in FIG. 2, the localization training dataset 110 can comprise a plurality of training 3D voxel arrays 202. In various aspects, the plurality of training 3D voxel arrays 202 can comprise q voxel arrays, for any suitable positive integer q: a training 3D voxel array 202(1) to a training 3D voxel array 202(*q*). In various instances, each of the plurality of training 3D voxel arrays 202 can exhibit the same format, size, or dimensionality as the 3D voxel array 104. For example, if the 3D voxel array 104 is an x-by-y-by-z voxel array, then each of the plurality of training 3D voxel arrays 202 can likewise be an x-by-y-by-z voxel array. In various cases, each of the plurality of training 3D voxel arrays 202 can visually depict a respective anatomy that is of the same type as that which is considered, expected, or supposed to be depicted in the 3D voxel array 104. Thus, as shown, each of the plurality of training 3D voxel arrays 202 can visually depict or illustrate some version or instantiation of the set of anatomical landmarks 106. As a non-limiting example, suppose that the 3D voxel array 104 is expected or supposed to depict the head of the medical patient, such that the set of anatomical landmarks 106 are head-relevant loci. In such case, each of the plurality of training 3D voxel arrays 202 can likewise depict the head, and thus the head-relevant loci, of a respective medical patient (e.g., the training 3D voxel array 202(1) can depict the head, and thus the head-relevant loci, of a first medical patient; the training 3D voxel array 202(*q*) can depict the head, and thus the head-relevant loci, of a q-th medical patient). As another non-limiting example, suppose that the 3D voxel array 104 is expected or supposed to depict the foot of the medical patient, such that the set of anatomical landmarks 106 are foot-relevant loci. In such case, each of the plurality of training 3D voxel arrays 202 can likewise depict the foot, and thus the foot-relevant loci, of a respective medical patient (e.g., the training 3D voxel array 202(1) can depict the foot, and thus the foot-relevant loci, of a first medical patient; the training 3D voxel array 202(*q*) can depict the foot, and thus the foot-relevant loci, of a q-th medical patient).

In various aspects, as shown, the localization training dataset 110 can further comprise a plurality of sets of ground-truth bounding boxes 204. In various instances, the plurality of sets of ground-truth bounding boxes 204 can respectively correspond to the plurality of training 3D voxel arrays 202. Accordingly, since the plurality of training 3D voxel arrays 202 can comprise q voxel arrays, the plurality of sets of ground-truth bounding boxes 204 can comprise q sets of ground-truth bounding boxes: a set of ground-truth bounding boxes 204(1) to a set of ground-truth bounding boxes 204(*q*). In various cases, each of the plurality of sets of ground-truth bounding boxes 204 can indicate intra-image locations of the set of anatomical landmarks 106 within a respective one of the plurality of training 3D voxel arrays 202.

As a non-limiting example, the training 3D voxel array 202(1) can correspond to the set of ground-truth bounding boxes 204(1). Thus, the set of ground-truth bounding boxes 204(1) can be considered as respectively indicating where the set of anatomical landmarks 106 are known to be located within the training 3D voxel array 202(1). More specifically, the set of ground-truth bounding boxes 204(1) can comprise a ground-truth bounding box 204(1)(1), which can be any suitable three-dimensional bounding box that is known or deemed to circumscribe the anatomical landmark 106(1) within the training 3D voxel array 202(1) (e.g., that indicates which specific voxels of the training 3D voxel array 202(1) are known or deemed to belong to or otherwise make up the anatomical landmark 106(1)). Likewise, the set of ground-truth bounding boxes 204(1) can comprise a ground-truth bounding box 204(1)(*n*), which can be any suitable three-dimensional bounding box that is known or deemed to circumscribe the anatomical landmark 106(*n*) within the training 3D voxel array 202(1) (e.g., that indicates which specific voxels of the training 3D voxel array 202(1) are known or deemed to belong to or otherwise make up the anatomical landmark 106(*n*)).

As another non-limiting example, the training 3D voxel array 202(*q*) can correspond to the set of ground-truth bounding boxes 204(*q*). So, the set of ground-truth bounding boxes 204(*q*) can be considered as respectively indicating where the set of anatomical landmarks 106 are known to be located within the training 3D voxel array 202(*q*). In particular, the set of ground-truth bounding boxes 204(*q*) can comprise a ground-truth bounding box 204(*q*)(1), which can be any suitable three-dimensional bounding box that is known or deemed to circumscribe the anatomical landmark 106(1) within the training 3D voxel array 202(*q*) (e.g., that indicates which specific voxels of the training 3D voxel array 202(*q*) are known or deemed to belong to or otherwise make up the anatomical landmark 106(1)). Similarly, the set of ground-truth bounding boxes 204(*q*) can comprise a ground-truth bounding box 204(*q*)(*n*), which can be any suitable three-dimensional bounding box that is known or deemed to circumscribe the anatomical landmark 106(*n*) within the training 3D voxel array 202(*q*) (e.g., that indicates which specific voxels of the training 3D voxel array 202(*q*) are known or deemed to belong to or otherwise make up the anatomical landmark 106(*n*)).

In various aspects, the deep learning neural network 108 can have been trained in supervised fashion on the localization training dataset 110. As a non-limiting example, prior to the start of such training, the trainable internal parameters (e.g., weight matrices, bias vectors, convolutional kernels) of the deep learning neural network 108 can have been initialized in any suitable fashion (e.g., random initialization). After such initialization, the deep learning neural network 108 can have been iteratively executed on the plurality of training 3D voxel arrays 202, and the trainable internal parameters of the deep learning neural network 108 can have been iteratively updated by backpropagating errors between the outputs produced by such executions and the plurality of sets of ground-truth bounding boxes 204. Such training can have involved any suitable error or objective function (e.g., mean absolute error (MAE), mean squared error (MSE), cross-entropy error), any suitable optimization algorithm (e.g., stochastic gradient descent), any suitable number of training epochs, or any suitable training batch sizes.

Referring back to FIG. 1, it can be desired to localize, via the deep learning neural network 108, the set of anatomical landmarks 106 within the 3D voxel array 104 and to estimate respective confidence scores for such localizations. As described herein, the landmark confidence system 102 can facilitate such localization and confidence estimation, based on the localization training dataset 110.

In various embodiments, the landmark confidence system 102 can comprise a processor 112 (e.g., computer processing unit, microprocessor) and a non-transitory computer-readable memory 114 that is operably or operatively or communicatively connected or coupled to the processor 112. The non-transitory computer-readable memory 114 can store computer-executable instructions which, upon execution by the processor 112, can cause the processor 112 or other components of the landmark confidence system 102 (e.g., access component 116, execution component 118, confidence component 120, classifier component 122) to perform one or more acts. In various embodiments, the non-transitory computer-readable memory 114 can store computer-executable components (e.g., access component 116, execution component 118, confidence component 120, classifier component 122), and the processor 112 can execute the computer-executable components.

In various embodiments, the landmark confidence system 102 can comprise an access component 116. In various aspects, the access component 116 can electronically receive or otherwise electronically access the 3D voxel array 104, the deep learning neural network 108, or the localization training dataset 110. In various instances, the access component 116 can electronically retrieve the 3D voxel array 104, the deep learning neural network 108, or the localization training dataset 110 from any suitable centralized or decentralized data structures (not shown) or from any suitable centralized or decentralized computing devices (not shown). In any case, the access component 116 can electronically obtain or access the 3D voxel array 104, the deep learning neural network 108, or the localization training dataset 110, such that other components of the landmark confidence system 102 can electronically interact with the 3D voxel array 104, with the deep learning neural network 108, or with the localization training dataset 110.

In various embodiments, the landmark confidence system 102 can comprise an execution component 118. In various aspects, as described herein, the execution component 118 can execute the deep learning neural network 108 on the 3D voxel array 104, thereby yielding a set of predicted bounding boxes that respectively indicate the inferred locations of the set of anatomical landmarks 106 within the 3D voxel array 104.

In various embodiments, the landmark confidence system 102 can comprise a confidence component 120. In various instances, as described herein, the confidence component 120 can generate a multi-tiered collection of confidence scores, based on the set of predicted bounding boxes and based on the localization training dataset 110.

In various embodiments, the landmark confidence system 102 can comprise a classifier component 122. In various cases, as described herein, the classifier component 122 can, in response to any of the multi-tiered collection of confidence scores failing to satisfy a threshold value, determine, via another deep learning neural network, a factor or reason explaining or justifying those failed confidence scores.

Figure 3:
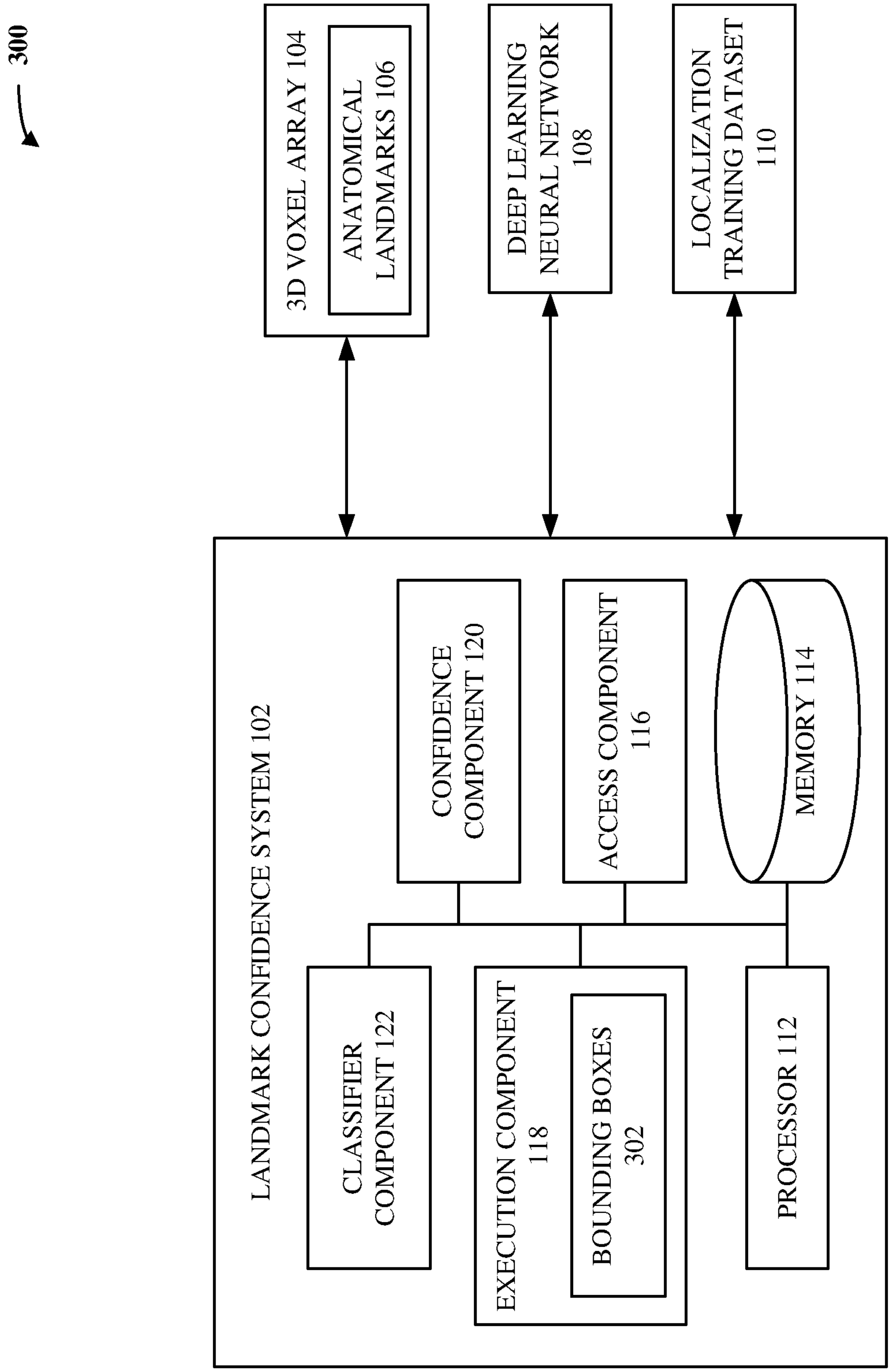
FIG. 3 illustrates a block diagram of an example, non-limiting system including a set of bounding boxes that facilitates explainable confidence estimation for landmark localization in accordance with one or more embodiments described herein.

FIG. 3 illustrates a block diagram of an example, non-limiting system 300 including a set of bounding boxes that can facilitate explainable confidence estimation for landmark localization in accordance with one or more embodiments described herein. As shown, the system 300 can, in some cases, comprise the same components as the system 100, and can further comprise a set of bounding boxes 302.

In various embodiments, the execution component 118 can electronically generate, predict, or otherwise infer the set of bounding boxes 302, by executing the deep learning neural network 108 on the 3D voxel array 104. Non-limiting aspects are described with respect to FIG. 4.

Figure 4:
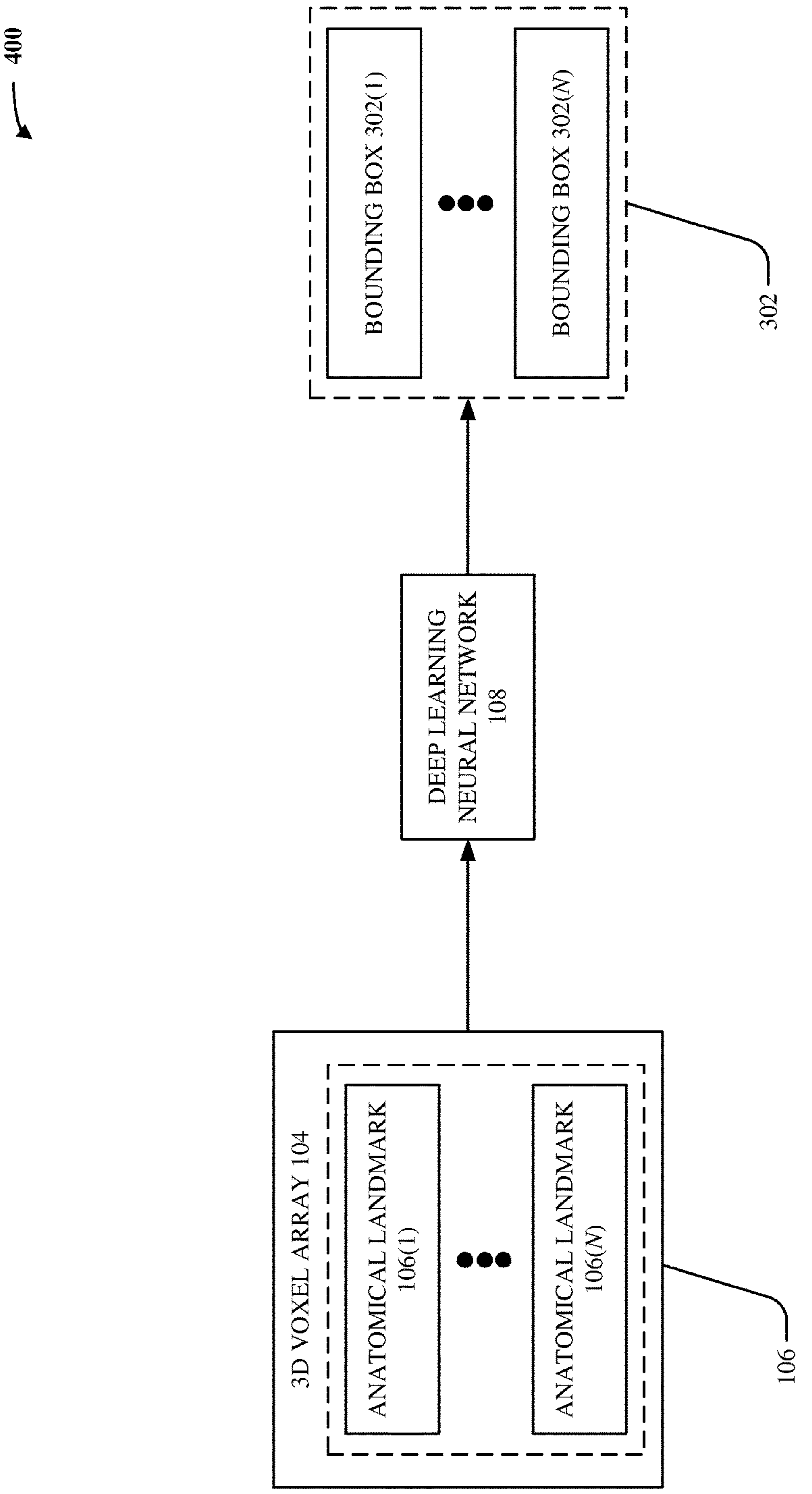
FIG. 4 illustrates an example, non-limiting block diagram showing how a localization neural network can predict a set of bounding boxes in accordance with one or more embodiments described herein.

FIG. 4 illustrates an example, non-limiting block diagram 400 showing how the deep learning neural network 108 can predict the set of bounding boxes 302 in accordance with one or more embodiments described herein.

In various aspects, the execution component 118 can electronically control or otherwise electronically operate the deep learning neural network 108. Accordingly, in various instances, the execution component 118 can electronically execute the deep learning neural network 108 on the 3D voxel array 104. In various cases, such execution can cause the deep learning neural network 108 to produce the set of bounding boxes 302. More specifically, the execution component 118 can feed the 3D voxel array 104 to an input layer of the deep learning neural network 108. In various aspects, the 3D voxel array 104 can complete a forward pass through one or more hidden layers of the deep learning neural network 108. In various instances, an output layer of the deep learning neural network 108 can compute or otherwise calculate the set of bounding boxes 302, based on activation maps generated by the one or more hidden layers of the deep learning neural network 108.

In any case, the set of bounding boxes 302 can respectively correspond to the set of anatomical landmarks 106. Thus, since the set of anatomical landmarks 106 can comprise n landmarks, the set of bounding boxes 302 can comprise n bounding boxes: a bounding box 302(1) to a bounding box **302(*n*). In various aspects, each of the set of bounding boxes 302 can be considered indicating an intra-image location within the 3D voxel array 104 of a respective one of the set of anatomical landmarks 106. As a non-limiting example, the bounding box 302(1) can be a three-dimensional bounding box that purports to circumscribe the anatomical landmark 106(1) within the 3D voxel array 104 (e.g., that indicates which specific voxels of the 3D voxel array 104 have been determined by the deep learning neural network 108 to belong to or otherwise make up the anatomical landmark 106(1)). As another non-limiting example, the bounding box 302(*n*) can be a three-dimensional bounding box that purports to circumscribe the anatomical landmark 106(*n*) within the 3D voxel array 104 (e.g., that indicates which specific voxels of the 3D voxel array 104** have been determined by the deep learning neural network 108 to belong to or otherwise make up the anatomical landmark 106(*n*)).

Figure 5:
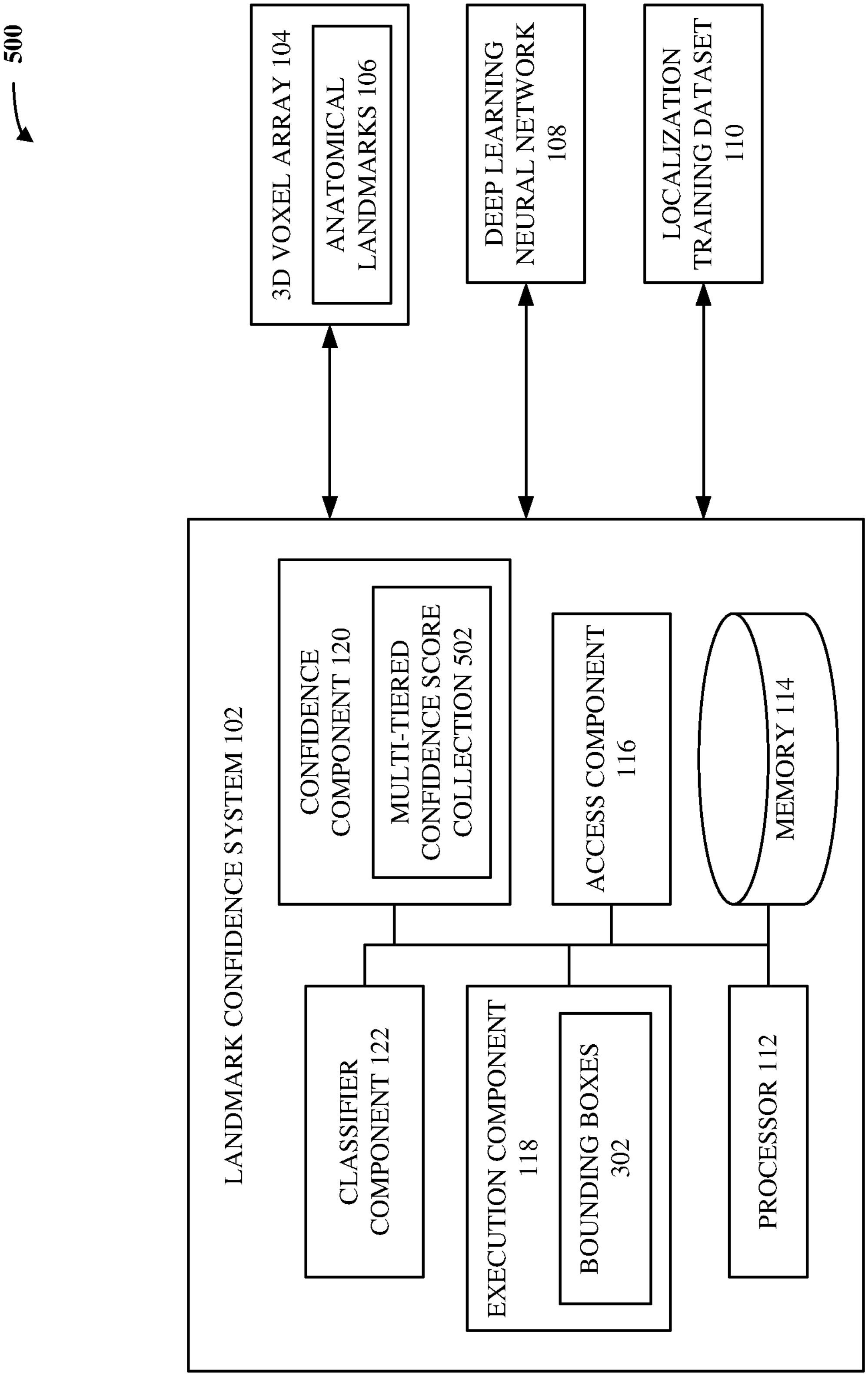
FIG. 5 illustrates a block diagram of an example, non-limiting system including a multi-tiered confidence score collection that facilitates explainable confidence estimation for landmark localization in accordance with one or more embodiments described herein.

FIG. 5 illustrates a block diagram of an example, non-limiting system 500 including a multi-tiered confidence score collection that can facilitate explainable confidence estimation for landmark localization in accordance with one or more embodiments described herein. As shown, the system 500 can, in some cases, comprise the same components as the system 300, and can further comprise a multi-tiered confidence score collection 502.

In various embodiments, the confidence component 120 can electronically generate the multi-tiered confidence score collection 502, based on the set of bounding boxes 302, and based on the localization training dataset 110. Various non-limiting aspects are described with respect to FIGS. 6-14.

Figure 6:
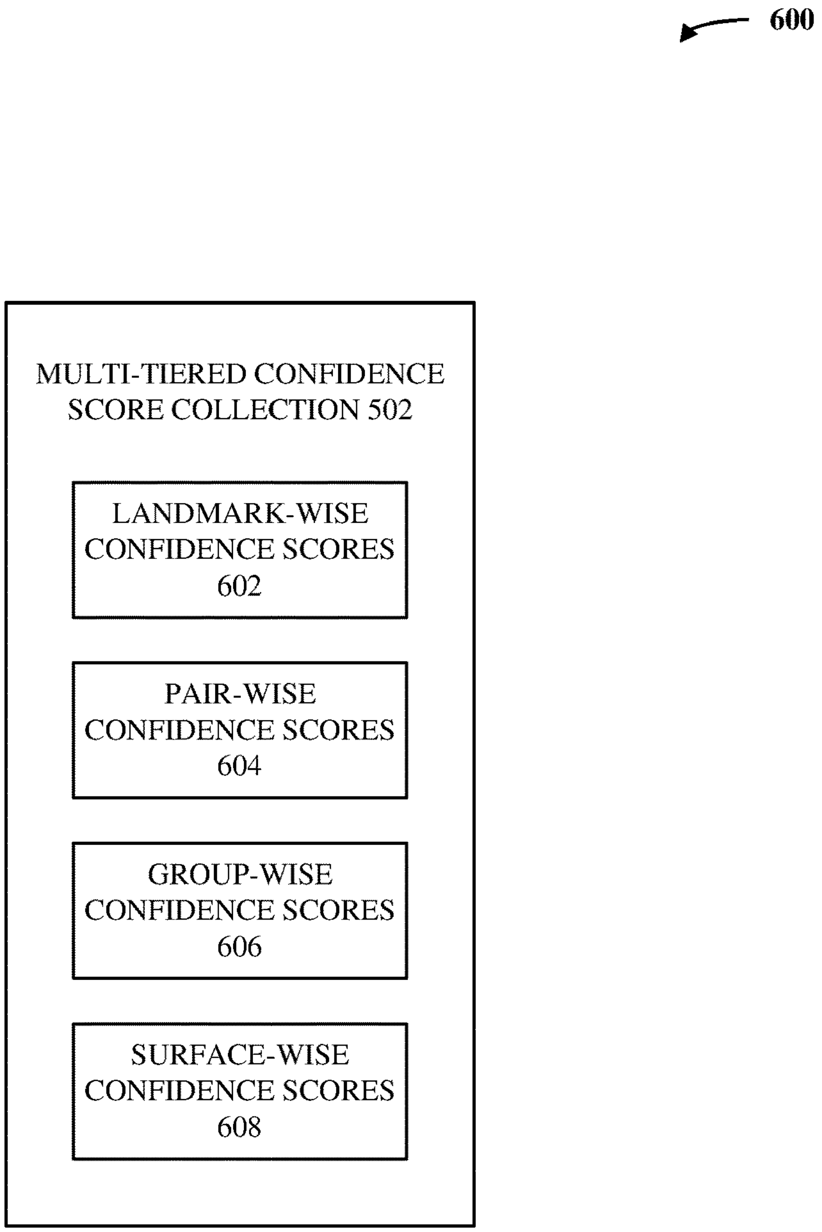
FIG. 6 illustrates an example, non-limiting block diagram of a multi-tiered confidence score collection in accordance with one or more embodiments described herein.

FIG. 6 illustrates an example, non-limiting block diagram 600 of the multi-tiered confidence score collection 502 in accordance with one or more embodiments described herein.

In various embodiments, a confidence score can be a real-valued scalar having any suitable magnitude range (e.g., ranging from 0 to 1), where a higher magnitude can indicate a higher confidence (e.g., a lower amount of uncertainty). However, this is a mere non-limiting example. In other instances, a confidence score can be a real-valued scalar having any suitable magnitude range, where a higher magnitude can indicate a lower confidence (e.g., a higher amount of uncertainty). In any case, the multi-tiered confidence score collection 502 can comprise multiple tiers of confidence scores, with each tier capturing, reflecting, or monitoring for a respective aspect or type of landmark localization failure. In various aspects, the multi-tiered confidence score collection 502 can comprise a set of landmark-wise confidence scores 602, a set of pair-wise confidence scores 604, a set of group-wise confidence scores 606, or a set of surface-wise confidence scores 608.

In various aspects, the set of landmark-wise confidence scores 602 can be considered as a first confidence score tier that captures, reflects, or monitors for irregularities in the bounding boxes of individual ones of the set of anatomical landmarks 106. Various non-limiting aspects of the set of landmark-wise confidence scores 602 are described with respect to FIGS. 7-8. In various instances, the set of pair-wise confidence scores 604 can be considered as a second confidence score tier that captures, reflects, or monitors for irregularities in the bounding boxes of anatomically symmetric pairs of the set of anatomical landmarks 106. Various non-limiting aspects of the set of pair-wise confidence scores 604 are described with respect to FIGS. 9-10. In various cases, the set of group-wise confidence scores 606 can be considered as a third confidence score tier that captures, reflects, or monitors for irregularities in the bounding boxes of anthropometric groups of the set of anatomical landmarks 106. Various non-limiting aspects of the set of group-wise confidence scores 606 are described with respect to FIGS. 11-12. In various aspects, the set of surface-wise confidence scores 608 can be considered as a fourth confidence score tier that captures, reflects, or monitors for irregularities in the bounding boxes of surface-defining groups of the set of anatomical landmarks 106. Various non-limiting aspects of the set of surface-wise confidence scores 608 are described with respect to FIGS. 13-14.

Figure 7:
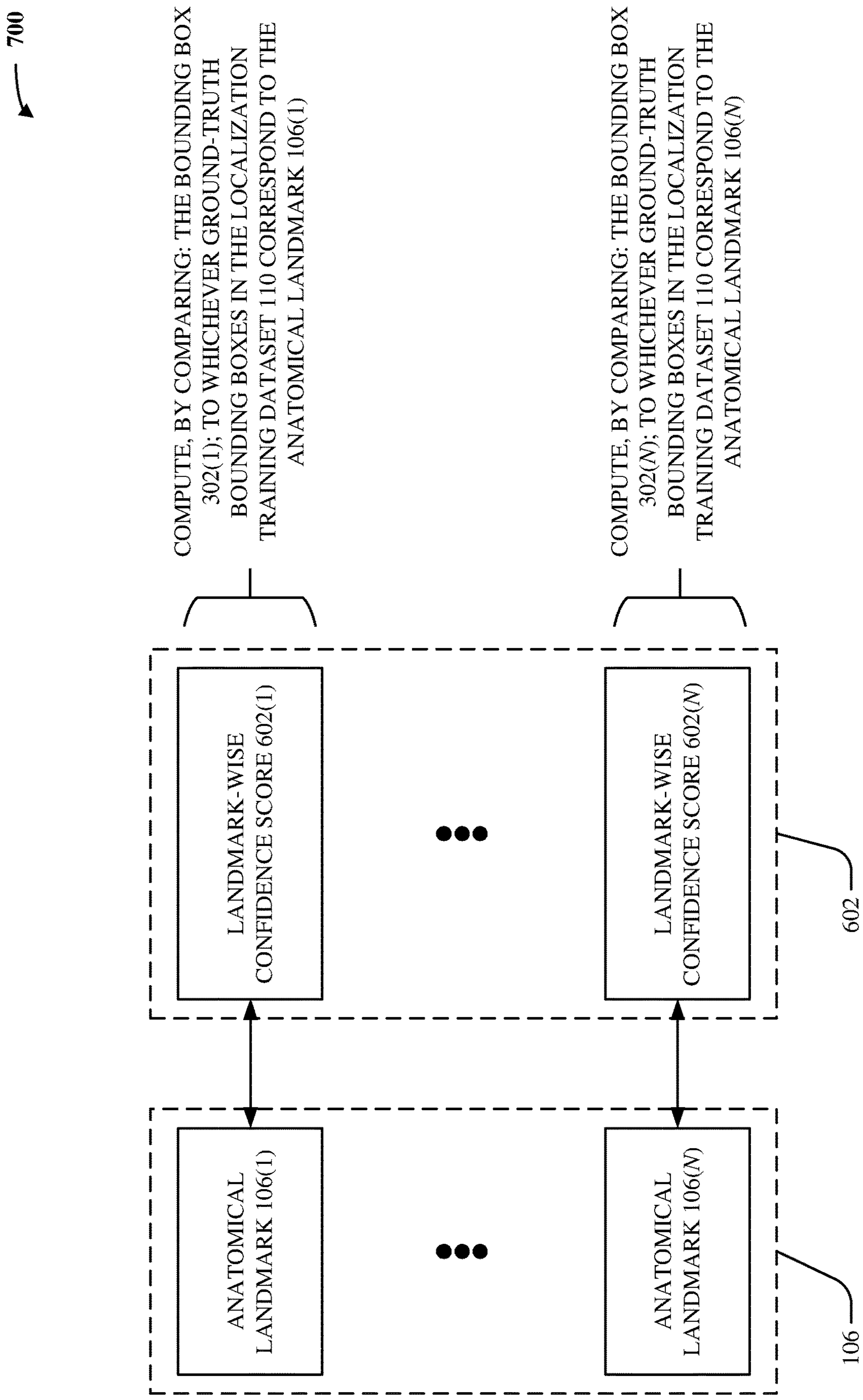
FIGS. 7-8 illustrate example, non-limiting block diagrams showing how landmark-wise confidence scores of a multi-tiered confidence score collection can be computed in accordance with one or more embodiments described herein.
Figure 8:
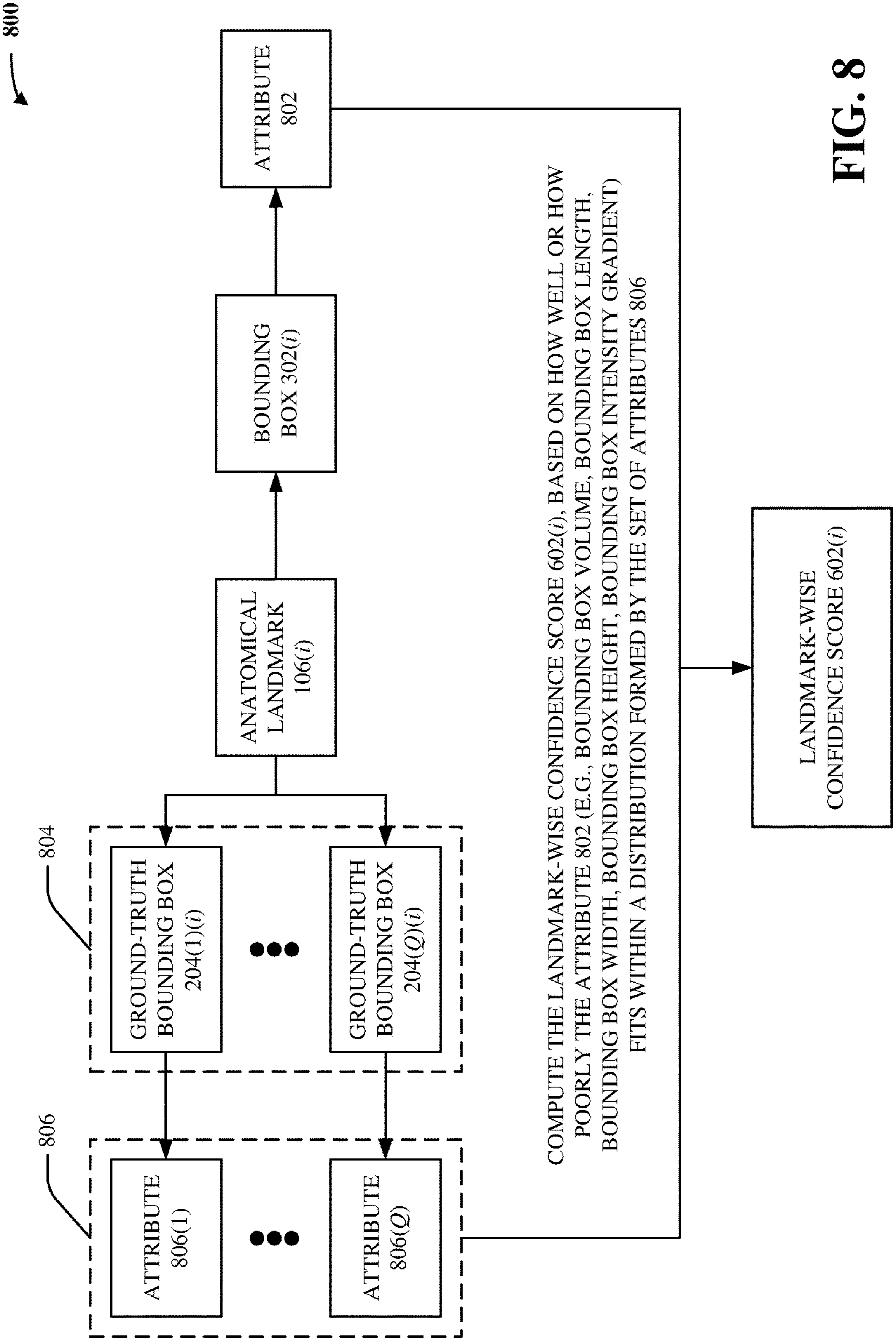

FIGS. 7-8 illustrate example, non-limiting block diagrams 700 and 800 showing how the set of landmark-wise confidence scores 602 of the multi-tiered confidence score collection 502 can be computed in accordance with one or more embodiments described herein.

In various embodiments, as shown in FIG. 7, the set of landmark-wise confidence scores 602 can respectively correspond to the set of anatomical landmarks 106. Thus, because the set of anatomical landmarks 106 can comprise n landmarks, the set of landmark-wise confidence scores 602 can comprise n scores: a landmark-wise confidence score 602(1) to a landmark-wise confidence score 602(*n*). In various aspects, each of the set of landmark-wise confidence scores 602 can indicate how confidently or unconfidently the deep learning neural network 108 individually localized a respective one of the set of anatomical landmarks 106 within the 3D voxel array 104. In particular, the confidence component 120 can compute each of the set of landmark-wise confidence scores 602, by comparing a respective one of the set of bounding boxes 302 to respective ground-truth bounding boxes in the localization training dataset 110.

As a non-limiting example, the landmark-wise confidence score 602(1) can correspond to the anatomical landmark 106(1). Accordingly, since the bounding box 302(1) can represent the predicted location of the anatomical landmark 106(1) within the 3D voxel array 104, the landmark-wise confidence score 602(1) can be considered as representing a level of individual confidence for the bounding box 302(1). In various aspects, the confidence component 120 can compute the landmark-wise confidence score 602(1), by comparing the bounding box 302(1) to whichever ground-truth bounding boxes within the localization training dataset 110 correspond to the anatomical landmark 106(1).

As another non-limiting example, the landmark-wise confidence score 602(*n*) can correspond to the anatomical landmark 106(*n*). Thus, since the bounding box 302(*n*) can represent the predicted location of the anatomical landmark 106(*n*) within the 3D voxel array 104, the landmark-wise confidence score 602(*n*) can be considered as representing a level of individual confidence for the bounding box 302(*n*). In various aspects, the confidence component 120 can compute the landmark-wise confidence score 602(*n*), by comparing the bounding box 302(*n*) to whichever ground-truth bounding boxes within the localization training dataset 110 correspond to the anatomical landmark 106(*n*).

Consider FIG. 8, which illustrates a non-limiting example of how a landmark-wise confidence score can be computed.

In various embodiments, consider an anatomical landmark 106(*i*) from the set of anatomical landmarks 106, for any suitable positive integer $1 \leq i \leq n$. In various aspects, the set of bounding boxes 302 can comprise a bounding box 302(*i*) that corresponds to the anatomical landmark 106(*i*). Just as explained above, the bounding box 302(*i*) can represent which voxels of the 3D voxel array 104 have been inferred by the deep learning neural network 108 to belong to the anatomical landmark 106(*i*). In various instances, the bounding box 302(*i*) can have or otherwise exhibit an attribute 802. In various cases, the attribute 802 can be any suitable measurable property or characteristic of the bounding box 302(*i*). As a non-limiting example, the attribute 802 can be a spatial volume of the bounding box 302(*i*). As another non-limiting example, the attribute 802 can be a spatial length of the bounding box 302(*i*). As yet another non-limiting example, the attribute 802 can be a spatial width of the bounding box 302(*i*). As even another non-limiting example, the attribute 802 can be a spatial height of the bounding box 302(*i*). As still another non-limiting example, the attribute 802 can be an intensity gradient of the bounding box 302(*i*).

In various aspects, as mentioned above, the localization training dataset 110 can comprise a total of q training 3D voxel arrays that each depict some instantiation of the anatomical landmark 106($i$). Thus, as shown by numeral 804, the localization training dataset 110 can be considered as comprising a total of q ground-truth bounding boxes that correspond to anatomical landmark 106($i$): a ground-truth bounding box 204(1)($i$) to a ground-truth bounding box 204($q$)($i$). In various cases, the ground-truth bounding box 204(1)($i$) can be considered as indicating which voxels of the training 3D voxel array 202(1) are known or deemed to belong to the anatomical landmark 106($i$). Similarly, the ground-truth bounding box 204($q$)($i$) can be considered as indicating which voxels of the training 3D voxel array 202($q$) are known or deemed to belong to the anatomical landmark 106($i$).

In various aspects, just as the bounding box 302($i$) can have or exhibit the attribute 802, each of the q ground-truth bounding boxes denoted by numeral 804 can likewise have or exhibit a respective attribute. As a non-limiting example, the ground-truth bounding box 204(1)($i$) can have or exhibit an attribute 806(1) that can be of a same type as the attribute 802 (e.g., if the attribute 802 is a spatial volume of the bounding box 302($i$), then the attribute 806(1) can be a spatial volume of the ground-truth bounding box 204(1)($i$); if the attribute 802 is an intensity gradient of the bounding box 302($i$), then the attribute 806(1) can be an intensity gradient of the ground-truth bounding box 204(1)($i$)). As another non-limiting example, the ground-truth bounding box 204($q$)($i$) can have or exhibit an attribute 806($q$) that can be of a same type as the attribute 802 (e.g., if the attribute 802 is a spatial width of the bounding box 302($i$), then the attribute 806($q$) can be a spatial width of the ground-truth bounding box 204($q$)($i$); if the attribute 802 is a spatial height of the bounding box 302($i$), then the attribute 806($q$) can be a spatial height of the ground-truth bounding box 204($q$)($i$)). In various cases, the attribute 806(1) to the attribute 806($q$) can be considered as collectively forming a set of attributes 806.

In various aspects, the confidence component 120 can compute a landmark-wise confidence score 602($i$) in the set of landmark-wise confidence scores 602, based on how well or how poorly the attribute 802 fits within a distribution formed by the set of attributes 806. For instance, the distribution formed by the set of attributes 806 can be defined by a mean attribute value and a standard deviation attribute value, and the confidence component 120 can determine the probability that the attribute 802 comes from that distribution (e.g., based on how many standard deviations the attribute 802 is from the mean). In various cases, the landmark-wise confidence score 602($i$) can be equal to or otherwise based on that probability.

As a mere non-limiting example, consider the following. The bounding box 302($i$) can have a volume denoted as $V_i$, a length denoted as $L_i$, a width denoted as $W_i$, a height denoted as $H_i$, and an intensity gradient denoted as $I_i$. In various cases, the q ground-truth bounding boxes shown by numeral 804 can have a volume mean and a volume standard deviation respectively denoted as $\mu_{V_i}$ and $\sigma_{V_i}$, can have a length mean and a length standard deviation respectively denoted as $\mu_{L_i}$ and $\sigma_{L_i}$, can have a width mean and a width standard deviation respectively denoted as $\mu W_i$ and $\sigma W_i$, can have a height mean and a height standard deviation respectively denoted as $\mu_{H_i}$ and $\sigma_{H_i}$, and can have an intensity gradient mean and an intensity gradient standard deviation respectively denoted as $\mu_{I_i}$ and $\sigma_{I_i}$. In various aspects, the confidence component 120 can compute a probability value, denoted as $p_{V_i}$, which can indicate how well or how poorly $V_i$ fits into the distribution defined by $\mu_{V_i}$ and $\sigma_{V_i}$. Likewise, the confidence component 120 can compute a probability value, denoted as $p_{L_i}$, which can indicate how well or how poorly $L_i$ fits into the distribution defined by $\mu_{L_i}$ and $\sigma_{L_i}$. Similarly, the confidence component 120 can compute a probability value, denoted as $p_{W_i}$, which can indicate how well or how poorly $W_i$ fits into the distribution defined by $\mu_{W_i}$ and $\sigma_{W_i}$. In like fashion, the confidence component 120 can compute a probability value, denoted as $p_{H_i}$, which can indicate how well or how poorly $H_i$ fits into the distribution defined by $\mu_{H_i}$ and $\sigma_{H_i}$. In similar fashion, the confidence component 120 can compute a probability value, denoted as $p_{H_i}$, which can indicate how well or how poorly $I_i$ fits into the distribution defined by $\mu_{I_i}$ and $\sigma_{I_i}$.

In various aspects, the confidence component 120 can compute a volume confidence metric as follows:

$$conf_{V_i} = \frac{p_{V_i}}{\max_{i \in [1,n]} p_{V_i}}$$

Likewise, the confidence component 120 can compute a linear dimension confidence metric as follows:

$$conf_{D_i} = \frac{p_{L_i} * p_{W_i} * p_{H_i}}{\max_{i \in [1,n]}\left[p_{L_i} * p_{W_i} * p_{H_i}\right]}$$

Similarly, the confidence component 120 can compute an intensity gradient confidence metric as follows:

$$conf_{I_i} = \frac{p_{I_i}}{\max_{i \in [1,n]} p_{I_i}}$$

In various aspects, the landmark-wise confidence score 602($i$) can then be equal to or otherwise based on any suitable aggregation (e.g., weighted linear combination, non-weighted linear combination) of $conf_{V_i}$, $conf_{D_i}$, and $Conf_{I_i}$.

In this way, the confidence component 120 can compute a respective landmark-wise confidence score for each of the set of anatomical landmarks 106.

Figure 9:
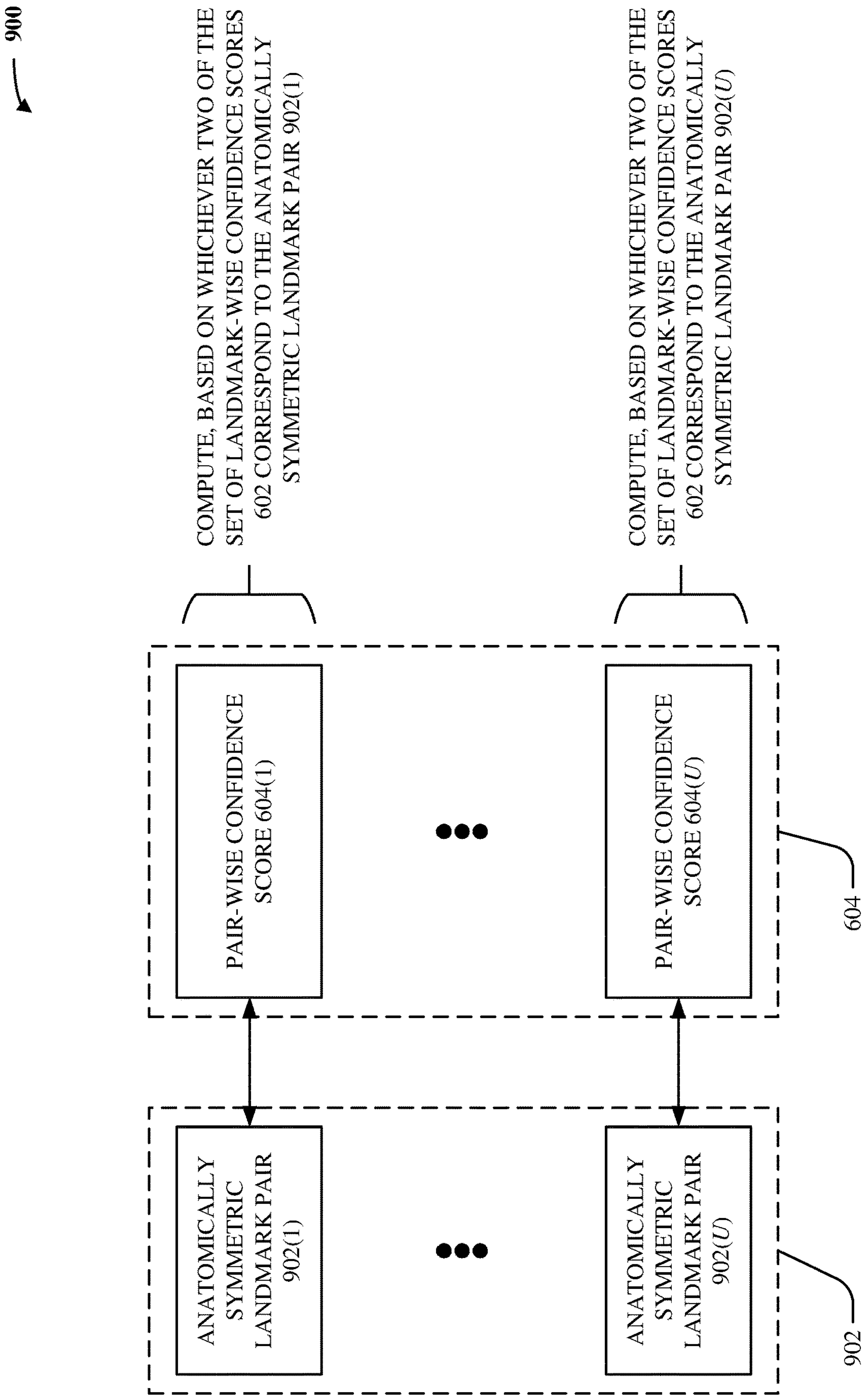
FIGS. 9-10 illustrate example, non-limiting block diagrams showing how pair-wise confidence scores of a multi-tiered confidence score collection can be computed in accordance with one or more embodiments described herein.
Figure 10:
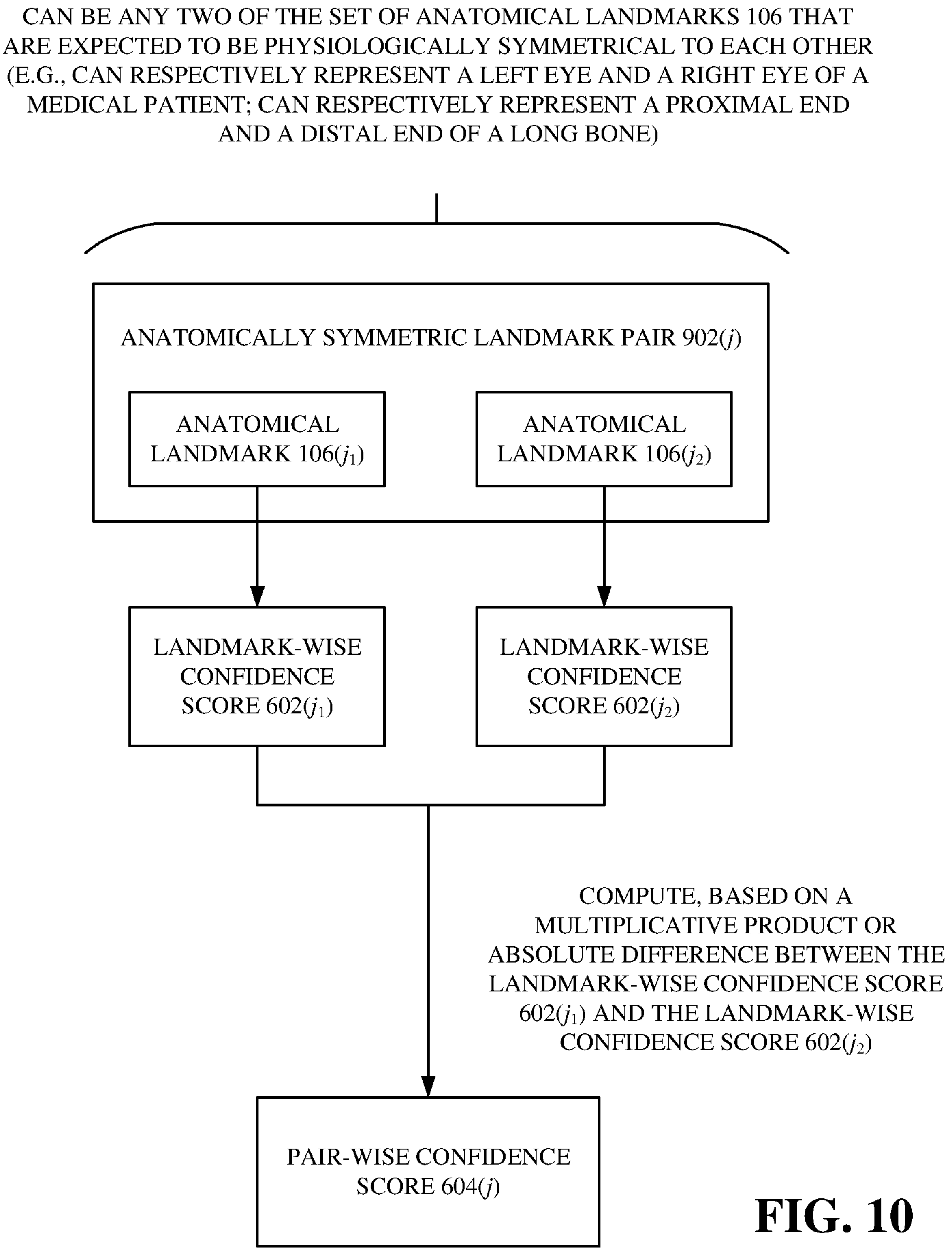

FIGS. 9-10 illustrate example, non-limiting block diagrams 900 and 1000 showing how the set of pair-wise confidence scores 604 of the multi-tiered confidence score collection 502 can be computed in accordance with one or more embodiments described herein.

In various embodiments, as shown in FIG. 9, there can be a set of anatomically symmetric landmark pairs 902. In various aspects, the set of anatomically symmetric landmark pairs 902 can comprise u pairs, for any suitable positive integer u: an anatomically symmetric landmark pair 902(1) to an anatomically symmetric landmark pair 902($u$). In various instances, each of the set of anatomically symmetric landmark pairs 902 can be any pair of landmarks from the set of anatomical landmarks 106 that are normally or usually expected to be anatomically, physiologically, or biologically symmetrical with respect to each other. As a non-limiting example, the anatomically symmetric landmark pair 902(1) can be a first pair of the set of anatomical landmarks 106 that are expected to be physically symmetric to each other. As another non-limiting example, the anatomically symmetric landmark pair 902($u$) can be a u-th pair of the set of anatomical landmarks 106 that are expected to be physically symmetric to each other.

In various aspects, as shown, the set of pair-wise confidence scores 604 can respectively correspond to the set of anatomically symmetric landmark pairs 902. Thus, because the set of anatomically symmetric landmark pairs 902 can comprise u pairs, the set of pair-wise confidence scores 604 can comprise u scores: a pair-wise confidence score 604(1) to a pair-wise confidence score 604($u$). In various aspects, each of the set of pair-wise confidence scores 604 can indicate whether or not the deep learning neural network 108 localized a respective one of the set of anatomically symmetric landmark pairs 902 with comparable (e.g., symmetric) confidence. In particular, the confidence component 120 can compute each of the set of pair-wise confidence scores 604, by comparing respective pairs of the set of landmark-wise confidence scores 602.

As a non-limiting example, the pair-wise confidence score 604(1) can correspond to the anatomically symmetric landmark pair 902(1). Accordingly, the confidence component 120 can compute the pair-wise confidence score 604(1), based on whichever two of the set of landmark-wise confidence scores 602 correspond to the two landmarks that make up the anatomically symmetric landmark pair 902(1).

As another non-limiting example, the pair-wise confidence score 604($u$) can correspond to the anatomically symmetric landmark pair 902($u$). So, the confidence component 120 can compute the pair-wise confidence score 604($u$), based on whichever two of the set of landmark-wise confidence scores 602 correspond to the two landmarks that make up the anatomically symmetric landmark pair 902($u$).

Consider FIG. 10, which illustrates a non-limiting example of how a pair-wise confidence score can be computed.

In various embodiments, there can be an anatomically symmetric landmark pair 902($j$) in the set of anatomically symmetric landmark pairs 902, for any suitable positive integer $1 \leq j \leq u$. In various aspects, as shown, the anatomically symmetric landmark pair 902($j$) can be considered as comprising an anatomical landmark 106($j_1$) and an anatomical landmark 106($j_2$) from the set of anatomical landmarks 106, for any suitable positive integers $1 \leq j_1 < j_2 \leq n$. In various instances, the anatomical landmark 106($j_1$) and the anatomical landmark 106($j_2$) can be any suitable landmarks that are expected to be physically symmetric to each other. As a non-limiting example, the anatomical landmark 106($j_1$) can be a right eye, and the anatomical landmark 106($j_2$) can be a left eye. As another non-limiting example, the anatomical landmark 106($j_1$) can be a right ear canal, and the anatomical landmark 106($j_2$) can be a left ear canal. As even another non-limiting example, the anatomical landmark 106($j_1$) can be a distal end of a long bone, and the anatomical landmark 106($j_2$) can be a proximal end of the long bone.

In any case, as described above, the confidence component 120 can compute a landmark-wise confidence score 602($j_1$) for the anatomical landmark 106($j_1$), and the confidence component 120 can compute a landmark-wise confidence score 602($j_2$) for the anatomical landmark 106($j_2$). In various aspects, the confidence component 120 can compute a pair-wise confidence score 604($j$) from the set of pair-wise confidence scores 604, based on a multiplicative product or an absolute difference between the landmark-wise confidence score 602($j_1$) and the landmark-wise confidence score 602($j_2$). As a non-limiting example, the pair-wise confidence score 604($j$) can be equal to or otherwise based on the following expression:

$$\left(1-\left|conf_{j_1}-conf_{j_2}\right|\right)*\left(conf_{j_1}*conf_{j_2}\right)$$

where $conf_{j_1}$ can denote the landmark-wise confidence score 602($j_1$), and where $conf_{j_2}$ can denote the landmark-wise confidence score 602($j_2$). The absolute difference portion of such expression (e.g., $(1-|conf_{j_1}-conf_{j_2}|)$) can be considered as monitoring for or otherwise capturing mismatches or disparities between the landmark-wise confidence score 602($j_1$) and the landmark-wise confidence score 602($j_2$). In other words, because the anatomical landmark 106($j_1$) and the anatomical landmark 106($j_2$) can be expected to be physically symmetric with respect to each other, it can be commensurately expected that the deep learning neural network 108 localize them with similar or comparable confidences. If the deep learning neural network 108 instead localizes them with dissimilar, disparate, or otherwise non-symmetric confidences, then it can be concluded that something went amiss with such localizations, and the absolute difference portion of such expression can reflect this. Moreover, the multiplicative product portion of such expression (e.g., $(conf_{j_1}*conf_{j_2})$) can be considered as monitoring for symmetrically or non-disparate unconfident localizations. That is, if the deep learning neural network 108 localizes the anatomical landmark 106($j_1$) and the anatomical landmark 106($j_2$) with similar or comparable confidences that are low, then it can nevertheless be concluded that something went amiss with such localizations, and the multiplicative product portion of such expression can reflect this.

In this way, the confidence component 120 can compute a respective pair-wise confidence score for each anatomically symmetric pair of the set of anatomical landmarks 106.

Figure 11:
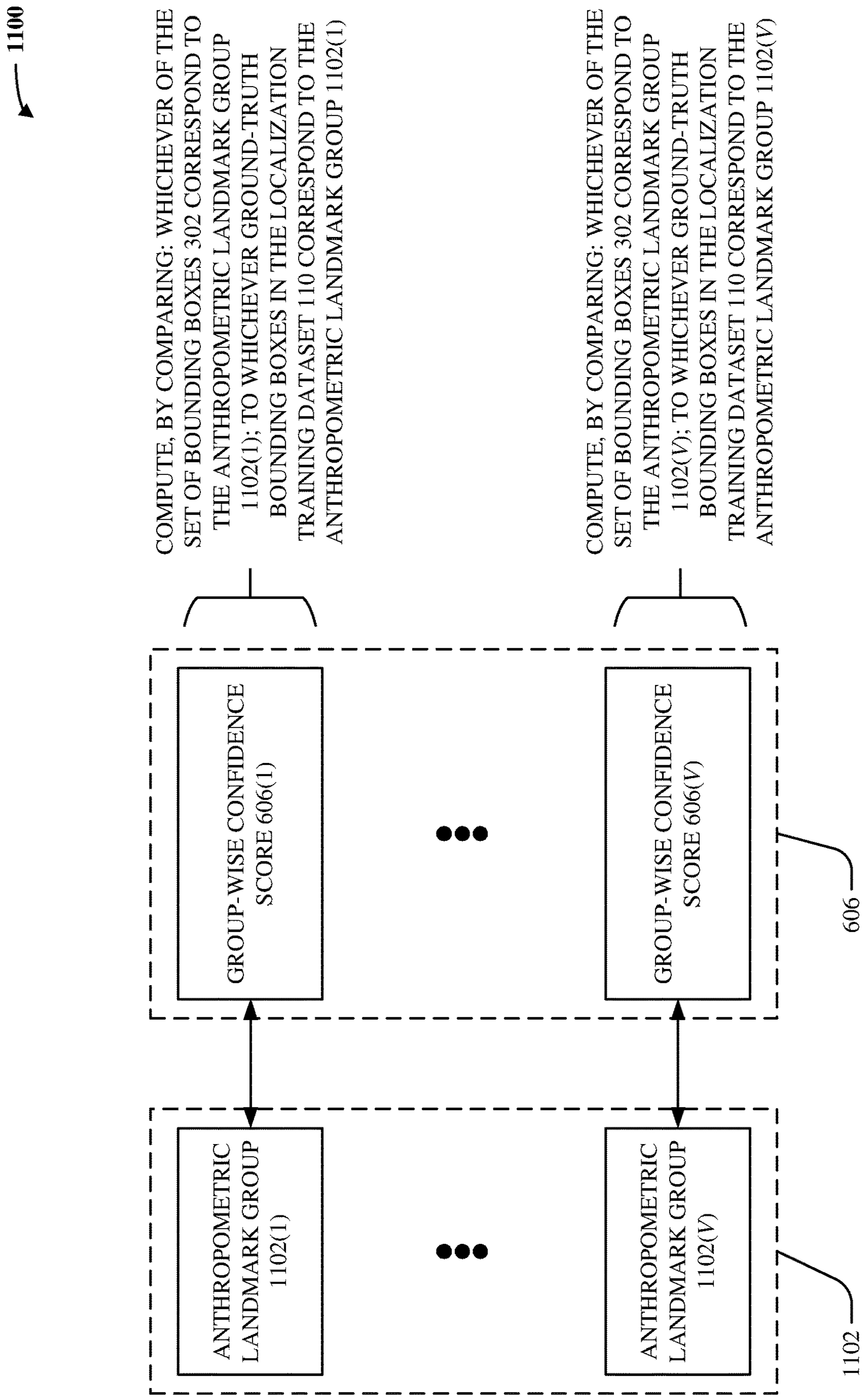
FIGS. 11-12 illustrate example, non-limiting block diagrams showing how group-wise confidence scores of a multi-tiered confidence score collection can be computed in accordance with one or more embodiments described herein.
Figure 12:
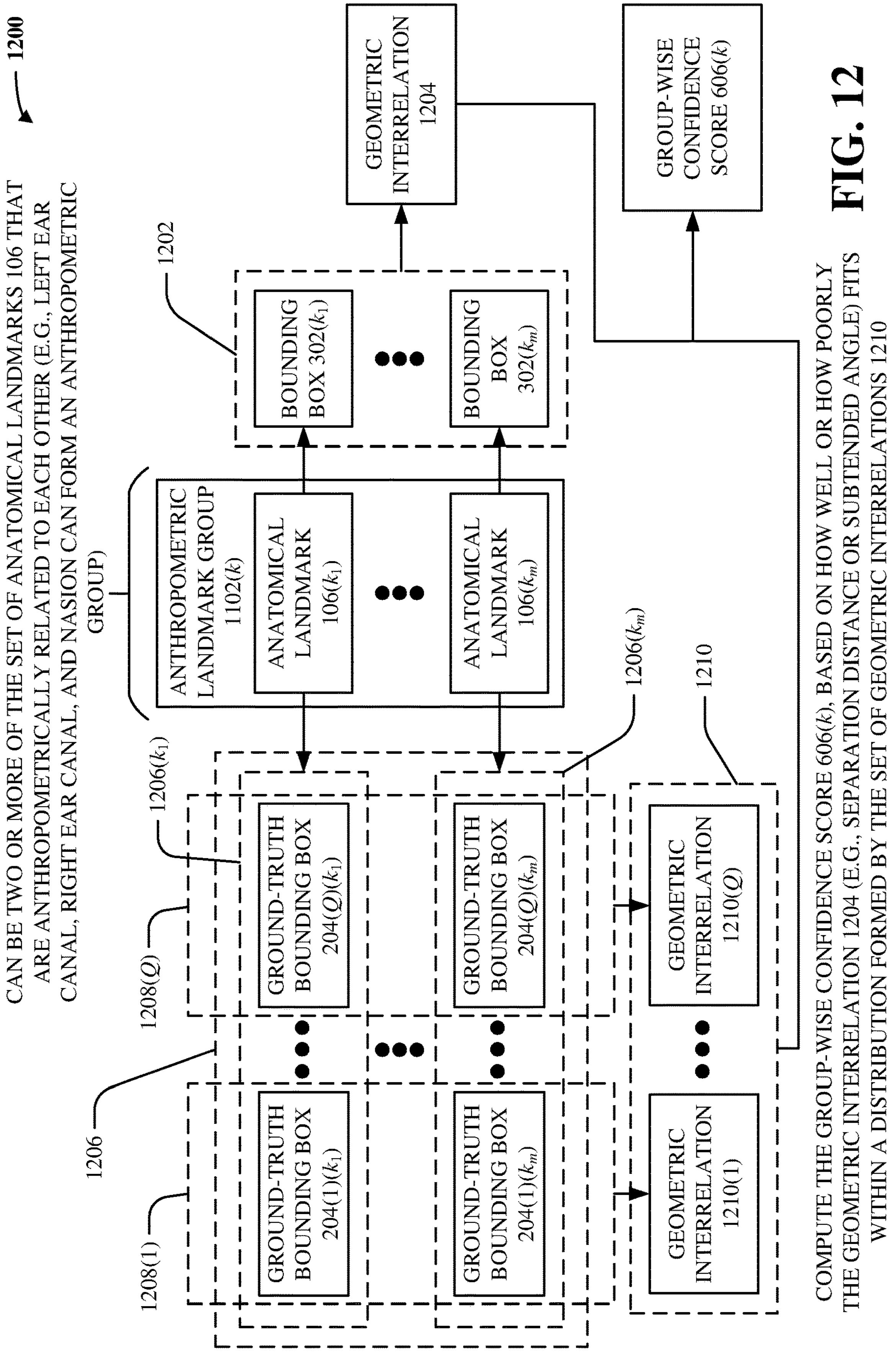

FIGS. 11-12 illustrate example, non-limiting block diagrams 1100 and 1200 showing how the set of group-wise confidence scores 606 of the multi-tiered confidence score collection 502 can be computed in accordance with one or more embodiments described herein.

In various embodiments, as shown in FIG. 11, there can be a set of anthropometric landmark groups 1102. In various aspects, the set of anthropometric landmark groups 1102 can comprise v groups, for any suitable positive integer v: an anthropometric landmark group 1102(1) to an anthropometric landmark group 1102($v$). In various instances, each of the set of anthropometric landmark groups 1102 can be any two or more landmarks from the set of anatomical landmarks 106 that are normally or usually expected to have some sort of stable or predictable anthropometric relationship with respect to each other. As a non-limiting example, the anthropometric landmark group 1102(1) can be a first subset of the set of anatomical landmarks 106 that are expected to be anthropometrically related to each other. As another non-limiting example, the anthropometric landmark group 1102($v$) can be a v-th subset of the set of anatomical landmarks 106 that are expected to be anthropometrically related to each other. Note that different ones of the set of anthropometric landmark groups 1102 can have the same or different total numbers of anatomical landmarks as each other.

In various aspects, as shown, the set of group-wise confidence scores 606 can respectively correspond to the set of anthropometric landmark groups 1102. Thus, because the set of anthropometric landmark groups 1102 can comprise v groups, the set of group-wise confidence scores 606 can comprise v scores: a group-wise confidence score 606(1) to a group-wise confidence score 606($v$). In various aspects, each of the set of group-wise confidence scores 606 can indicate whether or not the localizations predicted by the deep learning neural network 108 for a respective one of the set of anthropometric landmark groups 1102 obey whatever anthropometric relationships are expected for that respective one of the set of anthropometric landmark groups 1102.

As a non-limiting example, the group-wise confidence score 606(1) can correspond to the anthropometric landmark group 1102(1). Accordingly, the confidence component 120 can compute the group-wise confidence score 606(1), by comparing: anthropometric relationships exhibited by whichever of the set of bounding boxes 302 correspond to the anthropometric landmark group 1102(1); to analogous anthropometric relationships exhibited by whichever ground-truth bounding boxes in the localization training dataset 110 correspond to the anthropometric landmark group 1102(1).

As another non-limiting example, the group-wise confidence score 606($v$) can correspond to the anthropometric landmark group 1102($v$). So, the confidence component 120 can compute the group-wise confidence score 606($v$), by comparing: anthropometric relationships exhibited by whichever of the set of bounding boxes 302 correspond to the anthropometric landmark group 1102($v$); to analogous anthropometric relationships exhibited by whichever ground-truth bounding boxes in the localization training dataset 110 correspond to the anthropometric landmark group 1102($v$).

Consider FIG. 12, which illustrates a non-limiting example of how a group-wise confidence score can be computed.

In various embodiments, there can be an anthropometric landmark group 1102($k$) in the set of anthropometric landmark groups 1102, for any suitable positive integer $1 \leq k \leq v$. In various aspects, as shown, the anthropometric landmark group 1102($k$) can comprise a total of m landmarks from the set of anatomical landmarks 106: an anatomical landmark 106($k_1$) to an anatomical landmark 106($k_m$), for any suitable positive integers $1 \leq k_1 < \ldots < k_m \leq n$. In various instances, such m anatomical landmarks can be any suitable landmarks that are expected to have stable or otherwise predictable anthropometric relationships with respect to each other. As a non-limiting example, m can be equal to 3, where a first one of the anthropometric landmark group 1102($k$) can be a nasion, where a second one of the anthropometric landmark group 1102($k$) can be a right ear canal, and where a third one of the anthropometric landmark group 1102($k$) can be a left ear canal (e.g., the nasion and two ear canals can be expected to be exhibit stable or predictable distance ratios or subtended angle ratios).

In various aspects, the set of bounding boxes 302 can comprise a respective bounding box for each of the anthropometric landmark group 1102($k$), as shown by numeral 1202. In particular, the set of bounding boxes 302 can comprise a bounding box 302($k_1$) that corresponds to the anatomical landmark 106($k_1$), and the set of bounding boxes 302 can comprise a bounding box 302($k_m$) that corresponds to the anatomical landmark 106($k_m$). In various instances, the m bounding boxes denoted by numeral 1202 can exhibit a geometric interrelation 1204. As a non-limiting example, the geometric interrelation 1204 can be any suitable ratio of linear distances separating the centroids of any of the bounding boxes denoted by numeral 1202. As another non-limiting example, the geometric interrelation 1204 can be any suitable ratios of angular distances subtended by the centroids of any of the bounding boxes denoted by numeral 1202.

In various aspects, as mentioned above, the localization training dataset 110 can comprise a total of q training 3D voxel arrays that each depict some instantiation of the m landmarks in the anthropometric landmark group 1102 ($k$). Thus, as shown by numeral 1206, for each landmark of the anthropometric landmark group 1102($k$), the localization training dataset 110 can be considered as comprising a total of q ground-truth bounding boxes that correspond to that landmark. For example, as shown by numeral 1206($k_1$), the ground-truth bounding box 204(1)($k_1$) to the ground-truth bounding box 204($q$)($k_1$) can correspond to the anatomical landmark 106($k_1$) (e.g., the ground-truth bounding box 204(1)($k_1$) can indicate which voxels of the training 3D voxel array 202(1) are known or deemed to belong to the anatomical landmark 106($k_1$); the ground-truth bounding box 204($q$)($k_1$) can indicate which voxels of the training 3D voxel array 202($q$) are known or deemed to belong to the anatomical landmark 106($k_1$)). As another example, as shown by numeral 1206($k_m$), the ground-truth bounding box 204(1)($k_m$) to the ground-truth bounding box 204($q$)($k_m$) can correspond to the anatomical landmark 106($k_1$) (e.g., the ground-truth bounding box 204(1)($k_m$) can indicate which voxels of the training 3D voxel array 202(1) are known or deemed to belong to the anatomical landmark 106($k_m$); the ground-truth bounding box 204($q$)($k_m$) can indicate which voxels of the training 3D voxel array 202($q$) are known or deemed to belong to the anatomical landmark 106($k_m$)).

Thus, there can be a total of q*m ground-truth bounding boxes that correspond to the anthropometric landmark group 1102($k$). In various aspects, those q*m ground-truth bounding boxes can be regrouped or reorganized according to voxel array. For example, as shown by numeral 1208(1), the ground-truth bounding box 204(1)($k_1$) to the ground-truth bounding box 204(1)($k_m$) can be considered as collectively showing where the anthropometric landmark group 1102($k$) is known or deemed to be located within the training 3D voxel array 202(1). Likewise, as shown by numeral 1208($q$), the ground-truth bounding box 204($q$)($k_1$) to the ground-truth bounding box 204($q$)($k_m$) can be considered as collectively showing where the anthropometric landmark group 1102($k$) is known or deemed to be located within the training 3D voxel array 202($q$).

In various aspects, just as the bounding boxes denoted by numeral 1202 can exhibit the geometric interrelation 1204, each of the regrouped or reorganized ground-truth bounding boxes denoted by numerals 1208(1) to 1208($q$) can likewise exhibit a respective geometric interrelation. As a non-limiting example, the ground-truth bounding boxes denoted by the numeral 1208(1) can exhibit a geometric interrelation 1210(1) that can be analogous to the geometric interrelation 1204 (e.g., if the geometric interrelation 1204 is a ratio of linear distances separating various of the bounding boxes denoted by numeral 1202, then the geometric interrelation 1210(1) can likewise be an analogous ratio of linear distances separating various ones of the ground-truth bounding boxes denoted by numeral 1208(1); if the geometric interrelation 1204 is a ratio of angular distances subtended by various of the bounding boxes denoted by numeral 1202, then the geometric interrelation 1210(1) can likewise be an analogous ratio of angular distances subtended by various ones of the ground-truth bounding boxes denoted by numeral 1208(1)). As another non-limiting example, the ground-truth bounding boxes denoted by the numeral 1208 ($q$) can exhibit a geometric interrelation 1210($q$) that can be analogous to the geometric interrelation 1204. In various cases, the geometric interrelation 1210(1) to the geometric interrelation 1210($q$) can be collectively referred to as a set of geometric interrelations 1210.

In various aspects, the confidence component 120 can compute a group-wise confidence score 606($k$) in the set of group-wise confidence scores 606, based on how well or how poorly the geometric interrelation 1204 fits within a distribution formed by the set of geometric interrelations 1210. For instance, the distribution formed by the set of geometric interrelations 1210 can be defined by a mean value and a standard deviation value, and the confidence component 120 can determine the probability that the geometric interrelation 1204 comes from that distribution (e.g., based on how many standard deviations the geometric interrelation 1204 is from the mean). In various cases, the group-wise confidence score 606(*k*) can be equal to or otherwise based on that probability.

In this way, the confidence component 120 can compute a respective group-wise confidence score for each anthropometric group of the set of anatomical landmarks 106.

Figure 13:
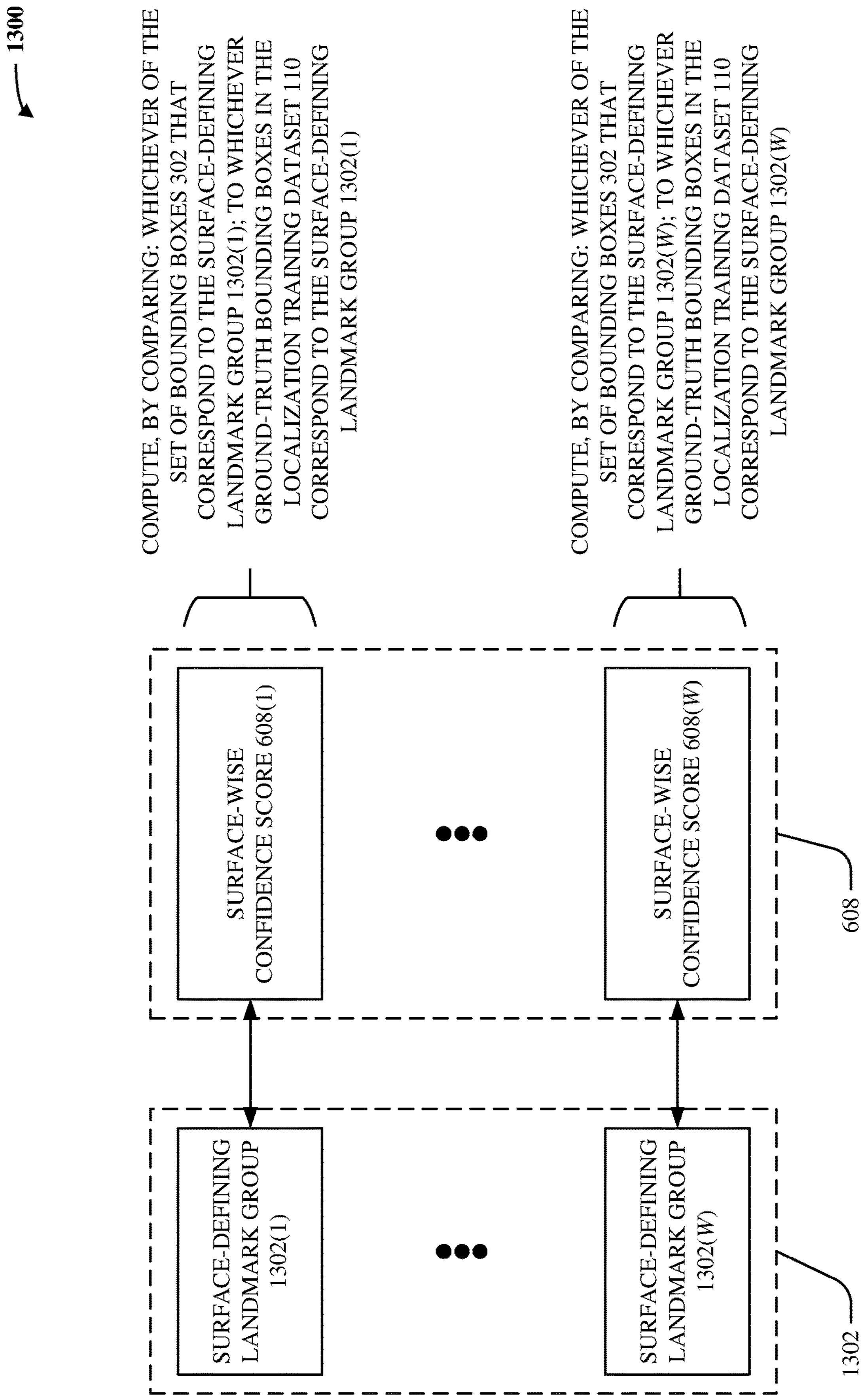
FIGS. 13-14 illustrate example, non-limiting block diagrams showing how surface-wise confidence scores of a multi-tiered confidence score collection can be computed in accordance with one or more embodiments described herein.
Figure 14:
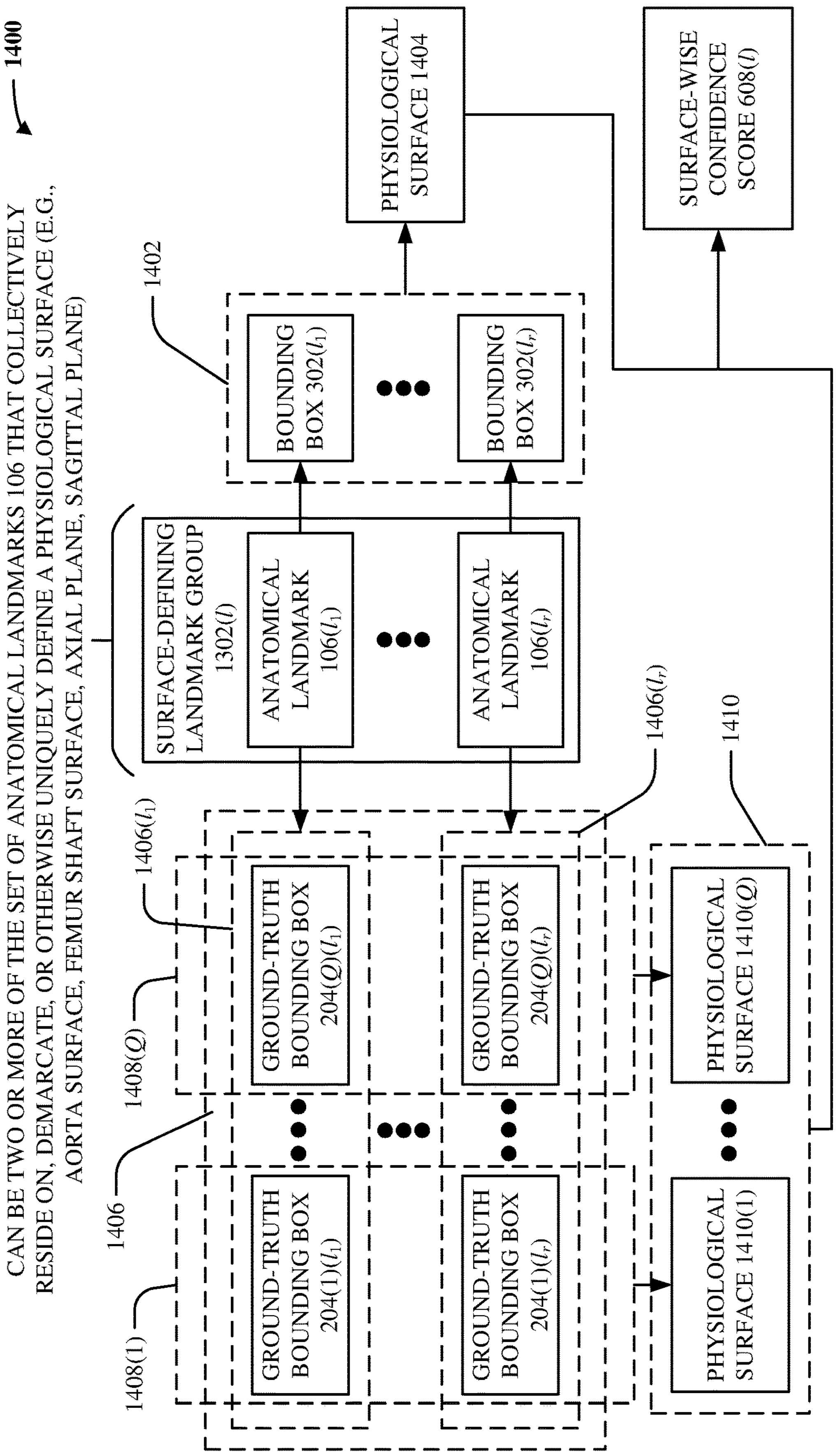

FIGS. 13-14 illustrate example, non-limiting block diagrams 1300 and 1400 showing how the set of surface-wise confidence scores 608 of the multi-tiered confidence score collection 502 can be computed in accordance with one or more embodiments described herein.

In various embodiments, as shown in FIG. 13, there can be a set of surface-defining landmark groups 1302. In various aspects, the set of surface-defining landmark groups 1302 can comprise w groups, for any suitable positive integer w: a surface-defining landmark group 1302(1) to a surface-defining landmark group 1302(*w*). In various instances, each of the set of surface-defining landmark groups 1302 can be any two or more landmarks from the set of anatomical landmarks 106 that are normally or usually expected to collectively reside on, demarcate, or otherwise delineate any suitable biologically-meaningful surface. As a non-limiting example, the surface-defining landmark group 1302(1) can be a first subset of the set of anatomical landmarks 106 that are expected to collectively mark a first physiological surface. As another non-limiting example, the surface-defining landmark group 1302(*w*) can be a w-th subset of the set of anatomical landmarks 106 that are expected to collectively mark a w-th physiological surface. Note that different ones of the set of surface-defining landmark groups 1302 can have the same or different total numbers of anatomical landmarks as each other.

In various aspects, as shown, the set of surface-wise confidence scores 608 can respectively correspond to the set of surface-defining landmark groups 1302. Thus, because the set of surface-defining landmark groups 1302 can comprise w groups, the set of surface-wise confidence scores 608 can comprise w scores: a surface-wise confidence score 608(1) to a surface-wise confidence score 608(*w*). In various aspects, each of the set of surface-wise confidence scores 608 can indicate whether or not the localizations predicted by the deep learning neural network 108 for a respective one of the set of surface-defining landmark groups 1302 collectively yield or call out whatever physiological surface that is expected for that respective one of the set of surface-defining landmark groups 1302.

As a non-limiting example, the surface-wise confidence score 608(1) can correspond to the surface-defining landmark group 1302(1). Accordingly, the confidence component 120 can compute the surface-wise confidence score 608(1), by comparing: a physiological surface that is actually demarcated by whichever of the set of bounding boxes 302 correspond to the surface-defining landmark group 1302(1); to analogous physiological surfaces that are actually demarcated by whichever ground-truth bounding boxes in the localization training dataset 110 correspond to the surface-defining landmark group 1302(1).

As another non-limiting example, the surface-wise confidence score 608(*w*) can correspond to the surface-defining landmark group 1302(*w*). So, the confidence component 120 can compute the surface-wise confidence score 608(*w*), by comparing: a physiological surface that is actually demarcated by whichever of the set of bounding boxes 302 correspond to the surface-defining landmark group 1302(*w*); to analogous physiological surfaces that are actually demarcated by whichever ground-truth bounding boxes in the localization training dataset 110 correspond to the surface-defining landmark group 1302(*w*).

Consider, FIG. 14, which illustrates a non-limiting example of how a surface-wise confidence score can be computed.

In various embodiments, there can be a surface-defining landmark group 1302(*l*) in the set of surface-defining landmark groups 1302, for any suitable positive integer $1 \leq l \leq w$. In various aspects, as shown, the surface-defining landmark group 1302(*l*) can comprise a total of r landmarks from the set of anatomical landmarks 106: an anatomical landmark 106($l_1$) to an anatomical landmark 106($l_r$), for any suitable positive integers $1 \leq l_1 < \ldots < l_r \leq n$. In various instances, such r anatomical landmarks can be any suitable landmarks that are expected or supposed to be collectively located on a particular biologically-meaningful surface or plane of a medical patient. As a non-limiting example, the r landmarks of the surface-defining landmark group 1302(*l*) can all be distinct bony landmarks of a skull. Accordingly, the r landmarks of the surface-defining landmark group 1302(*l*) can thus be considered as defining or demarcating a cranial surface of the skull. As another non-limiting example, the r landmarks of the surface-defining landmark group 1302(*l*) can all be distinct landmarks that reside in a sagittal plane of a medical patient. Accordingly, the r landmarks of the surface-defining landmark group 1302(*l*) can thus be considered as defining or demarcating that sagittal plane.

In various aspects, the set of bounding boxes 302 can comprise a respective bounding box for each of the surface-defining landmark group 1302(*l*), as shown by numeral 1402. In particular, the set of bounding boxes 302 can comprise a bounding box 302($l_1$) that corresponds to the anatomical landmark 106($l_1$), and the set of bounding boxes 302 can comprise a bounding box 302($l_r$) that corresponds to the anatomical landmark 106($l_r$). In various instances, the r bounding boxes denoted by numeral 1402 can all reside on, demarcate, or call out a physiological surface 1404 of the 3D voxel array 104. In various instances, the physiological surface 1404 can be considered as being an inferred approximation of whatever biologically-meaningful surface or plane that the surface-defining landmark group 1302(*l*) is supposed or expected to demarcate.

In various aspects, as mentioned above, the localization training dataset 110 can comprise a total of q training 3D voxel arrays that each depict some instantiation of the r landmarks in the surface-defining landmark group 1302 (*l*). Thus, as shown by numeral 1406, for each landmark of the surface-defining landmark group 1302(*l*), the localization training dataset 110 can be considered as comprising a total of q ground-truth bounding boxes that correspond to that landmark. For example, as shown by numeral 1406($l_1$), the ground-truth bounding box 204(1)($l_1$) to the ground-truth bounding box 204(*q*)($l_1$) can correspond to the anatomical landmark 106($l_1$) (e.g., the ground-truth bounding box 204(1)($l_1$) can indicate which voxels of the training 3D voxel array 202(1) are known or deemed to belong to the anatomical landmark 106($l_1$); the ground-truth bounding box 204(*q*)($l_1$) can indicate which voxels of the training 3D voxel array 202(*q*) are known or deemed to belong to the anatomical landmark 106($l_1$)). As another example, as shown by numeral 1206($l_r$), the ground-truth bounding box 204(1)($l_r$) to the ground-truth bounding box 204(*q*)($l_r$) can correspond to the anatomical landmark 106($l_r$) (e.g., the ground-truth bounding box 204(1)($l_r$) can indicate which voxels of the training 3D voxel array 202(1) are known or deemed to belong to the anatomical landmark 106($l_r$); the ground-truth bounding box 204($q$)($l_y$) can indicate which voxels of the training 3D voxel array 202($q$) are known or deemed to belong to the anatomical landmark 106($l_r$)).

Thus, there can be a total of q*r ground-truth bounding boxes that correspond to the surface-defining landmark group 1302($l$). In various aspects, those q*r ground-truth bounding boxes can be regrouped or reorganized according to voxel array. For example, as shown by numeral 1408(1), the ground-truth bounding box 204(1)($l_1$) to the ground-truth bounding box 204(1)($l_r$) can be considered as collectively showing where the surface-defining landmark group 1302($l$) is known or deemed to be located within the training 3D voxel array 202(1). Likewise, as shown by numeral 1408($q$), the ground-truth bounding box 204($q$)($l_1$) to the ground-truth bounding box 204($q$)($l_r$) can be considered as collectively showing where the surface-defining landmark group 1302($l$) is known or deemed to be located within the training 3D voxel array 202($q$).

In various aspects, just as the bounding boxes denoted by numeral 1402 can demarcate the physiological surface 1404 in the 3D voxel array 104, each of the regrouped or reorganized ground-truth bounding boxes denoted by numerals 1408(1) to 1408($q$) can likewise demarcate a respective physiological surface in a respective one of the plurality of training 3D voxel arrays 202. As a non-limiting example, the ground-truth bounding boxes denoted by the numeral 1408(1) can reside on or demarcate, within the training 3D voxel array 202(1), a physiological surface 1410(1) that can be analogous to the physiological surface 1404 (e.g., if the physiological surface 1404 is purportedly a cranial surface of a skull depicted in the 3D voxel array 104, then the physiological surface 1410(1) can likewise be a cranial surface of a skull depicted in the training 3D voxel array 202(1); if the physiological surface 1404 is purportedly a sagittal plane of the 3D voxel array 104, then the physiological surface 1410(1) can likewise be a sagittal plane of the training 3D voxel array 202(1)). As another non-limiting example, the ground-truth bounding boxes denoted by the numeral 1408($q$) can reside on or demarcate, within the training 3D voxel array 202($q$), a physiological surface 1410($q$) that can be analogous to the physiological surface 1404. In various cases, the physiological surface 1410(1) to the physiological surface 1410($q$) can be collectively referred to as a set of physiological surfaces 1410.

In various aspects, the confidence component 120 can compute a surface-wise confidence score 608($l$) in the set of surface-wise confidence scores 608, based on how well or how poorly any suitable feature (e.g., intensity gradient) of the physiological surface 1404 fits within a distribution of features formed by the set of physiological surfaces 1410. For instance, the distribution of features formed by the set of physiological surfaces 1410 can be defined by a mean value and a standard deviation value, and the confidence component 120 can determine the probability that the feature of the physiological surface 1404 comes from that distribution (e.g., based on how many standard deviations that feature of the physiological surface 1404 is from the mean). In various cases, the surface-wise confidence score 608($l$) can be equal to or otherwise based on that probability.

In this way, the confidence component 120 can compute a respective surface-wise confidence score for each surface-defining group of the set of anatomical landmarks 106.

Accordingly, as described herein, any given anatomical landmark localized by the deep learning neural network 108 can be associated with one or more confidence scores. For example, such given anatomical landmark can be associated with a landmark-wise confidence score. Moreover, if that given anatomical landmark belongs to an anatomically symmetric pair, then that given anatomical landmark can also be associated with a pair-wise confidence score. Furthermore, if that given anatomical landmark belongs to an anthropometric group, then that given anatomical landmark can also be associated with a group-wise confidence score. Further still, if that given anatomical landmark belongs to a surface-defining group, then that given anatomical landmark can also be associated with a surface-wise confidence score.

In any of such cases, the different confidence scores of that given anatomical landmark can be considered as capturing or reflecting different avenues, modes, or indicators of improper localization. For example, a low landmark-wise confidence score can indicate improper individual localization of that given anatomical landmark. As another example, a low pair-wise confidence score can indicate a lack of expected symmetry associated with that given anatomical landmark, even if that given anatomical landmark has a high landmark-wise confidence score. As yet another example, a low group-wise confidence score can indicate an unexpected relative positioning of that given anatomical landmark, even if that given anatomical landmark has a high landmark-wise or pair-wise confidence score. As still another example, a low surface-wise confidence score can indicate an unexpected absolute positioning of that given anatomical landmark, even if that given anatomical landmark has a high landmark-wise, pair-wise, or group-wise confidence score.

Figure 15:
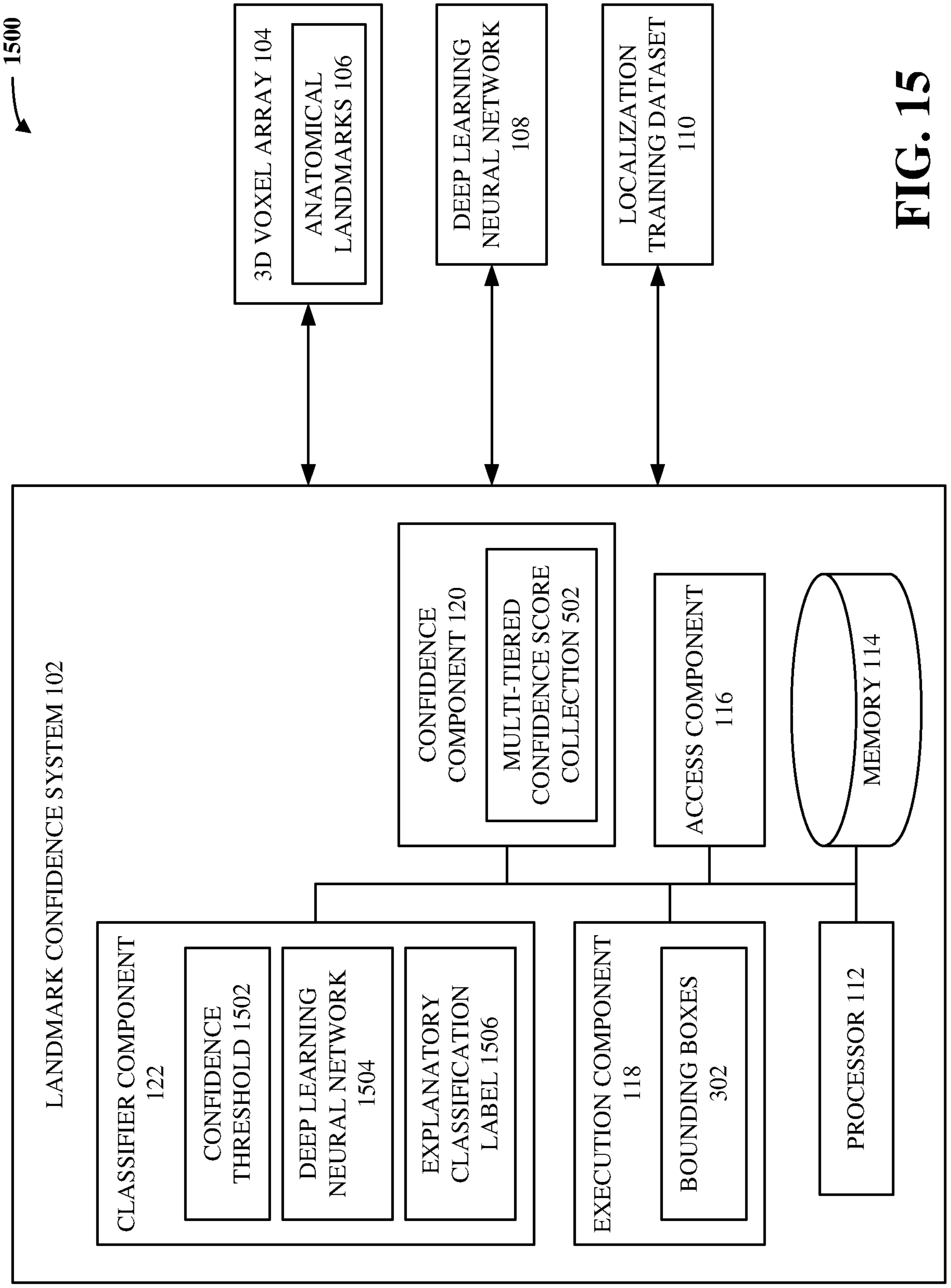
FIG. 15 illustrates a block diagram of an example, non-limiting system including a confidence threshold, a classifier neural network, and an explanatory classification label that facilitates explainable confidence estimation for landmark localization in accordance with one or more embodiments described herein.

FIG. 15 illustrates a block diagram of an example, non-limiting system 1500 including a confidence threshold, a deep learning neural network, and an explanatory classification label that can facilitate explainable confidence estimation for landmark localization in accordance with one or more embodiments described herein. As shown, the system 1500 can, in various cases, comprise the same components as the system 500, and can further comprise a confidence threshold 1502, a deep learning neural network 1504, and an explanatory classification label 1506.

In various embodiments, the confidence threshold 1502 can be any suitable scalar value against which a confidence score can be compared. In various aspects, the classifier component 122 can electronically determine whether any confidence score in the multi-tiered confidence score collection 502 fails to satisfy (e.g., is less than) the confidence threshold 1502.

If no confidence scores in the multi-tiered confidence score collection 502 fails to satisfy the confidence threshold 1502, then the landmark confidence system 102 can electronically transmit any of the set of bounding boxes 302 to any suitable computing device (not shown), and the landmark confidence system 102 can accompany such transmission with an electronic message indicating that such bounding boxes are suitable for use in downstream inferencing tasks (e.g., image alignment, surgical planning).

However, if one or more confidence scores in the multi-tiered confidence score collection 502 fail to satisfy the confidence threshold 1502, then the landmark confidence system 102 can electronically transmit to any suitable computing device (not shown) an electronic message indicating that the set of bounding boxes 302 (or a subset thereof) are not suitable for use in downstream inferencing tasks. Moreover, in such case, the classifier component 122 can electronically generate the explanatory classification label 1506, by executing the deep learning neural network 1504 on the 3D voxel array 104 and on the multi-tiered confidence score collection 502 (or a portion thereof). Non-limiting aspects are described with respect to FIG. 16.

Figure 16:
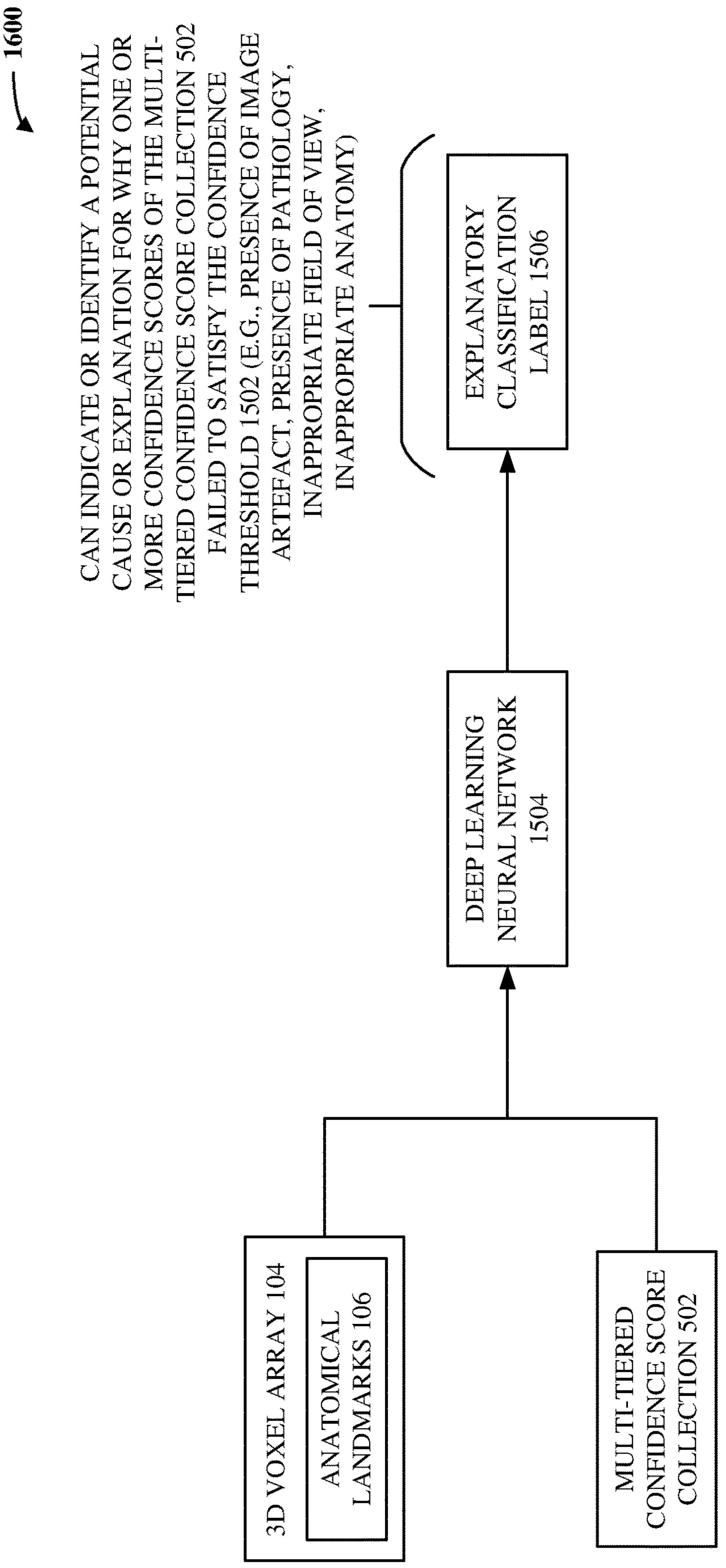
FIG. 16 illustrates an example, non-limiting block diagram showing how an explanatory classification label can be generated in accordance with one or more embodiments described herein.

FIG. 16 illustrates an example, non-limiting block diagram 1600 showing how the explanatory classification label 1506 can be generated in accordance with one or more embodiments described herein.

In various embodiments, the classifier component 122 can electronically store, electronically maintain, electronically control, or otherwise electronically access the deep learning neural network 1504. In various aspects, the deep learning neural network 1504 can be any suitable artificial neural network that can have or otherwise exhibit any suitable internal architecture. For instance, the deep learning neural network 1504 can have an input layer, one or more hidden layers, and an output layer. In various instances, any of such layers can be coupled together by any suitable interneuron connections or interlayer connections, such as forward connections, skip connections, or recurrent connections. Furthermore, in various cases, any of such layers can be any suitable types of neural network layers having any suitable learnable or trainable internal parameters. For example, any of such input layer, one or more hidden layers, or output layer can be convolutional layers, whose learnable or trainable parameters can be convolutional kernels. As another example, any of such input layer, one or more hidden layers, or output layer can be dense layers, whose learnable or trainable parameters can be weight matrices or bias values. As still another example, any of such input layer, one or more hidden layers, or output layer can be batch normalization layers, whose learnable or trainable parameters can be shift factors or scale factors. Further still, in various cases, any of such layers can be any suitable types of neural network layers having any suitable fixed or non-trainable internal parameters. For example, any of such input layer, one or more hidden layers, or output layer can be non-linearity layers, padding layers, pooling layers, or concatenation layers.

In various aspects, the deep learning neural network 1504 can be configured to produce classification labels for inputted voxel arrays and corresponding confidence scores. Accordingly, as shown, the classifier component 122 can, in various instances, electronically execute the deep learning neural network 1504 on the 3D voxel array 104 and on the multi-tiered confidence score collection 502 (or any suitable portion thereof, such as only whichever confidence scores fail to satisfy the confidence threshold 1502). In various cases, such execution can cause the deep learning neural network 1504 to produce the explanatory classification label 1506. More specifically, the classifier component 122 can concatenate the 3D voxel array 104 and the multi-tiered confidence score collection 502 (or any suitable portion thereof) together. In various instances, the classifier component 122 can feed that concatenation to an input layer of the deep learning neural network 1504. In various aspects, that concatenation can complete a forward pass through one or more hidden layers of the deep learning neural network 1504. In various instances, an output layer of the deep learning neural network 1504 can compute or otherwise calculate the explanatory classification label 1506 based on activation maps generated by the one or more hidden layers of the deep learning neural network 1504.

In any case, the explanatory classification label 1506 can be any suitable classification label that indicates, identifies, or otherwise conveys one or more substantive reasons that can explain or justify why some of the multi-tiered confidence score collection 502 failed to satisfy the confidence threshold 1502. In other words, the failure of one or more confidence scores in the multi-tiered confidence score collection 502 can be considered as indicating that the deep learning neural network 108 was unable to localize the set of anatomical landmarks 106 in the 3D voxel array 104 with full confidence, and the explanatory classification label 1506 can be considered as explaining what potentially could have caused the deep learning neural network 108 to be unable to localize the set of anatomical landmarks 106 in the 3D voxel array 104 with full confidence.

In various cases, the reason or explanation indicated by the explanatory classification label 1506 can be any suitable fact that is substantively related or otherwise pertinent to the visual content of the 3D voxel array 104. As a non-limiting example, the reason or explanation indicated by the explanatory classification label 1506 can be that the deep learning neural network 108 was thrown off or distracted by one or more imaging artifacts or acquisition artifacts (e.g., unusual glares, scratches, shadows, distortions, motion-induced deformations) that are present in the 3D voxel array 104. As another non-limiting example, the reason or explanation indicated by the explanatory classification label 1506 can be that the deep learning neural network 108 was thrown off or distracted by one or more anatomical pathologies (e.g., visible symptoms such as fractures, tumors, foreign bodies, or surgical implants) that are present in the 3D voxel array 104. As even another non-limiting example, the reason or explanation indicated by the explanatory classification label 1506 can be that the deep learning neural network 108 was thrown off or distracted by an improper, inappropriate, unexpected, out-of-scope, or otherwise incorrect field of view of the 3D voxel array 104 (e.g., the 3D voxel array 104 can have been captured or generated using a field of view that is excessively zoomed-in or excessively zoomed-out). Note that an improper, inappropriate, unexpected, out-of-scope, or otherwise incorrect field of view can be considered as any field of view which the deep learning neural network 108 was not trained to handle. As still another non-limiting example, the reason or explanation indicated by the explanatory classification label 1506 can be that the deep learning neural network 108 was thrown off or distracted by an improper, inappropriate, unexpected, out-of-scope, or otherwise incorrect radiation or power dosage of the 3D voxel array 104 (e.g., the 3D voxel array 104 can have been captured or generated using a radiation or power dosage that is excessively high or excessively low). Note that an improper, inappropriate, unexpected, out-of-scope, or otherwise incorrect radiation or power dosage can be considered as any radiation or power dosage which the deep learning neural network 108 was not trained to handle. As yet another non-limiting example, the reason or explanation indicated by the explanatory classification label 1506 can be that the 3D voxel array 104 does not actually depict any of the set of anatomical landmarks 106. In other words, the reason or explanation indicated by the explanatory classification label 1506 can be that the 3D voxel array 104 depicts an improper, inappropriate, unexpected, out-of-scope, or otherwise incorrect anatomy (e.g., head-related landmarks cannot be localized within an image of a patient's foot; foot-related landmarks cannot be localized within an image of a patient's head). Note that an improper, inappropriate, unexpected, out-of-scope, or otherwise incorrect anatomy can be considered as any anatomy which the deep learning neural network 108 was not trained to handle. As yet another non-limiting example, the reason or explanation indicated by the explanatory classification label 1506 can be any suitable combination of the aforementioned. Furthermore, note that the above reasons or explanations are mere non-limiting examples, and note that a reason or explanation indicated by the explanatory classification label 1506 can be any other suitable characteristic, attribute, or property of the 3D voxel array 104 that is unusual, unexpected, non-standard, or otherwise not what the deep learning neural network 108 was trained to handle or analyze.

In any case, in response to one or more confidence scores in the multi-tiered confidence score collection 502 failing to satisfy the confidence threshold 1502, the classifier component 122 can generate the explanatory classification label 1506. In various aspects, the classifier component 122 can electronically render the explanatory classification label 1506 on any suitable electronic display (e.g., computer screen, computer monitor). In various instances, the classifier component 122 can electronically transmit the explanatory classification label 1506 to any other suitable computing device (not shown). Accordingly, a user or operator associated with the deep learning neural network 108 can be notified not only that the deep learning neural network 108 was unable to localize the set of anatomical landmarks 106 within the 3D voxel array 104 with sufficient confidence, but also can be notified of a reason or explanation for why the deep learning neural network 108 was unable to localize the set of anatomical landmarks 106 within the 3D voxel array 104 with sufficient confidence.

Figure 17:
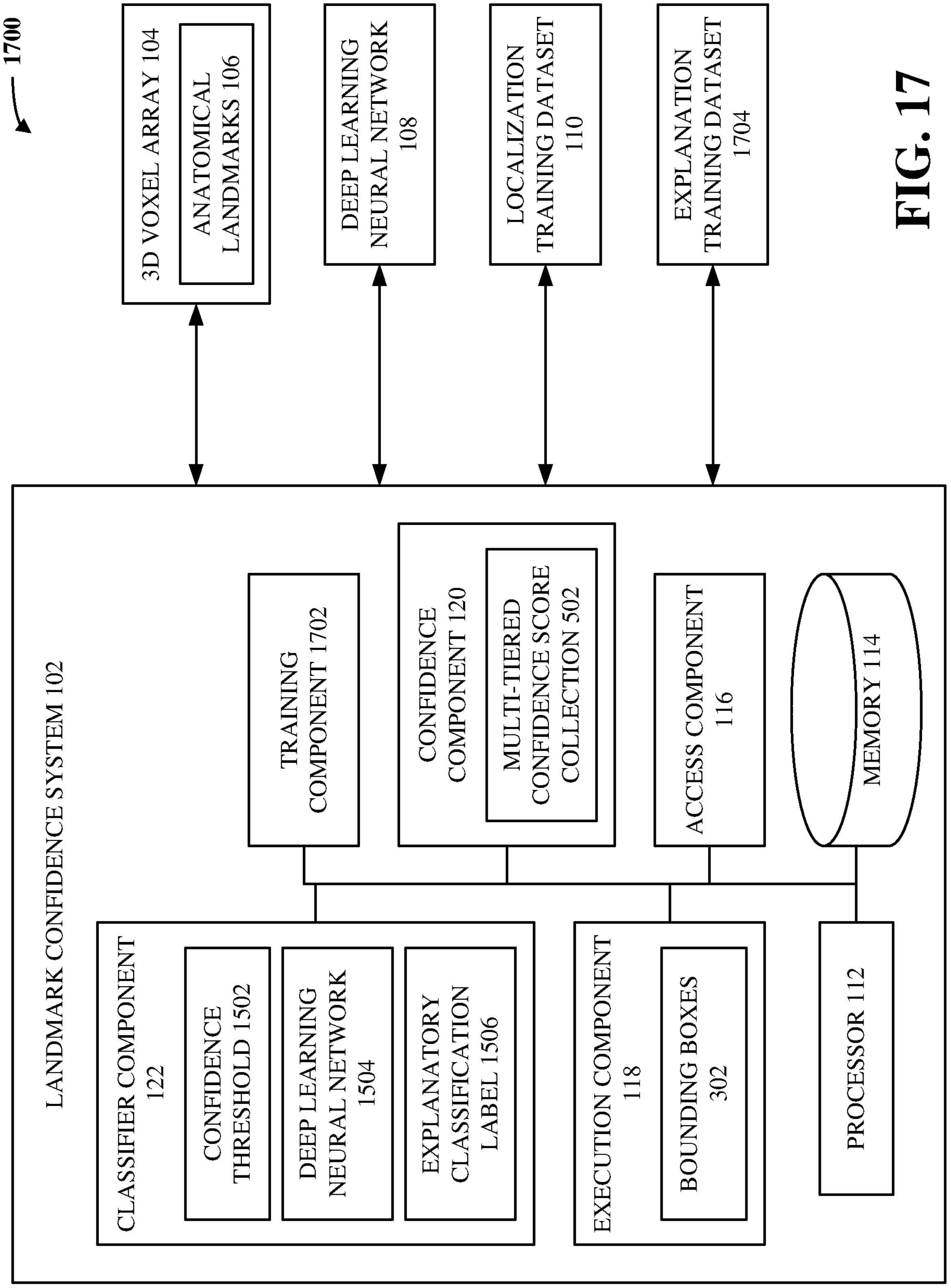
FIG. 17 illustrates a block diagram of an example, non-limiting system including a training component and an explanation training dataset that facilitates explainable confidence estimation for landmark localization in accordance with one or more embodiments described herein.
Figure 18:
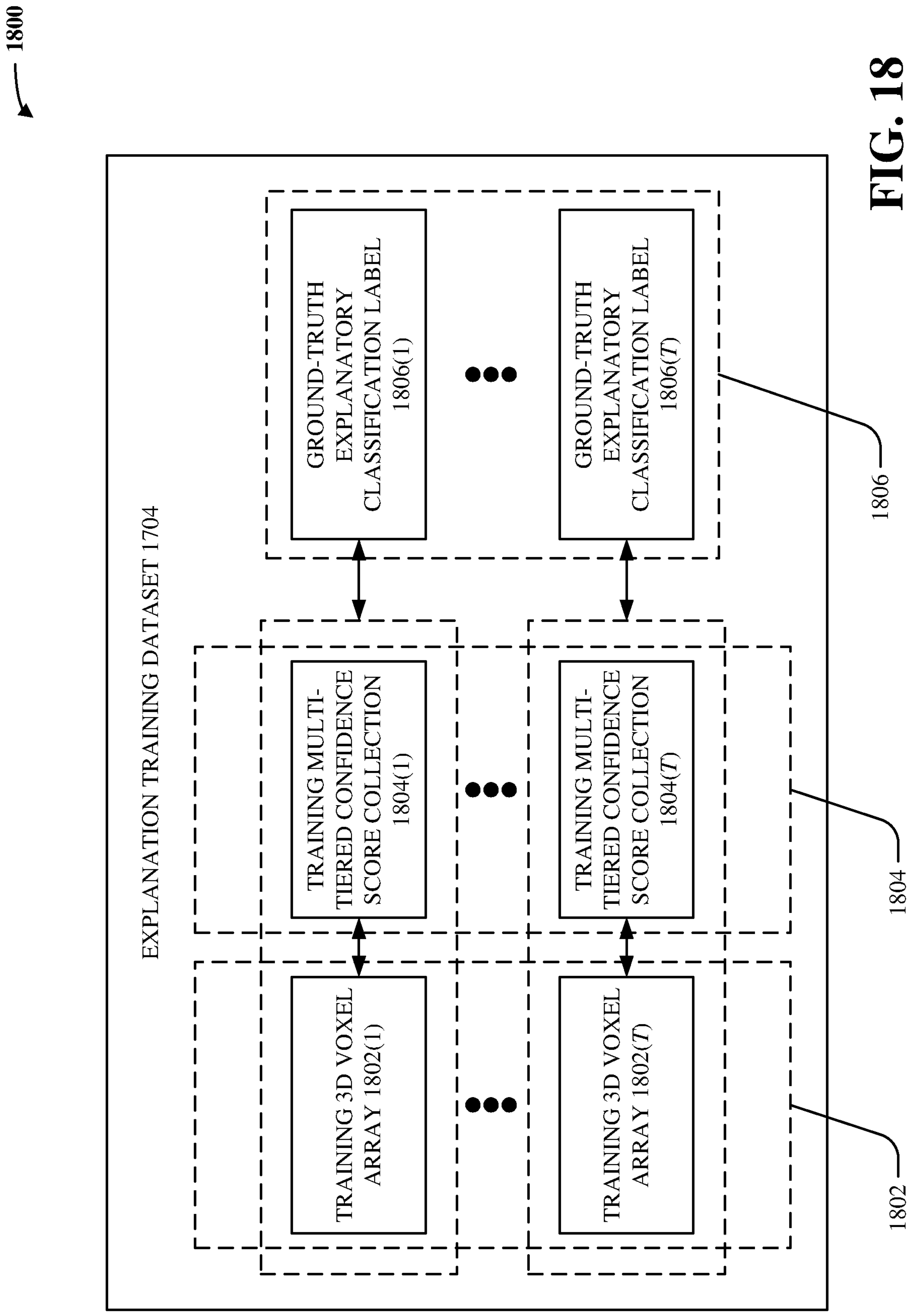
FIG. 18 illustrates an example, non-limiting block diagram of an explanation training dataset in accordance with one or more embodiments described herein.
Figure 19:
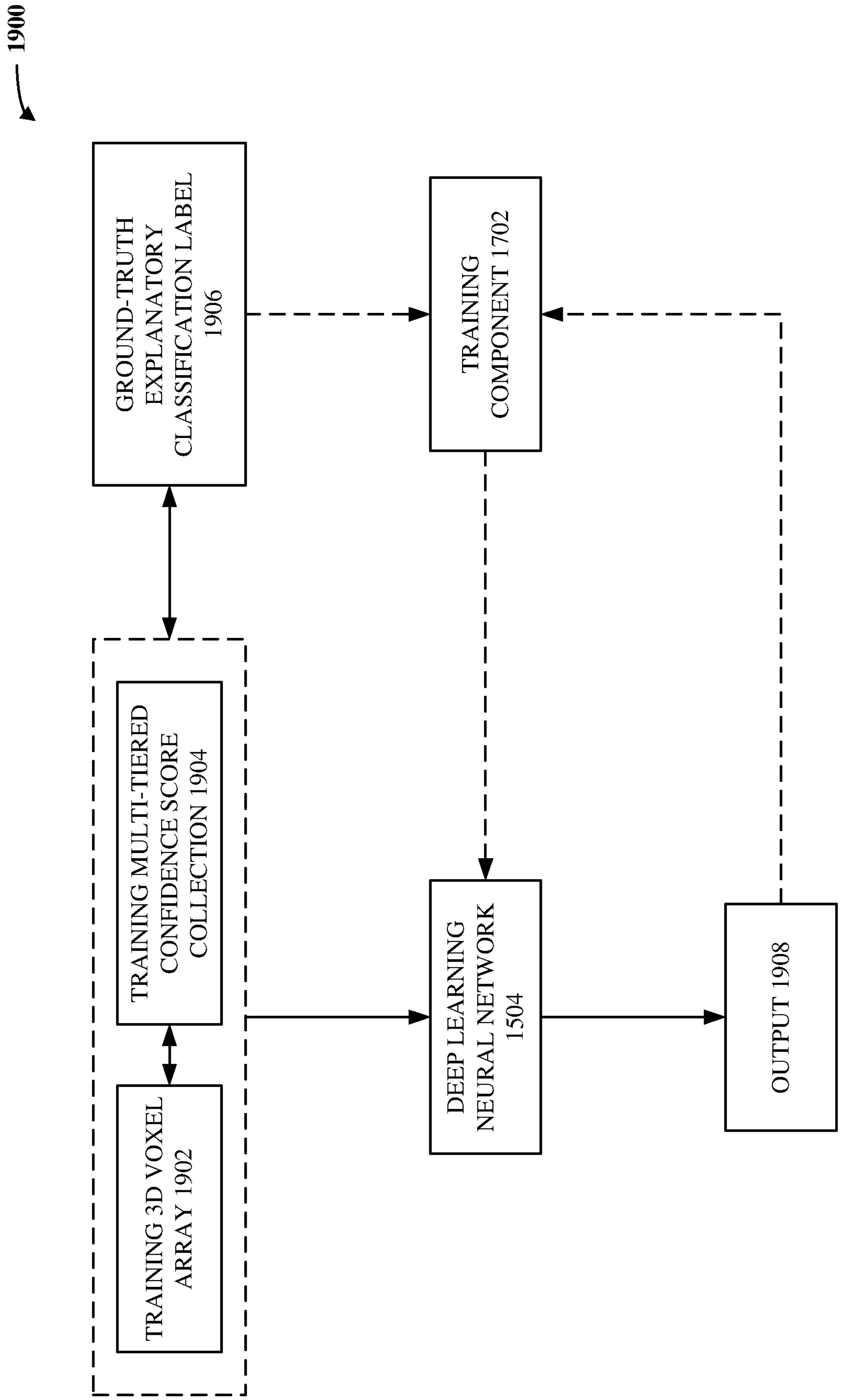
FIG. 19 illustrates an example, non-limiting block diagram showing how a classifier neural network can be trained on an explanation training dataset in accordance with one or more embodiments described herein.

In order for the explanatory classification label 1506 to be accurate or reliable, the deep learning neural network 1504 can first undergo training, as described with respect to FIGS. 17-19.

FIG. 17 illustrates a block diagram of an example, non-limiting system 1700 including a training component and an explanation training dataset that can facilitate explainable confidence estimation for landmark localization in accordance with one or more embodiments described herein. As shown, the system 1700 can, in some cases, comprise the same components as the system 1500, and can further comprise a training component 1702 and an explanation training dataset 1704.

In various embodiments, the access component 116 can electronically receive, retrieve, or otherwise access, from any suitable source, the explanation training dataset 1704. In various aspects, the training component 1702 can train the deep learning neural network 1504 on the explanation training dataset 1704 in supervised fashion. Non-limiting aspects of such training are described with respect to FIGS. 18-19.

FIG. 18 illustrates an example, non-limiting block diagram 1800 of the explanation training dataset 1704 in accordance with one or more embodiments described herein.

As shown, the explanation training dataset 1704 can comprise a plurality of training 3D voxel arrays 1802. In various aspects, the plurality of training 3D voxel arrays 1802 can comprise t voxel arrays, for any suitable positive integer t: a training 3D voxel array 1802(1) to a training 3D voxel array 1802(*t*). In various instances, each of the plurality of training 3D voxel arrays 1802 can exhibit the same format, size, or dimensionality as the 3D voxel array 104. For example, if the 3D voxel array 104 is an x-by-y-by-z voxel array, then each of the plurality of training 3D voxel arrays 1802 can likewise be an x-by-y-by-z voxel array.

In various cases, as shown, the explanation training dataset 1704 can comprise a plurality of training multi-tiered confidence score collections 1804. In various aspects, the plurality of training multi-tiered confidence score collections 1804 can respectively correspond to the plurality of training 3D voxel arrays 1802. Thus, since the plurality of training 3D voxel arrays 1802 can comprise t arrays, the plurality of training multi-tiered confidence score collections 1804 can comprise t collections: a training multi-tiered confidence score collection 1804(1) to a training multi-tiered confidence score collection 1804(*t*). In various instances, each of the plurality of training multi-tiered confidence score collections 1804 can have the same format, size, or dimensionality as the multi-tiered confidence score collection 502. In other words, each of the plurality of training multi-tiered confidence score collections 1804 can be considered as being whatever multi-tiered confidence scores that have been computed for, or that are otherwise known or deemed to correspond to, a respective one of the plurality of training 3D voxel arrays 1802. As a non-limiting example, the training multi-tiered confidence score collection 1804(1) can by whatever multi-tiered confidence scores that have been computed for the training 3D voxel array 1802(1). As another non-limiting example, the training multi-tiered confidence score collection 1804(*t*) can by whatever multi-tiered confidence scores that have been computed for the training 3D voxel array 1802(*t*).

In various aspects, as shown, the explanation training dataset 1704 can comprise a set of ground-truth explanatory classification labels 1806. In various instances, the set of ground-truth explanatory classification labels 1806 can respectively correspond (e.g., in one-to-one fashion) to the plurality of training 3D voxel arrays 1802 and to the plurality of training multi-tiered confidence score collections 1804. Accordingly, since the plurality of training 3D voxel arrays 1802 can comprise t arrays, and since the plurality of training multi-tiered confidence score collections 1804 can comprise t collections, the set of ground-truth explanatory classification labels 1806 can comprise t labels: a ground-truth explanatory classification label 1806(1) to a ground-truth explanatory classification label 1806(*t*). In various cases, each of the set of ground-truth explanatory classification labels 1806 can be considered as a correct or accurate explanatory classification label that is known or deemed to correspond to a respective one of the plurality of training 3D voxel arrays 1802 and to a respective one of the plurality of training multi-tiered confidence score collections 1804.

As a non-limiting example, the ground-truth explanatory classification label 1806(1) can correspond to the training 3D voxel array 1802(1) and to the training multi-tiered confidence score collection 1804(1). Accordingly, the ground-truth explanatory classification label 1806(1) can indicate whatever substantive reason pertaining to the training 3D voxel array 1802(1) that is known or deemed to explain why one or more (if any) confidence scores of the training multi-tiered confidence score collection 1804(1) failed to satisfy the confidence threshold 1502.

As another non-limiting example, the ground-truth explanatory classification label 1806(*t*) can correspond to the training 3D voxel array 1802(*t*) and to the training multi-tiered confidence score collection 1804(*t*). So, the ground-truth explanatory classification label 1806(*t*) can indicate whatever substantive reason pertaining to the training 3D voxel array 1802(*t*) that is known or deemed to explain why one or more (if any) confidence scores of the training multi-tiered confidence score collection 1804(*t*) failed to satisfy the confidence threshold 1502.

FIG. 19 illustrates an example, non-limiting block diagram 1900 showing how the deep learning neural network

1504 can be trained on the explanation training dataset 1704 in accordance with one or more embodiments described herein.

In various embodiments, prior to beginning training, the training component 1702 can electronically initialize the trainable internal parameters (e.g., weight matrices, bias values, convolutional kernels) of the deep learning neural network 1504 in any suitable fashion (e.g., random initialization).

In various aspects, the training component 1702 can electronically select any voxel array, corresponding multi-tiered confidence score collection, and corresponding ground-truth label from the explanation training dataset 1704. These can respectively be referred to as a training 3D voxel array 1902, a training multi-tiered confidence score collection 1904, and a ground-truth explanatory classification label 1906.

In various instances, the training component 1702 can execute the deep learning neural network 1504 on both the training 3D voxel array 1902 and the training multi-tiered confidence score collection 1904 (or any suitable portion thereof, such as only those confidence scores that fail to satisfy the confidence threshold 1502). In various instances, this can cause the deep learning neural network 1504 to produce an output 1908. More specifically, the training component 1702 can concatenate the training 3D voxel array 1902 and the training multi-tiered confidence score collection 1904 (or any suitable portion thereof) together. In various instances, the training component 1702 can feed that concatenation to the input layer of the deep learning neural network 1504. In various cases, that concatenation can complete a forward pass through the one or more hidden layers of the deep learning neural network 1504. Accordingly, the output layer of the deep learning neural network 1504 can compute or calculate the output 1908 based on activation maps produced by the one or more hidden layers of the deep learning neural network 1504.

Note that, in various cases, the format, size, or dimensionality of the output 1908 can be controlled or otherwise determined by the number, arrangement, or sizes of neurons or other internal parameters (e.g., convolutional kernels) that are contained in or that otherwise make up the output layer (or any other layer) of the deep learning neural network 1504. Thus, the output 1908 can be forced to have any desired format, size, or dimensionality by adding, removing, or otherwise adjusting neurons or other internal parameters to, from, or within the output layer (or any other layer) of the deep learning neural network 1504.

In any case, the output 1908 can be considered as being whatever explanatory classification label that the deep learning neural network 1504 has inferred or predicted based on the training 3D voxel array 1902 and based on the training multi-tiered confidence score collection 1904. In contrast, the ground-truth explanatory classification label 1906 can be the correct or accurate label that is known or deemed to correspond to the training 3D voxel array 1902 and to the training multi-tiered confidence score collection 1904. Note that, if the deep learning neural network 1504 has so far undergone no or little training, then the output 1908 can be highly inaccurate (e.g., can be very different from the ground-truth explanatory classification label 1906).

In various aspects, the training component 1702 can compute an error or loss (e.g., MAE, MSE, cross-entropy) between the output 1908 and the ground-truth explanatory classification label 1906. In various instances, as shown, the training component 1702 can incrementally update the trainable internal parameters of the deep learning neural network 1504, by performing backpropagation (e.g., stochastic gradient descent) driven by the computed error or loss.

In various cases, the training component 1702 can repeat the above-described training procedure for any suitable number of training 3D voxel arrays (e.g., for all of the training 3D voxel arrays in the explanation training dataset 1704). This can ultimately cause the trainable internal parameters of the deep learning neural network 1504 to become iteratively optimized for accurately inferring explanatory classification labels based on inputted voxel arrays and corresponding confidence scores. In various aspects, the training component 1702 can implement any suitable training batch sizes, any suitable training termination criterion, or any suitable error, loss, or objective function to train the deep learning neural network 1504.

Although the herein disclosure has mainly described how the deep learning neural network 1504 can be trained in a supervised fashion, this is a mere non-limiting example. In various other embodiments, the deep learning neural network 1504 can instead be trained in any other suitable fashion (e.g., via unsupervised learning, via reinforcement learning).

Figure 20:
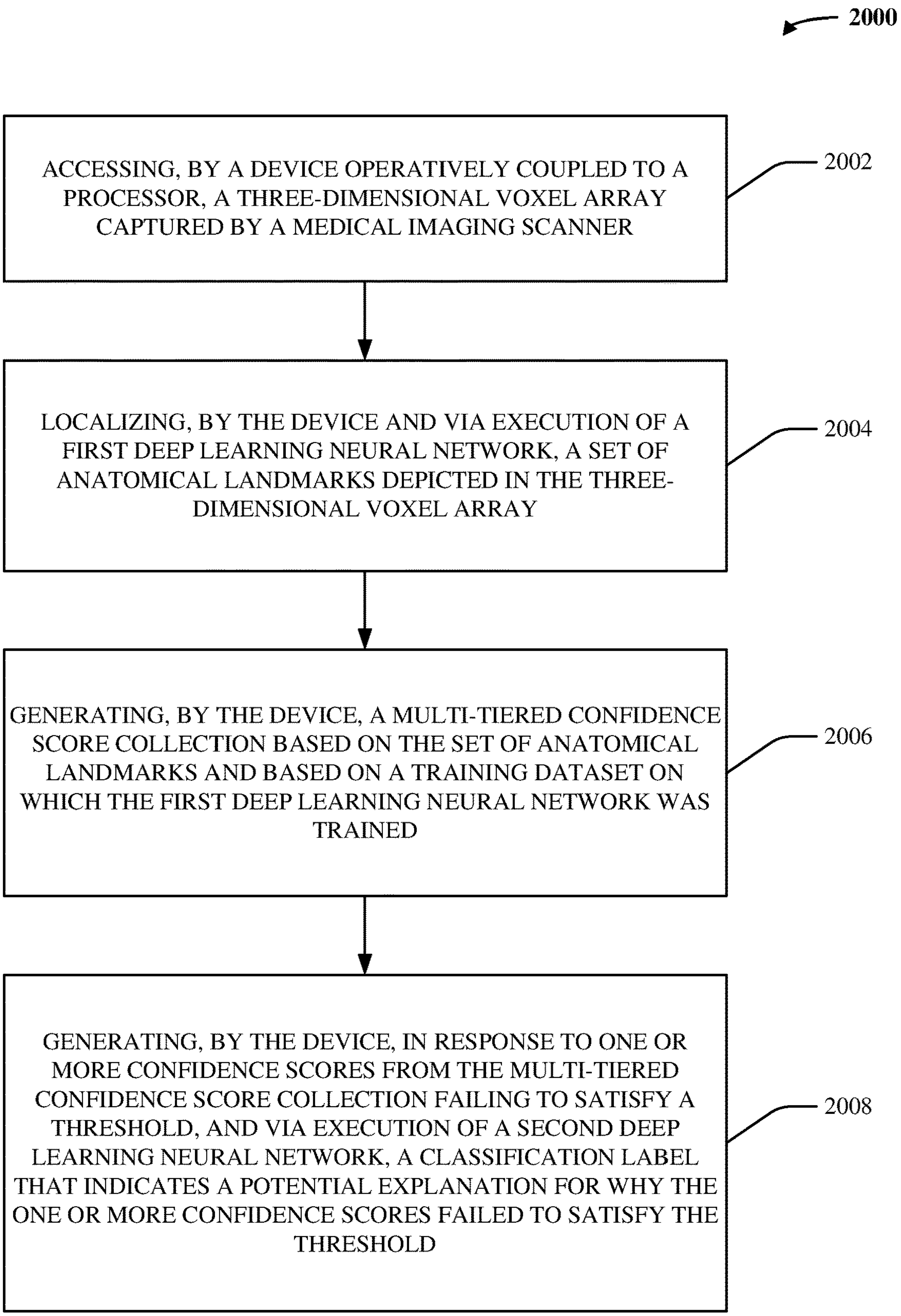
FIG. 20 illustrates a flow diagram of an example, non-limiting computer-implemented method that facilitates explainable confidence estimation for landmark localization in accordance with one or more embodiments described herein.

FIG. 20 illustrates a flow diagram of an example, non-limiting computer-implemented method 2000 that can facilitate explainable confidence estimation for landmark localization in accordance with one or more embodiments described herein. In various cases, the landmark confidence system 102 can facilitate the computer-implemented method 2000.

In various embodiments, act 2002 can include accessing, by a device (e.g., via 116) operatively coupled to a processor (e.g., 112), a three-dimensional voxel array (e.g., 104) captured by a medical imaging scanner.

In various aspects, act 2004 can include localizing, by the device (e.g., via 118) and via execution of a first deep learning neural network (e.g., 108), a set of anatomical landmarks (e.g., 106) depicted in the three-dimensional voxel array.

In various instances, act 2006 can include generating, by the device (e.g., via 120), a multi-tiered confidence score collection (e.g., 502) based on the set of anatomical landmarks and based on a localization training dataset (e.g., 110) on which the first deep learning neural network was trained.

In various cases, act 2008 can include generating, by the device (e.g., via 122), in response to one or more confidence scores from the multi-tiered confidence score collection failing to satisfy a threshold (e.g., 1502), and via execution of a second deep learning neural network (e.g., 1504), a classification label (e.g., 1506) that indicates an explanatory factor for why the one or more confidence scores failed to satisfy the threshold.

Although not explicitly shown in FIG. 20, a first tier of the multi-tiered confidence score collection can comprise landmark-wise confidence scores (e.g., 602) respectively corresponding to individual ones of the set of anatomical landmarks, a second tier of the multi-tiered confidence score collection can comprise pair-wise confidence scores (e.g., 604) respectively corresponding to anatomically symmetric pairs (e.g., 902) of the set of anatomical landmarks, a third tier of the multi-tiered confidence score collection can comprise group-wise confidence scores (e.g., 606) respectively corresponding to anthropometric groups (e.g., 1102) of the set of anatomical landmarks, and a fourth tier of the multi-tiered confidence score collection can comprise surface-wise confidence scores (e.g., 608) respectively corresponding to surface-defining groups (e.g., 1302) of the set of anatomical landmarks.

Although not explicitly shown in FIG. 20, the device can compute a landmark-wise confidence score (e.g., 602(*i*)) for an anatomical landmark (e.g., 106(*i*)) based on a comparison between: an attribute (e.g., 802) of a bounding box (e.g., 302(*i*)) predicted by the first deep learning neural network for the anatomical landmark as depicted in the three-dimensional voxel array; and a distribution of attributes (e.g., 806) of ground-truth bounding boxes (e.g., 804) that are known to correspond to the anatomical landmark as depicted in the localization training dataset.

Although not explicitly shown in FIG. 20, the device can compute a pair-wise confidence score (e.g., 604(*j*)) for an anatomically symmetric pair (e.g., 902(*j*)) of anatomical landmarks based on a multiplicative product of and an absolute difference between two landmark-wise confidence scores (e.g., 602($j_1$) and 602 ($j_2$)) respectively corresponding to the anatomically symmetric pair of anatomical landmarks.

Although not explicitly shown in FIG. 20, wherein the device can compute a group-wise confidence score (e.g., 606(*k*)) for an anthropometric group (e.g., 1102(*k*)) of anatomical landmarks based on a comparison between: a geometric interrelation (e.g., 1204) of bounding boxes (e.g., 1202) predicted by the first deep learning neural network for the anthropometric group of anatomical landmarks as depicted in the three-dimensional voxel array; and a distribution of geometric interrelations (e.g., 1210) between ground-truth bounding boxes (e.g., 1206) that are known to correspond to the anthropometric group of anatomical landmarks as depicted in the localization training dataset.

Although not explicitly shown in FIG. 20, the device can compute a surface-wise confidence score (e.g., 608(*l*)) for a surface-defining group (e.g., 1302(*l*)) of anatomical landmarks based on a comparison between: an intensity or gradient attribute of a physiological surface (e.g., 1404) determined using bounding boxes (e.g., 1402) predicted by the first deep learning neural network for the surface-defining group of anatomical landmarks as depicted in the three-dimensional voxel array; and a distribution of intensity or gradient attributes of physiological surfaces (e.g., 1410) determined using ground-truth bounding boxes (e.g., 1406) that are known to correspond to the surface-defining group of anatomical landmarks as depicted in the localization training dataset.

Although not explicitly shown in FIG. 20, the explanatory factor can comprise one or more of the following: that an imaging artifact or acquisition artifact is depicted in the three-dimensional voxel array; that a pathology is depicted in the three-dimensional voxel array; that the three-dimensional voxel array exhibits an incorrect field of view; that the three-dimensional voxel array exhibits an incorrect radiation dosage; or that the three-dimensional voxel array depicts an incorrect anatomy.

Although not explicitly shown in FIG. 20, the computer-implemented method 2000 can comprise: visually rendering, by the device (e.g., via 122 or via any other component of 102) and on an electronic display, the classification label and an alert indicating that whichever of the set of anatomical landmarks localized by the first deep learning neural network that correspond to the one or more confidence scores should not be relied upon for downstream inferencing tasks.

The herein disclosure has mainly described various embodiments as applying to the localization of anatomical landmarks. However, these are mere non-limiting examples. In various aspects, various embodiments can be applied to the localization of any suitable landmarks (e.g., even to localization of non-anatomical landmarks that are depicted in non-medical voxel arrays). In such cases, the set of anatomical landmarks 106 can instead be referred to as a set of landmarks, the set of anatomically symmetric landmark pairs 902 can instead be referred to as a set of symmetric landmark pairs, the set of anthropometric landmark groups can instead be referred to as a set of metrically-related landmark groups, and the set of surface-defining landmark groups 1302 can define non-physiological surfaces instead of physiological surfaces. Furthermore, in such cases, rather than indicating that the 3D voxel array 104 depicts an incorrect, unexpected, or otherwise out-of-scope anatomy, the explanatory classification label 1506 can instead more generally indicate that the 3D voxel array 104 depicts incorrect, unexpected, or otherwise out-of-scope content.

In various instances, machine learning algorithms or models can be implemented in any suitable way to facilitate any suitable aspects described herein. To facilitate some of the above-described machine learning aspects of various embodiments, consider the following discussion of artificial intelligence (AI). Various embodiments described herein can employ artificial intelligence to facilitate automating one or more features or functionalities. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system or environment from a set of observations as captured via events or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events or data.

Such determinations can result in the construction of new events or actions from a set of observed events or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes or systems (e.g., support vector machines, neural networks, expert systems, Bayesian belief networks, fuzzy logic, data fusion engines, and so on) in connection with performing automatic or determined action in connection with the claimed subject matter. Thus, classification schemes or systems can be used to automatically learn and perform a number of functions, actions, or determinations.

A classifier can map an input attribute vector, $z=(z_1, z_2, z_3, z_4, z_n)$, to a confidence that the input belongs to a class, as by f(z)=confidence(class). Such classification can employ a probabilistic or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, or probabilistic classification models providing different patterns of independence, any of which can be employed. Classification as used herein also is inclusive of statistical regression that is utilized to develop models of priority.

Figure 21:
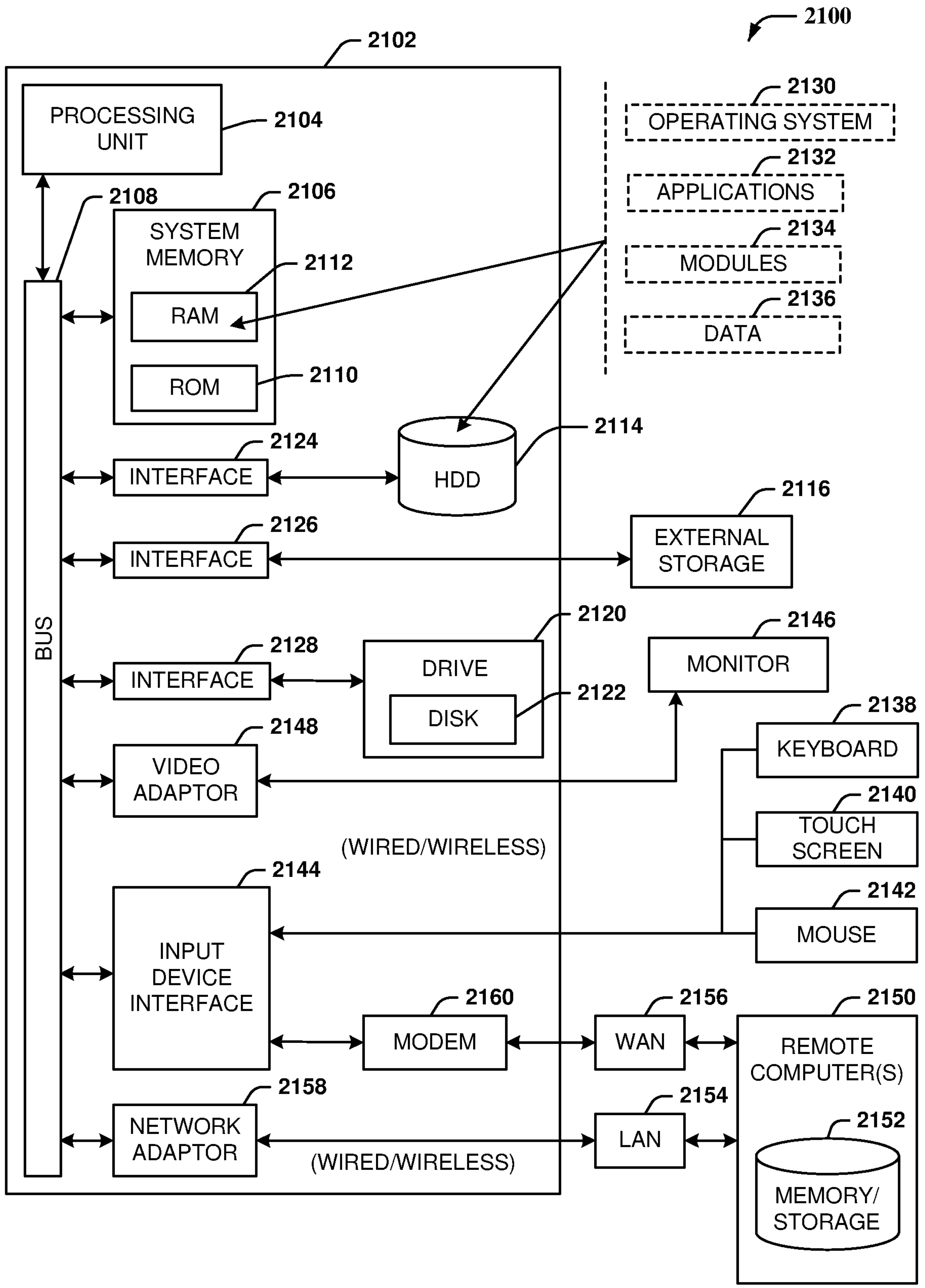
FIG. 21 illustrates a block diagram of an example, non-limiting operating environment in which one or more embodiments described herein can be facilitated.

In order to provide additional context for various embodiments described herein, FIG. 21 and the following discussion are intended to provide a brief, general description of a suitable computing environment 2100 in which the various embodiments of the embodiment described herein can be implemented. While the embodiments have been described above in the general context of computer-executable instructions that can run on one or more computers, those skilled in the art will recognize that the embodiments can be also implemented in combination with other program modules or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 21, the example environment 2100 for implementing various embodiments of the aspects described herein includes a computer 2102, the computer 2102 including a processing unit 2104, a system memory 2106 and a system bus 2108. The system bus 2108 couples system components including, but not limited to, the system memory 2106 to the processing unit 2104. The processing unit 2104 can be any of various commercially available processors. Dual microprocessors and other multi-processor architectures can also be employed as the processing unit 2104.

The system bus 2108 can be any of several types of bus structure that can further interconnect to a memory bus (with or without a memory controller), a peripheral bus, and a local bus using any of a variety of commercially available bus architectures. The system memory 2106 includes ROM 2110 and RAM 2112. A basic input/output system (BIOS) can be stored in a non-volatile memory such as ROM, erasable programmable read only memory (EPROM), EEPROM, which BIOS contains the basic routines that help to transfer information between elements within the computer 2102, such as during startup. The RAM 2112 can also include a high-speed RAM such as static RAM for caching data.

The computer 2102 further includes an internal hard disk drive (HDD) 2114 (e.g., EIDE, SATA), one or more external storage devices 2116 (e.g., a magnetic floppy disk drive (FDD) 2116, a memory stick or flash drive reader, a memory card reader, etc.) and a drive 2120, e.g., such as a solid state drive, an optical disk drive, which can read or write from a disk 2122, such as a CD-ROM disc, a DVD, a BD, etc. Alternatively, where a solid state drive is involved, disk 2122 would not be included, unless separate. While the internal HDD 2114 is illustrated as located within the computer 2102, the internal HDD 2114 can also be configured for external use in a suitable chassis (not shown). Additionally, while not shown in environment 2100, a solid state drive (SSD) could be used in addition to, or in place of, an HDD 2114. The HDD 2114, external storage device(s) 2116 and drive 2120 can be connected to the system bus 2108 by an HDD interface 2124, an external storage interface 2126 and a drive interface 2128, respectively. The interface 2124 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 2102, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 2112, including an operating system 2130, one or more application programs 2132, other program modules 2134 and program data 2136. All or portions of the operating system, applications, modules, or data can also be cached in the RAM 2112. The systems and methods described herein can be implemented utilizing various commercially available operating systems or combinations of operating systems.

Computer 2102 can optionally comprise emulation technologies. For example, a hypervisor (not shown) or other intermediary can emulate a hardware environment for operating system 2130, and the emulated hardware can optionally be different from the hardware illustrated in FIG. 21. In such an embodiment, operating system 2130 can comprise one virtual machine (VM) of multiple VMs hosted at computer 2102. Furthermore, operating system 2130 can provide runtime environments, such as the Java runtime environment or the .NET framework, for applications 2132. Runtime environments are consistent execution environments that allow applications 2132 to run on any operating system that includes the runtime environment. Similarly, operating system 2130 can support containers, and applications 2132 can be in the form of containers, which are lightweight, standalone, executable packages of software that include, e.g., code, runtime, system tools, system libraries and settings for an application.

Further, computer 2102 can be enable with a security module, such as a trusted processing module (TPM). For instance with a TPM, boot components hash next in time boot components, and wait for a match of results to secured values, before loading a next boot component. This process can take place at any layer in the code execution stack of computer 2102, e.g., applied at the application execution level or at the operating system (OS) kernel level, thereby enabling security at any level of code execution.

A user can enter commands and information into the computer 2102 through one or more wired/wireless input devices, e.g., a keyboard 2138, a touch screen 2140, and a pointing device, such as a mouse 2142. Other input devices (not shown) can include a microphone, an infrared (IR) remote control, a radio frequency (RF) remote control, or other remote control, a joystick, a virtual reality controller or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 2104 through an input device interface 2144 that can be coupled to the system bus 2108, but can be connected by other interfaces, such as a parallel port, an IEEE 1394 serial port, a game port, a USB port, an IR interface, a BLUETOOTH® interface, etc.

A monitor 2146 or other type of display device can be also connected to the system bus 2108 via an interface, such as a video adapter 2148. In addition to the monitor 2146, a computer typically includes other peripheral output devices (not shown), such as speakers, printers, etc.

The computer 2102 can operate in a networked environment using logical connections via wired or wireless communications to one or more remote computers, such as a remote computer(s) 2150. The remote computer(s) 2150 can be a workstation, a server computer, a router, a personal computer, portable computer, microprocessor-based entertainment appliance, a peer device or other common network node, and typically includes many or all of the elements described relative to the computer 2102, although, for purposes of brevity, only a memory/storage device 2152 is illustrated. The logical connections depicted include wired/wireless connectivity to a local area network (LAN) 2154 or larger networks, e.g., a wide area network (WAN) 2156. Such LAN and WAN networking environments are commonplace in offices and companies, and facilitate enterprise-wide computer networks, such as intranets, all of which can connect to a global communications network, e.g., the Internet.

When used in a LAN networking environment, the computer 2102 can be connected to the local network 2154 through a wired or wireless communication network interface or adapter 2158. The adapter 2158 can facilitate wired or wireless communication to the LAN 2154, which can also include a wireless access point (AP) disposed thereon for communicating with the adapter 2158 in a wireless mode.

When used in a WAN networking environment, the computer 2102 can include a modem 2160 or can be connected to a communications server on the WAN 2156 via other means for establishing communications over the WAN 2156, such as by way of the Internet. The modem 2160, which can be internal or external and a wired or wireless device, can be connected to the system bus 2108 via the input device interface 2144. In a networked environment, program modules depicted relative to the computer 2102 or portions thereof, can be stored in the remote memory/storage device 2152. It will be appreciated that the network connections shown are example and other means of establishing a communications link between the computers can be used.

When used in either a LAN or WAN networking environment, the computer 2102 can access cloud storage systems or other network-based storage systems in addition to, or in place of, external storage devices 2116 as described above, such as but not limited to a network virtual machine providing one or more aspects of storage or processing of information. Generally, a connection between the computer 2102 and a cloud storage system can be established over a LAN 2154 or WAN 2156 e.g., by the adapter 2158 or modem 2160, respectively. Upon connecting the computer 2102 to an associated cloud storage system, the external storage interface 2126 can, with the aid of the adapter 2158 or modem 2160, manage storage provided by the cloud storage system as it would other types of external storage. For instance, the external storage interface 2126 can be configured to provide access to cloud storage sources as if those sources were physically connected to the computer 2102.

The computer 2102 can be operable to communicate with any wireless devices or entities operatively disposed in wireless communication, e.g., a printer, scanner, desktop or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies.

Thus, the communication can be a predefined structure as with a conventional network or simply an ad hoc communication between at least two devices.

Figure 22:
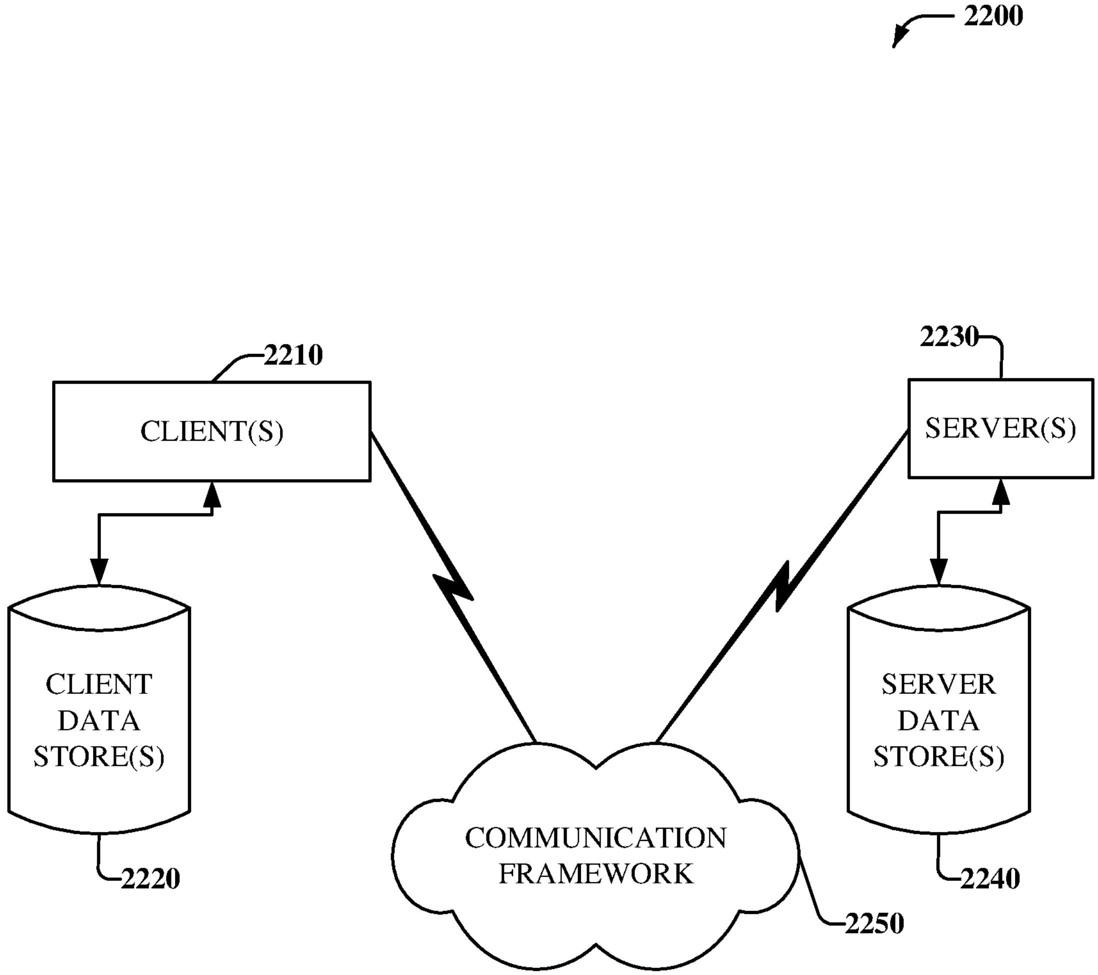
FIG. 22 illustrates an example networking environment operable to execute various implementations described herein.

FIG. 22 is a schematic block diagram of a sample computing environment 2200 with which the disclosed subject matter can interact. The sample computing environment 2200 includes one or more client(s) 2210. The client(s) 2210 can be hardware or software (e.g., threads, processes, computing devices). The sample computing environment 2200 also includes one or more server(s) 2230. The server(s) 2230 can also be hardware or software (e.g., threads, processes, computing devices). The servers 2230 can house threads to perform transformations by employing one or more embodiments as described herein, for example. One possible communication between a client 2210 and a server 2230 can be in the form of a data packet adapted to be transmitted between two or more computer processes. The sample computing environment 2200 includes a communication framework 2250 that can be employed to facilitate communications between the client(s) 2210 and the server(s) 2230. The client(s) 2210 are operably connected to one or more client data store(s) 2220 that can be employed to store information local to the client(s) 2210. Similarly, the server(s) 2230 are operably connected to one or more server data store(s) 2240 that can be employed to store information local to the servers 2230.

Various embodiments may be a system, a method, an apparatus or a computer program product at any possible technical detail level of integration. The computer program product can include a computer readable storage medium (or media) having computer readable program instructions thereon for causing a processor to carry out aspects of various embodiments. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network or a wireless network. The network can comprise copper transmission cables, optical transmission fibers, wireless transmission, routers, firewalls, switches, gateway computers or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various embodiments can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform various aspects.

Various aspects are described herein with reference to flowchart illustrations or block diagrams of methods, apparatus (systems), and computer program products according to various embodiments. It will be understood that each block of the flowchart illustrations or block diagrams, and combinations of blocks in the flowchart illustrations or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart or block diagram block or blocks. These computer readable program instructions can also be stored in a computer readable storage medium that can direct a computer, a programmable data processing apparatus, or other devices to function in a particular manner, such that the computer readable storage medium having instructions stored therein comprises an article of manufacture including instructions which implement aspects of the function/act specified in the flowchart or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart or block diagram block or blocks.

The flowcharts and block diagrams in the Figures illustrate the architecture, functionality, and operation of possible implementations of systems, methods, and computer program products according to various embodiments. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer or computers, those skilled in the art will recognize that this disclosure also can or can be implemented in combination with other program modules. Generally, program modules include routines, programs, components, data structures, etc. that perform particular tasks or implement particular abstract data types. Moreover, those skilled in the art will appreciate that various aspects can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, or a computer. By way of illustration, both an application running on a server and the server can be a component. One or more components can reside within a process or thread of execution and a component can be localized on one computer or distributed between two or more computers. In another example, respective components can execute from various computer readable media having various data structures stored thereon. The components can communicate via local or remote processes such as in accordance with a signal having one or more data packets (e.g., data from one component interacting with another component in a local system, distributed system, or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "of" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. As used herein, the term "and/or" is intended to have the same meaning as "or." Moreover, articles "a" and "an" as used in the subject specification and annexed drawings should generally be construed to mean "one or more" unless specified otherwise or clear from context to be directed to a singular form. As used herein, the terms "example" or "exemplary" are utilized to mean serving as an example, instance, or illustration. For the avoidance of doubt, the subject matter disclosed herein is not limited by such examples. In addition, any aspect or design described herein as an "example" or "exemplary" is not necessarily to be construed as preferred or advantageous over other aspects or designs, nor is it meant to preclude equivalent exemplary structures and techniques known to those of ordinary skill in the art.

The herein disclosure describes non-limiting examples. For ease of description or explanation, various portions of the herein disclosure utilize the term "each," "every," or "all" when discussing various examples. Such usages of the term "each," "every," or "all" are non-limiting. In other words, when the herein disclosure provides a description that is applied to "each," "every," or "all" of some particular object or component, it should be understood that this is a non-limiting example, and it should be further understood that, in various other examples, it can be the case that such description applies to fewer than "each," "every," or "all" of that particular object or component.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:

a processor that executes computer-executable components stored in a non-transitory computer-readable memory, wherein the computer-executable components comprise:

an access component that accesses a three-dimensional voxel array captured by a medical imaging scanner;

an execution component that localizes, via execution of a first deep learning neural network, a set of anatomical landmarks depicted in the three-dimensional voxel array;

a confidence component that generates a multi-tiered confidence score collection based on the set of anatomical landmarks and based on a localization training dataset on which the first deep learning neural network was trained; and a classifier component that, in response to one or more confidence scores from the multi-tiered confidence score collection failing to satisfy a threshold, generates, via execution of a second deep learning neural network, a classification label for the one or more confidence scores, wherein the classification label indicates an explanatory factor for why the one or more confidence scores failed to satisfy the threshold.

2. The system of claim 1, wherein a first tier of the multi-tiered confidence score collection comprises landmark-wise confidence scores respectively corresponding to individual ones of the set of anatomical landmarks, wherein a second tier of the multi-tiered confidence score collection comprises pair-wise confidence scores respectively corresponding to anatomically symmetric pairs of the set of anatomical landmarks, wherein a third tier of the multi-tiered confidence score collection comprises group-wise confidence scores respectively corresponding to anthropometric groups of the set of anatomical landmarks, and wherein a fourth tier of the multi-tiered confidence score collection comprises surface-wise confidence scores respectively corresponding to surface-defining groups of the set of anatomical landmarks.

3. The system of claim 2, wherein the confidence component computes a landmark-wise confidence score for an anatomical landmark based on a comparison between:

an attribute of a bounding box predicted by the first deep learning neural network for the anatomical landmark as depicted in the three-dimensional voxel array; and a distribution of attributes of ground-truth bounding boxes that are known to correspond to the anatomical landmark as depicted in the localization training dataset.

4. The system of claim 2, wherein the confidence component computes a pair-wise confidence score for an anatomically symmetric pair of anatomical landmarks based on a multiplicative product of and an absolute difference between two landmark-wise confidence scores respectively corresponding to the anatomically symmetric pair of anatomical landmarks.

5. The system of claim 2, wherein the confidence component computes a group-wise confidence score for an anthropometric group of anatomical landmarks based on a comparison between:

a geometric interrelation of bounding boxes predicted by the first deep learning neural network for the anthropometric group of anatomical landmarks as depicted in the three-dimensional voxel array; and a distribution of geometric interrelations between ground-truth bounding boxes that are known to correspond to the anthropometric group of anatomical landmarks as depicted in the localization training dataset.

6. The system of claim 2, wherein the confidence component computes a surface-wise confidence score for a surface-defining group of anatomical landmarks based on a comparison between:

an intensity or gradient attribute of a physiological surface determined using bounding boxes predicted by the first deep learning neural network for the surface-defining group of anatomical landmarks as depicted in the three-dimensional voxel array; and a distribution of intensity or gradient attributes of physiological surfaces determined using ground-truth bounding boxes that are known to correspond to the surface-defining group of anatomical landmarks as depicted in the localization training dataset.

7. The system of claim 1, wherein the explanatory factor comprises one or more of the following: that an imaging artifact or acquisition artifact is depicted in the three-dimensional voxel array; that a pathology is depicted in the three-dimensional voxel array; that the three-dimensional voxel array exhibits an incorrect field of view; that the three-dimensional voxel array exhibits an incorrect radiation dosage; or that the three-dimensional voxel array depicts an incorrect anatomy.

8. The system of claim 1, wherein the classifier component visually renders, on an electronic display, the classification label and an alert indicating that whichever of the set of anatomical landmarks localized by the first deep learning neural network that correspond to the one or more confidence scores should not be relied upon for downstream inferencing tasks.

9. A computer-implemented method, comprising:

accessing, by a device operatively coupled to a processor, a three-dimensional voxel array captured by a medical imaging scanner;

localizing, by the device and via execution of a first deep learning neural network, a set of anatomical landmarks depicted in the three-dimensional voxel array;

generating, by the device, a multi-tiered confidence score collection based on the set of anatomical landmarks and based on a localization training dataset on which the first deep learning neural network was trained; and generating, by the device, in response to one or more confidence scores from the multi-tiered confidence score collection failing to satisfy a threshold, and via execution of a second deep learning neural network, a classification label for the one or more confidence scores, wherein the classification label indicates an explanatory factor for why the one or more confidence scores failed to satisfy the threshold.

10. The computer-implemented method of claim 9, wherein a first tier of the multi-tiered confidence score collection comprises landmark-wise confidence scores respectively corresponding to individual ones of the set of anatomical landmarks, wherein a second tier of the multi-tiered confidence score collection comprises pair-wise confidence scores respectively corresponding to anatomically symmetric pairs of the set of anatomical landmarks, wherein a third tier of the multi-tiered confidence score collection comprises group-wise confidence scores respectively corresponding to anthropometric groups of the set of anatomical landmarks, and wherein a fourth tier of the multi-tiered confidence score collection comprises surface-wise confidence scores respectively corresponding to surface-defining groups of the set of anatomical landmarks.

11. The computer-implemented method of claim 10, wherein the device computes a landmark-wise confidence score for an anatomical landmark based on a comparison between:

an attribute of a bounding box predicted by the first deep learning neural network for the anatomical landmark as depicted in the three-dimensional voxel array; and a distribution of attributes of ground-truth bounding boxes that are known to correspond to the anatomical landmark as depicted in the localization training dataset.

12. The computer-implemented method of claim 10, wherein the device computes a pair-wise confidence score for an anatomically symmetric pair of anatomical landmarks based on a multiplicative product of and an absolute difference between two landmark-wise confidence scores respectively corresponding to the anatomically symmetric pair of anatomical landmarks.

13. The computer-implemented method of claim 10, wherein the device computes a group-wise confidence score for an anthropometric group of anatomical landmarks based on a comparison between:

a geometric interrelation of bounding boxes predicted by the first deep learning neural network for the anthropometric group of anatomical landmarks as depicted in the three-dimensional voxel array; and a distribution of geometric interrelations between ground-truth bounding boxes that are known to correspond to the anthropometric group of anatomical landmarks as depicted in the localization training dataset.

14. The computer-implemented method of claim 10, wherein the device computes a surface-wise confidence score for a surface-defining group of anatomical landmarks based on a comparison between:

an intensity or gradient attribute of a physiological surface determined using bounding boxes predicted by the first deep learning neural network for the surface-defining group of anatomical landmarks as depicted in the three-dimensional voxel array; and a distribution of intensity or gradient attributes of physiological surfaces determined using ground-truth bounding boxes that are known to correspond to the surface-defining group of anatomical landmarks as depicted in the localization training dataset.

15. The computer-implemented method of claim 9, wherein the explanatory factor comprises one or more of the following: that an imaging artifact or acquisition artifact is depicted in the three-dimensional voxel array; that a pathology is depicted in the three-dimensional voxel array; that the three-dimensional voxel array exhibits an incorrect field of view; that the three-dimensional voxel array exhibits an incorrect radiation dosage; or that the three-dimensional voxel array depicts an incorrect anatomy.

16. The computer-implemented method of claim 9, further comprising:

visually rendering, by the device and on an electronic display, the classification label and an alert indicating that whichever of the set of anatomical landmarks localized by the first deep learning neural network that correspond to the one or more confidence scores should not be relied upon for downstream inferencing tasks.

17. A computer program product for facilitating explainable confidence estimation for landmark localization, the computer program product comprising a computer-readable memory having program instructions embodied therewith, the program instructions executable by a processor to cause the processor to:

access a three-dimensional voxel array;

localize, via execution of a first deep learning neural network, a set of landmarks depicted in the three-dimensional voxel array;

generate a multi-tiered confidence score collection based on the set of landmarks and based on a localization training dataset on which the first deep learning neural network was trained; and generate in response to one or more confidence scores from the multi-tiered confidence score collection failing to satisfy a threshold, and via execution of a second deep learning neural network, a classification label for the one or more confidence scores, wherein the classification label indicates an explanatory factor for why the one or more confidence scores failed to satisfy the threshold.

18. The computer program product of claim 17, wherein a first tier of the multi-tiered confidence score collection comprises landmark-wise confidence scores respectively corresponding to individual ones of the set of landmarks, wherein a second tier of the multi-tiered confidence score collection comprises pair-wise confidence scores respectively corresponding to symmetric pairs of the set of landmarks, wherein a third tier of the multi-tiered confidence score collection comprises group-wise confidence scores respectively corresponding to metrically-related groups of the set of landmarks, and wherein a fourth tier of the multi-tiered confidence score collection comprises surface-wise confidence scores respectively corresponding to surface-defining groups of the set of landmarks.

19. The computer program product of claim 17, wherein the explanatory factor is that an imaging artifact is depicted in the three-dimensional voxel array, that the three-dimensional voxel array exhibits an incorrect field of view, or that the three-dimensional voxel array depicts incorrect content.

20. The computer program product of claim 17, wherein the program instructions are further executable to cause the processor to:

visually render, on an electronic display, the classification label and an alert indicating that whichever of the set of landmarks localized by the first deep learning neural network that correspond to the one or more confidence scores should not be relied upon for downstream inferencing tasks.

* * * * *